US006872725B2

(12) United States Patent
Allen et al.

(10) Patent No.: US 6,872,725 B2
(45) Date of Patent: Mar. 29, 2005

(54) SOLID-STATE FORMS OF N-(2-HYDROXYACETYL)-5-(4-PIPERIDYL)-4-(4-PYRIMIDINYL)-3-(4-CHLOROPHENYL) PYRAZOLE

(75) Inventors: Kimberley C. Allen, Chicago, IL (US); Jerry D. Clark, Alton, IL (US); Thomas P. Fraher, Chicago, IL (US); Jason A. Hanko, Napierville, IL (US); Kimberly L. Kolbert, Elmhurst, IL (US); Clay R. Little, Lindenhurst, IL (US); Michael K. Mao, Chesterfield, MO (US); Patricia S. Miyake, Tower Lakes, IL (US); Jodi L. Moe, Buffalo Grove, IL (US); Partha S. Mudipalli, Skokie, IL (US); Tobin C. Schilke, Ithaca, NY (US); Christine B. Seymour, Glenview, IL (US); Ahmad Y. Sheikh, Des Plaines, IL (US); Gopichand Yalamanchili, St. Louis, MO (US)

(73) Assignee: Pharmacia Corporation, St. Louis, MO (US)

( * ) Notice: Subject to any disclaimer, the term of this patent is extended or adjusted under 35 U.S.C. 154(b) by 101 days.

(21) Appl. No.: 10/254,697

(22) Filed: Sep. 25, 2002

(65) Prior Publication Data

US 2003/0153583 A1 Aug. 14, 2003

Related U.S. Application Data

(60) Provisional application No. 60/324,987, filed on Sep. 25, 2001.

(51) Int. Cl.$^7$ .................. C07D 401/14; A31K 31/506; A61P 19/02
(52) U.S. Cl. ...................................... 514/256; 544/333
(58) Field of Search ........................ 514/256; 544/333

(56) References Cited

U.S. PATENT DOCUMENTS

| | | | |
|---|---|---|---|
| 4,826,689 A | 5/1989 | Violanto et al. ............ | 424/489 |
| 5,145,684 A | 9/1992 | Liversidge et al. ......... | 424/489 |
| 5,298,262 A | 3/1994 | Na et al. .................... | 424/489 |
| 5,302,401 A | 4/1994 | Liversidge et al. ......... | 424/501 |
| 5,336,507 A | 8/1994 | Na et al. .................... | 424/489 |
| 5,340,564 A | 8/1994 | Illig et al. ..................... | 424/9 |
| 5,346,702 A | 9/1994 | Na et al. .................... | 424/490 |
| 5,352,459 A | 10/1994 | Hollister et al. ............. | 424/489 |
| 5,354,560 A | 10/1994 | Lovrecich .................. | 424/489 |
| 5,384,124 A | 1/1995 | Courteille et al. ........... | 424/430 |
| 5,429,824 A | 7/1995 | June ........................... | 424/489 |
| 5,503,723 A | 4/1996 | Ruddy et al. ............... | 204/450 |
| 5,510,118 A | 4/1996 | Bosch et al. ................ | 424/489 |
| 5,518,187 A | 5/1996 | Bruno et al. ................... | 241/5 |
| 5,518,738 A | 5/1996 | Eickhoff et al. ............ | 424/493 |
| 5,534,270 A | 7/1996 | De Castro .................. | 424/490 |
| 5,536,508 A | 7/1996 | Canal et al. ................ | 424/501 |
| 5,552,160 A | 9/1996 | Liversidge et al. ......... | 424/489 |
| 5,560,931 A | 10/1996 | Eickhoff et al. ............ | 424/489 |
| 5,560,932 A | 10/1996 | Bagchi et al. .............. | 424/489 |
| 5,565,188 A | 10/1996 | Wong et al. ............. | 424/9.411 |
| 5,569,448 A | 10/1996 | Wong et al. ................ | 424/9.45 |
| 5,571,536 A | 11/1996 | Eickhoff et al. ............ | 424/489 |
| 5,573,783 A | 11/1996 | Desieno et al. ............. | 424/490 |
| 5,580,579 A | 12/1996 | Ruddy et al. ............... | 424/489 |
| 5,585,108 A | 12/1996 | Ruddy et al. ............... | 424/434 |
| 5,587,143 A | 12/1996 | Wong ......................... | 424/9.1 |
| 5,591,456 A | 1/1997 | Franson et al. ............. | 424/494 |
| 5,622,938 A | 4/1997 | Wong ......................... | 514/35 |
| 5,662,883 A | 9/1997 | Bagchi et al. .............. | 424/9.4 |
| 5,665,331 A | 9/1997 | Bagchi et al. ............. | 424/9.45 |
| 5,718,919 A | 2/1998 | Ruddy et al. ............... | 424/489 |
| 5,747,001 A | 5/1998 | Wiedmann et al. .......... | 424/45 |

FOREIGN PATENT DOCUMENTS

| | | |
|---|---|---|
| WO | 93/25190 | 12/1993 |
| WO | 96/24336 | 8/1996 |
| WO | 98/35666 | 8/1998 |

OTHER PUBLICATIONS

Lee, J.C. et al, Immunopharmacology, 47, 2000, 185–201.*
Rebecca K Studer; Rachel Bergman; Tiffany Stubbs; Kimberly Decker, Arthritis Res Ther 6(1):R56–R64, 2004.*
No Author, Expert. Opin. Ther. Patents 13(3) 2003, 381–385.*
Ward KW, Proksch JW, Salyers KL, Azzarano LM, Morgan JA, Roethke TJ, McSurdy–Freed JE, Levy MA, Smith BR .Xenobiotica. Mar. 2002, 32(3):221–33. Medline abstract PMID: 11958561.*
West, Anthony R., Solid State Chemistry and its Applications, Wiley, New York, 1988, pp. 358 & 365.*

* cited by examiner

Primary Examiner—Thomas C. McKenzie
(74) Attorney, Agent, or Firm—Julie M. Lappin; Joseph R. Schuh

(57) ABSTRACT

Crystalline forms of the p38 kinase inhibitor N-(2-hydroxyacetyl)-5-(4-piperidyl)-4-(4-pyrimidinyl)-3-(4-chlorophenyl)pyrazole are provided. These crystalline forms include (a) a first anhydrous crystalline form possessing improved physical stability relative to other solid-state forms of the compound; (b) a second anhydrous crystalline form possessing unique properties relative to other solid-state forms of the compound; (c) a third anhydrous crystalline form possessing unique properties relative to other solid-state forms of the compound; and (d) solvated crystalline forms, hydrated crystalline forms, and crystalline salt forms of the compound that are useful, for example, as intermediate solid-state forms in the preparation of other crystalline forms of the compound. Also provided are combinations and pharmaceutical compositions comprising at least one of these crystalline forms, processes for preparing these crystalline forms and for preparing compositions comprising these crystalline forms, and methods for the prophylaxis and/or treatment of a p38 kinase-mediated condition comprising administering to a subject a therapeutically effective amount of at least one of these crystalline forms.

39 Claims, 44 Drawing Sheets

SOLID-STATE FORMS OF N-(2-HYDROXYACETYL)-5-(4-PIPERIDYL)-4-(4-PYRIMIDINYL)-3-(4-CHLOROPHENYL)PYRAZOLE

CROSS-REFERENCE TO RELATED PATENT APPLICATION

This patent claims priority to U.S. Provisional Application Ser. No. 60/324,987 (filed Sep. 25, 2001). The entire text of this provisional application is incorporated by reference into the present application.

FIELD OF THE INVENTION

This invention is in the field of pharmaceutical agents active as p38 kinase inhibitors, and more particularly concerns the p38 kinase inhibitor N-(2-hydroxyacetyl)-5-(4-piperidyl)-4-(4-pyrimidinyl)-3-(4-chlorophenyl)pyrazole. Specifically, the invention relates to (a) novel solid-state forms of N-(2-hydroxyacetyl)-5-(4-piperidyl)-4-(4-pyrimidinyl)-3-(4-chlorophenyl)pyrazole, (b) methods of preparing these solid-state forms, (c) intermediate solid-state forms useful in preparing crystalline solid-state forms, (d) pharmaceutical compositions comprising one or more of these solid-state forms, (e) methods for the treatment and/or prophylaxis of a p38 kinase-mediated condition (including conditions associated with inflammation such as arthritis), (f) methods for regulating the synthesis of inflammatory cytokines such as tumor necrosis factor ("TNF") and interleukin-1 ("IL-1"), and (g) use of one or more of these solid-state forms in the manufacture of medicaments.

BACKGROUND OF THE INVENTION

The compound N-(2-hydroxyacetyl)-5-(4-piperidyl)-4-(4-pyrimidinyl)-3-(4-chlorophenyl)pyrazole having the structure (I) below (referred to herein as "Compound 1") was previously reported in International Patent Publication No. WO00/31063. WO00/31063 generically discloses a class of substituted pyrazole compounds and related pharmaceutical compositions that are useful for the treatment and/or prophylaxis of a p38 kinase-mediated condition. Examples D-1 and D-2 of WO00/31063 specifically disclose Compound 1 and methods for the synthesis of Compound 1. WO00/31063 is incorporated herein by reference as if fully set forth at length.

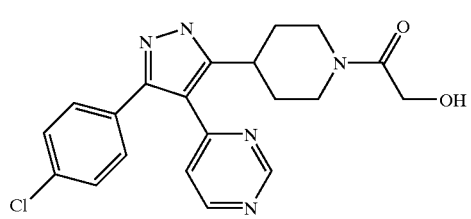

1

Compound 1 previously has not been known to exist in a stable crystalline form. A need exists for crystalline forms of Compound 1 that are physically stable and sufficiently bioavailable, and for reliable and reproducible processes for the manufacture and/or purification of such crystalline forms. There is now provided (a) a novel crystalline form of Compound 1 having a high degree of physical stability at normal temperatures of storage and use, and having other unique properties relative to other solid-state forms of Compound 1, (b) several other novel crystalline forms of Compound 1 having other unique properties relative to other solid-state forms of Compound 1, and (c) methods and intermediate solid-state forms for the preparation of these novel crystalline forms of Compound 1, including methods for the removal of impurities from these crystalline forms.

SUMMARY OF THE INVENTION

The invention provides, in a first aspect, a crystalline form of Compound 1.

In another aspect, the invention provides a first anhydrous crystalline form of Compound 1 (the "Form I polymorph") possessing improved physical stability relative to other solid-state forms of Compound 1.

In another aspect, the invention provides a second anhydrous crystalline form of Compound 1 (the "Form II polymorph") possessing unique properties relative to other solid-state forms of Compound 1.

In another aspect, the invention provides a third anhydrous crystalline form of Compound 1 (the "Form III polymorph") possessing unique properties relative to other solid-state forms of Compound 1.

In another aspect, the invention provides solvated crystalline forms of Compound 1 that are useful, for example, as intermediates in the preparation of other crystalline forms of Compound 1.

In another aspect, the invention provides hydrated crystalline forms of Compound 1 that are useful, for example, as intermediates in the preparation of other crystalline forms of Compound 1.

In another aspect, the invention provides crystalline salts of Compound 1 that are useful, for example, as intermediates in the preparation of other crystalline forms of Compound 1.

In another aspect, the invention provides pharmaceutical compositions comprising at least one crystalline form of Compound 1, optionally accompanied by one or more other solid-state forms of Compound 1, and further optionally comprising one or more pharmaceutically acceptable excipients.

In another aspect, the invention provides pharmaceutical compositions containing about 0.1 mg to about 1000 mg of at least one crystalline form of Compound 1.

In another aspect, the invention provides processes for preparing crystalline forms of Compound 1 and for preparing compositions comprising crystalline forms of Compound 1.

In another aspect, the invention provides a method for prophylaxis and/or treatment of p38 kinase-mediated condition comprising administering to a subject a therapeutically effective amount of at least one crystalline form of Compound 1.

Additional aspects of the invention will be in part apparent and in part pointed out throughout this application.

DETAILED DESCRIPTION OF THE INVENTION

Figure 1:
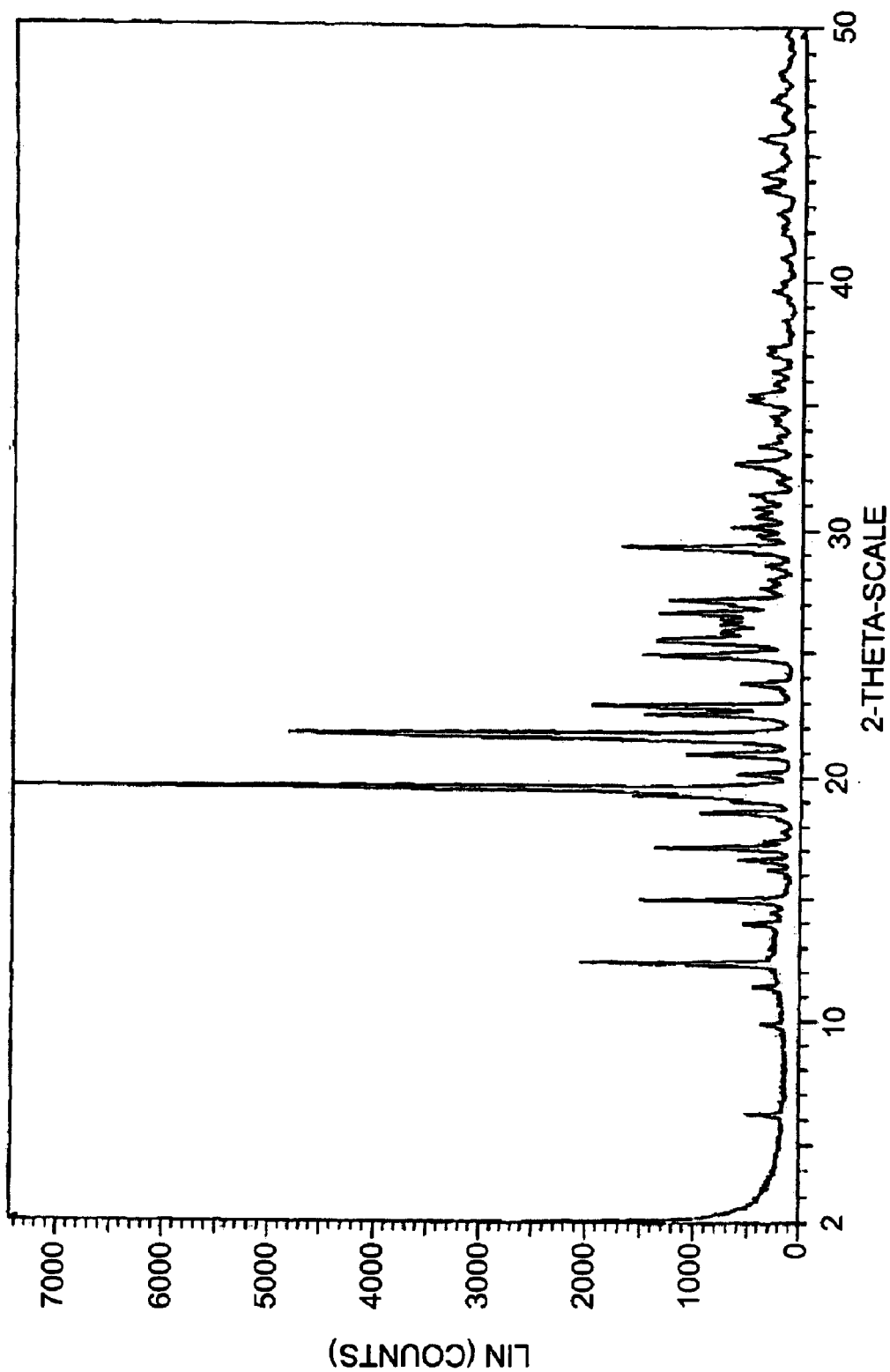
FIG. 1 shows an illustrative X-ray powder diffraction pattern for the Form I polymorph of Compound 1.

As with all pharmaceutical compounds and compositions, the chemical and physical properties of N-(2-hydroxyacetyl)-5-(4-piperidyl)-4-(4-pyrimidinyl)-3-(4-chlorophenyl)pyrazole ("Compound 1") are important in its commercial development. These properties include, but are not limited to: (1) packing properties such as molar volume, density and hygroscopicity, (2) thermodynamic properties such as melting temperature, vapor pressure and solubility, (3) kinetic properties such as dissolution rate and stability (including stability at ambient conditions, especially to moisture, and under storage conditions), (4) surface properties such as surface area, wettability, interfacial tension and shape, (5) mechanical properties such as hardness, tensile strength, compactibility, handling, flow and blend, (6) filtration properties, (7) chemical purity, and (8) physical and chemical stability. These properties can affect, for example, processing and storage of pharmaceutical compositions comprising Compound 1. Solid-state forms of Compound 1 that provide an improvement in one or more of these properties relative to other solid-state forms of Compound 1 are desirable.

According to the present invention, therefore, several new solid-state forms of Compound 1 have been discovered.

These solid-state forms of Compound 1 possess one or more of the above-described advantageous chemical, and/or physical properties relative to other solid-state forms of Compound 1 and/or are useful as intermediates in the preparation of one or more other solid-state forms of Compound 1. The specific solid-state forms of Compound 1 that have been discovered include the following:

(1) a first anhydrous crystalline form of Compound 1 possessing improved physical stability relative to other solid-state forms of Compound 1 (the "Form I polymorph");

(2) a second anhydrous crystalline form of Compound 1 possessing unique properties relative to other solid-state forms of Compound 1 (the "Form II polymorph");

(3) a third anhydrous crystalline form of Compound 1 possessing unique properties relative to other solid-state forms of Compound 1 (the "Form III polymorph");

(4) an acetic acid solvated crystalline form of Compound 1 that is useful, for example, as an intermediate in the preparation of other crystalline forms of Compound 1 (the "acetic acid solvate");

(5) an N-methylpyrrolidone ("NMP") solvated crystalline form of Compound 1 that is useful, for example, as an intermediate in the preparation of other crystalline forms of Compound 1 (the "NMP solvate");

(6) a monohydrated crystalline form of Compound 1 that is useful, for example, as an intermediate in the preparation of other crystalline forms of Compound 1 (the "monohydrate crystalline form");

(7) a dihydrated crystalline form of Compound 1 that is useful, for example, as an intermediate in the preparation of other crystalline forms of Compound 1 (the "dihydrate crystalline form"); and (8) crystalline salt forms of Compound 1 that are useful, for example, as intermediates in the preparation of other crystalline forms of Compound 1. Non-limiting examples of crystalline salt forms of Compound 1 include sodium, hydrochloride, mesylate and tosylate forms.

In one embodiment, the invention comprises the Form I polymorph of Compound 1. The Form I polymorph possesses greater physical stability at ambient temperatures than the other solid-state forms of Compound 1. Solid-state forms of Compound 1 that do not require special processing or storage conditions, and that avoid the need for frequent inventory replacement, such as the Form I polymorph, are desirable. For example, selection of a solid-state form of Compound 1 that is physically stable during a manufacturing process (such as during milling of Compound 1 to obtain a material with reduced particle size and increased surface area) can avoid the need for special processing conditions and the increased costs generally associated with such special processing conditions. Similarly, selection of a solid-state form of Compound 1 that is physically stable over a wide range of storage conditions (especially considering the different possible storage conditions that can occur during the lifetime of a Compound 1 product) can help avoid polymorphic or other degradative changes in the Compound 1 that can lead to product loss or deterioration of product efficacy. Therefore, the selection of a solid-state form of Compound 1 such as the Form I polymorph having greater physical stability provides a meaningful benefit over less stable Compound 1 solid-state forms.

In another embodiment, the invention comprises the Form II polymorph of Compound 1. The Form II polymorph exhibits a faster dissolution rate in an aqueous medium than, for example, the Form I polymorph (approximately two- to three-fold faster than the dissolution rate of the Form I polymorph). Where dissolution of Compound 1 in the gastrointestinal tract is the rate-controlling step for delivery of the Compound 1 to target cells or tissues, faster dissolution generally results in improved bioavailability. The Form II polymorph, therefore, can provide an improved bioavailability profile relative to other solid-state forms of Compound 1. In addition, selection of a solid-state form of Compound 1 having a faster dissolution rate likewise provides greater flexibility in selection of excipients for, and in formulation of, pharmaceutical compositions, particularly those intended to exhibit immediate release of Compound 1, relative to other solid-state forms having a slower dissolution rate.

In another embodiment, the invention comprises the Form III polymorph of Compound 1. The Form III polymorph is hypothesized to have greater physical stability and/or to exhibit a faster dissolution rate relative to some or all of the other solid-state forms of Compound 1.

In another embodiment, the invention comprises a solvated crystalline form of Compound 1, particularly the acetic acid solvate or the NMP solvate. Of particular interest in the context of the present invention are solvated crystalline forms of Compound 1 that can be converted into the Form I polymorph or the Form II polymorph. The acetic acid solvate is useful as an intermediate in the preparation of the Form II polymorph, i.e., the acetic acid solvate can be converted into the Form II polymorph. The NMP solvate is useful as an intermediate in the preparation of either the Form I polymorph or the Form II polymorph, i.e., the NMP solvate can be converted into either the Form I polymorph or the Form II polymorph, depending upon the conditions selected.

Pharmaceutically acceptable solvated crystalline forms of Compound 1 also can be used directly in pharmaceutical compositions. For this use, the solvated crystalline forms of Compound 1 preferably are substantially exclusive of solvents that are not pharmaceutically acceptable solvents. Solvated crystalline forms used in pharmaceutical compositions generally and preferably comprise a pharmaceutically acceptable higher boiling point and/or hydrogen-bonding solvent. It is believed that the solvated crystalline forms collectively can offer a range of different dissolution rates and, where dissolution of Compound 1 in the gastrointestinal tract is the rate-controlling step for delivery of Compound 1 to the target cells or tissues, a range of different bioavailabilities relative to other solid-state forms of Compound 1.

In another embodiment, the invention comprises a hydrated crystalline form of Compound 1, particularly the monohydrate crystalline form or the dihydrate crystalline form. The monohydrate crystalline form is useful as an intermediate in the preparation of the Form I polymorph, i.e., the monohydrate crystalline form is converted into the Form I polymorph. The dihydrate crystalline form is useful as an intermediate in the preparation of either the Form I polymorph or the Form III polymorph, i.e., the dihydrate crystalline form is converted into the Form I polymorph or the Form III polymorph, depending upon the conditions selected. Pharmaceutically acceptable hydrated crystalline forms of Compound 1 also can be used directly in pharmaceutical compositions. It is believed that the hydrated crystalline forms collectively can offer a range of different dissolution rates and, where dissolution of Compound 1 in the gastrointestinal tract is the rate-controlling step for delivery of Compound 1 to the target cells or tissues, a range of different bioavailabilities relative to other solid-state forms of Compound 1.

In another embodiment, the invention comprises crystalline salt forms of Compound 1, particularly the sodium, hydrochloride, mesylate and tosylate salt forms.

In another embodiment, the invention comprises combinations of Compound 1 solid-state forms selected from the group consisting of the Form I polymorph, the Form II polymorph, the Form III polymorph, the solvated crystalline forms of Compound 1, the hydrated crystalline forms of Compound 1, the crystalline salt forms of Compound 1, and the amorphous form of Compound 1. Such combinations are useful, for example, in the preparation of pharmaceutical compositions having a variety of dissolution profiles, including controlled-release compositions. In one embodiment, a combination of solid-state forms is provided comprising the Form I polymorph in at least a detectable amount, with the balance being one or more solid-state forms selected from the group consisting of the Form II polymorph, the Form III polymorph, the solvated crystalline forms of Compound 1, the hydrated crystalline forms of Compound 1, the crystalline salt forms of Compound 1, and the amorphous form of Compound 1. In another embodiment, a combination of solid-state forms is provided comprising the Form II polymorph in at least a detectable amount, with the balance being one or more solid-state forms selected from the group consisting of the Form I polymorph, the Form III polymorph, the solvated crystalline forms of Compound 1, the hydrated crystalline forms of Compound 1, the crystalline salt forms of Compound 1, and the amorphous form of Compound 1. In another embodiment, a combination of solid-state forms is provided comprising the Form III polymorph in at least a detectable amount, with the balance being one or more solid-state forms selected from the group consisting of the Form I polymorph, the Form II polymorph, the solvated crystalline forms of Compound 1, the hydrated crystalline forms of Compound 1, the crystalline salt forms of Compound 1, and the amorphous form of Compound 1.

Depending upon the intended use of the solid-state form of Compound 1, processing considerations may favor selection of a specific solid-state form or a specific combination of such solid-state forms. The ease of preparing solid-state forms of Compound 1 (or solid-state forms of Compound 1 having a minimum phase purity) generally differs from one solid-state form to another. In addition, use of a solvated crystalline form of Compound 1 instead of the Form I polymorph or the Form II polymorph in a composition may eliminate a processing step, namely desolvation, for those processes that otherwise would proceed by desolvation of a solvated crystalline form. Alternatively, the desolvation step can be eliminated, for example, if the Form I polymorph is directly crystallized from an appropriate solvent without intervening preparation and desolvation of an intermediate solvated crystalline form. Such processes are described in greater detail below.

Indications

The solid-state forms of Compound 1 described in this application are useful for, but not limited to, the treatment of any condition in a human, or other mammal, which is exacerbated or caused by excessive or unregulated cytokine production by the mammal, such as TNF or p38 kinase production. These solid-state forms of Compound 1 are p38 kinase antagonists, directly or indirectly antagonize cytokines such as TNF and IL-1 proteins, and/or have the ability to retard the natural course of joint destruction in rheumatoid arthritis patients. Accordingly, the present invention provides a method of treating a cytokine-mediated condition, which comprises administering to a subject an effective cytokine-interfering amount of a solid-state form of Compound 1.

Solid-state forms of Compound 1 are useful for, but not limited to, the treatment or prophylaxis of:

(1) inflammation;
(2) arthritis including rheumatoid arthritis, spondyloarthropathies, gouty arthritis, osteoarthritis, systemic lupus erythematosus and juvenile arthritis, osteoarthritis, and other arthritic conditions;
(3) neuroinflammation;
(4) allergy, Th2 mediated diseases;
(5) pain (i.e., use as an analgesic) including but not limited to neuropathic pain;
(6) fever (i.e., use as an antipyretic);
(7) pulmonary disorders or lung inflammation, including adult respiratory distress syndrome, pulmonary sarcoidosis, asthma, silicosis, chronic pulmonary inflammatory disease, chronic obstructive pulmonary disease (COPD), and asthma;
(8) cardiovascular diseases including atherosclerosis, myocardial infarction (including post-myocardial infarction indications), thrombosis, congestive heart failure, and cardiac reperfusion injury, as well as complications associated with hypertension and/or heart failure such as vascular organ damage, restenosis;
(9) cardiomyopathy;
(10) stroke including ischemic and hemorrhagic stroke;
(11) ischemia including brain ischemia and ischemia resulting from cardiac/coronary bypass;
(12) reperfusion injury
(13) renal reperfusion injury;
(14) brain edema;
(15) neurotrauma and brain trauma including closed head injury;
(16) neurodegenerative disorders;
(17) central nervous system disorders (including, but not limited to, central nervous system disorders having an inflammatory or apoptotic component), such as Alzheimer's disease, Parkinson's disease, Huntington's Disease, amyotrophic lateral sclerosis, spinal cord injury, and peripheral neuropathy.
(18) liver disease and nephritis;
(19) gastrointestinal conditions such as inflammatory bowel disease, Crohn's disease, gastritis, irritable bowel syndrome and ulcerative colitis;
(20) ulcerative diseases such as gastric ulcer;
(21) periodontal disease
(22) ophthalmic diseases such as retinitis, retinopathies (including diabetic retinopathy), uveitis, ocular photophobia, nonglaucomatous optic nerve atrophy, and age related macular degeneration (ARMD) (including ARMD-atrophic form);
(23) ophthalmological conditions such as corneal graft rejection, ocular neovascularization, retinal neovascularization including neovascularization following injury or infection, and retrolental fibroplasia;
(24) glaucoma including primary open angle glaucoma (POAG), juvenile onset primary open-angle glaucoma, angle-closure glaucoma, pseudoexfoliative glaucoma, anterior ischemic optic neuropathy (AION), ocular hypertension, Reiger's syndrome, normal tension glaucoma, neovascular glaucoma, ocular inflammation and corticosteroid-induced glaucoma;
(25) acute injury to the eye tissue and ocular traumas such as post-traumatic glaucoma, traumatic optic neuropathy, and central retinal artery occlusion (CRAO);
(26) diabetes;
(27) diabetic nephropathy;
(28) skin-related conditions such as psoriasis, eczema, burns, dermatitis, keloid formation, scar tissue formation, and angiogenic disorders;

(29) viral and bacterial infections, including sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, and herpes virus;

(30) myalgias due to infection;

(31) influenza;

(32) endotoxic shock, sepsis;

(33) toxic shock syndrome;

(34) autoimmune disease including graft vs. host reaction and allograft rejections;

(35) treatment of bone resorption diseases, such as osteoporosis;

(36) multiple sclerosis;

(37) disorders of the female reproductive system such as endometriosis;

(38) pathological, but non-malignant, conditions such as hemaginomas, including infantile hemaginomas, angiofibroma of the nasopharynx and avascular necrosis of bone;

(39) benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovarian cancer, cervical cancer, lung cancer, breast cancer and skin cancer, such as squamus cell and basal cell cancers, prostate cancer, renal cell carcimoma, and other known cancers that affect epithelial cells throughout the body;

(40) leukemia;

(41) lymphoma;

(42) systemic lupus erthrematosis (SLE);

(43) angiogenesis including neoplasia; and

(44) metastasis.

The crystalline forms of Compound 1 disclosed in this application are also useful for preventing the production or expression of cyclooxygenase-2, or cyclooxygenase-2 activity.

Definitions

The term "amorphous" as applied to Compound 1 herein refers to a solid-state wherein the Compound 1 molecules are present in a disordered arrangement and do not form a distinguishable crystal lattice or unit cell. When subjected to X-ray powder diffraction, amorphous Compound 1 does not produce any characteristic crystalline peaks.

The term "crystalline form" as applied to Compound 1 herein refers to a solid-state form wherein the Compound 1 molecules are arranged to form a distinguishable crystal lattice (i) comprising distinguishable unit cells, and (ii) yielding diffraction peaks when subjected to X-ray radiation.

The term "crystallization" as used herein can refer to crystallization and/or recrystallization depending upon the applicable circumstances relating to preparation of Compound 1 starting material.

The term "direct crystallization" as used herein refers to crystallization of Compound 1 directly from a suitable solvent without formation and desolvation of an intermediate solvated crystalline solid-state form of Compound 1.

The term "Compound 1 drug substance" as used herein means Compound 1 per se as qualified by the context in which the term is used, and can refer to unformulated Compound 1 or to Compound 1 present as an ingredient of a pharmaceutical composition.

The term "particle size" as used herein refers to particle size as measured by conventional particle size measuring techniques well known in the art, such as laser light scattering, sedimentation field flow fractionation, photon correlation spectroscopy or disk centrifugation. One non-limiting example of a technique that can be used to measure particle size is a liquid dispersion technique employing a Sympatec Particle Size Analyzer. The "$D_{90}$ particle size" is a particle size such that 90% by weight of the particles are smaller than the $D_{90}$ particle size as measured by such conventional particle size measuring techniques.

The term "DSC" means differential scanning calorimetry.

The term "HPLC" means high pressure liquid chromatography.

The term "IR" means infrared.

The term "msec" means millisecond.

The term "purity" herein, unless otherwise qualified, means the chemical purity of Compound 1 according to conventional HPLC assay.

The term "phase purity" herein means the solid-state purity of Compound 1 with regard to a particular crystalline or amorphous form of the Compound 1 as determined by X-ray powder diffraction analytical methods described herein. The term "phase pure" refers to purity with respect to other solid-state forms of Compound 1 and does not necessarily imply a high degree of chemical purity with respect to other compounds.

The term "PXRD" means X-ray powder diffraction.

The term "TGA" means thermogravimetric analysis.

Characterization of Crystalline Form

1. Molecular Conformation

Single crystal X-ray analysis indicates that the molecular conformation differs for the various solid-state forms of Compound 1. For example, a difference in molecular conformation typically can be observed in the various crystalline forms of Compound 1 with respect to the orientations of one or more of the para-chloro-phenyl group, the pyrimidinyl group, and the 2-hydroxyacetyl-piperidinyl group attached to the core pyrazole ring.

2. X-Ray Diffraction

Single crystal X-ray analyses of the Form I polymorph and the dihydrate crystalline form of Compound 1 were conducted using a Siemens P4-UNIX diffractometer, using molybdenum Kα radiation (wavelength of 0.71073 Å) at temperatures of about 167° K for the Form I polymorph and about 173° K. for the dihydrate crystalline form. Single crystal X-ray analysis of the NMP solvate crystalline form of Compound 1 was conducted using a Bruker Smart 6KCCD X-ray detector diffractometer, using copper Kα radiation (wavelength of 1.54178 Å) at a temperature of about 120° K.

The Form I polymorph crystal was prepared by crystallization of Compound 1 from methanol. The dihydrate crystalline form crystal was prepared by crystallization of Compound 1 from tetrahydrofuran and water. The NMP solvate crystalline form crystal was prepared by crystallization of Compound 1 from N-methylpyrrolidone and ethanol.

The analyses showed that the Form I polymorph and the dihydrate crystalline form belong to the triclinic crystal system and P-1 (No. 2) space group, while the NMP solvate belongs to the monoclinic crystal system and $P2_1/c$ (No. 14) space group.

In addition, powder X-ray diffraction analyses of the crystalline forms of Compound 1 were conducted using a Siemens D5000 powder diffractometer. A sample of the crystalline form was placed in a sample holder and the raw data were measured for 2θ (two theta) values from 2 to 50 using copper Kα radiation (wavelength of 1.5405 Å), step scan 0.020 degrees, and step time two seconds. Tables 1–7 below disclose typical data for seven crystalline forms of Compound 1 in terms of the 2θ values and intensities obtained using powder X-ray diffraction analyses:

(1) Table 1 presents data obtained for a sample of the Form I polymorph;

(2) Table 2 presents data obtained for a sample of the Form II polymorph;

(3) Table 3 presents data obtained for a sample of the Form II polymorph;

(4) Table 4 presents data obtained for a sample of the acetic acid solvate;

(5) Table 5 presents data obtained for a sample of the NMP solvate;

(6) Table 6 presents data obtained for a sample of the monohydrate crystalline form;

(7) Table 7 presents data obtained for a sample of the dihydrate crystalline form; and (8) Table 8 presents data obtained for a sample of the crystalline sodium salt of Compound 1.

(9) Table 9 presents data obtained for a sample of the crystalline hydrochloride salt of Compound 1.

(10) Table 10 presents data obtained for a sample of the crystalline mesylate salt of Compound 1.

(11) Table 11 presents data obtained for a sample of the crystalline tosylate salt of Compound 1.

FIGS. 1–11 likewise set forth illustrative graphical X-ray powder diffraction profiles for Form I polymorph (FIG. 1), Form II polymorph (FIG. 2), Form III polymorph (FIG. 3), acetic acid solvate (FIG. 4), NMP solvate (FIG. 5), monohydrate crystalline form (FIG. 6), dihydrate crystalline form (FIG. 7), crystalline sodium salt of Compound 1 (FIG. 8), crystalline hydrochloride salt of Compound 1 (FIG. 9), crystalline mesylate salt of Compound 1 (FIG. 10), and crystalline tosylate salt of Compound 1 (FIG. 11) samples.

TABLE 1

X-Ray Diffraction Data (Form I)

| Angle (2-theta degrees) | d value (Å) | Intensity (counts) | Intensity (%) |
|---|---|---|---|
| 6.15 | 14.352 | 518 | 7.0 |
| 9.81 | 9.011 | 373 | 5.0 |
| 11.36 | 7.784 | 455 | 6.1 |
| 12.33 | 7.171 | 2069 | 27.8 |
| 13.93 | 6.351 | 545 | 7.3 |
| 14.38 | 6.153 | 282 | 3.8 |
| 14.93 | 5.929 | 1509 | 20.2 |
| 16.14 | 5.488 | 308 | 4.1 |
| 16.60 | 5.337 | 593 | 8.0 |
| 17.09 | 5.183 | 1365 | 18.3 |
| 17.36 | 5.104 | 345 | 4.6 |
| 17.76 | 4.990 | 180 | 2.4 |
| 18.57 | 4.775 | 958 | 12.9 |
| 19.02 | 4.662 | 675 | 9.1 |
| 19.24 | 4.609 | 1582 | 21.2 |
| 19.52 | 4.544 | 7452 | 100.0 |
| 20.14 | 4.406 | 611 | 8.2 |
| 20.94 | 4.239 | 1080 | 14.5 |
| 21.68 | 4.096 | 4839 | 64.9 |
| 22.55 | 3.940 | 1475 | 19.8 |
| 22.86 | 3.886 | 1954 | 26.2 |
| 23.44 | 3.792 | 200 | 2.7 |
| 23.77 | 3.741 | 583 | 7.8 |
| 24.88 | 3.576 | 1496 | 20.1 |
| 25.51 | 3.488 | 1328 | 17.8 |
| 25.88 | 3.440 | 716 | 9.6 |
| 26.18 | 3.401 | 755 | 10.1 |
| 26.65 | 3.342 | 1340 | 18.0 |
| 27.16 | 3.281 | 1251 | 16.8 |
| 27.63 | 3.226 | 402 | 5.4 |
| 27.99 | 3.185 | 315 | 4.2 |

TABLE 1-continued

X-Ray Diffraction Data (Form I)

| Angle (2-theta degrees) | d value (Å) | Intensity (counts) | Intensity (%) |
|---|---|---|---|
| 28.57 | 3.122 | 351 | 4.7 |
| 29.31 | 3.044 | 1692 | 22.7 |
| 29.76 | 3.000 | 418 | 5.6 |
| 30.15 | 2.962 | 676 | 9.1 |
| 30.59 | 2.920 | 447 | 6.0 |
| 30.89 | 2.893 | 485 | 6.5 |
| 31.24 | 2.861 | 375 | 5.0 |
| 31.42 | 2.845 | 511 | 6.9 |
| 31.96 | 2.798 | 250 | 3.4 |
| 32.67 | 2.739 | 655 | 8.8 |
| 33.39 | 2.682 | 430 | 5.8 |
| 33.71 | 2.657 | 251 | 3.4 |
| 34.29 | 2.613 | 272 | 3.7 |
| 34.55 | 2.594 | 308 | 4.1 |
| 35.21 | 2.546 | 544 | 7.3 |
| 35.45 | 2.530 | 517 | 6.9 |
| 35.93 | 2.497 | 278 | 3.7 |
| 36.42 | 2.465 | 303 | 4.1 |
| 37.13 | 2.419 | 350 | 4.7 |
| 37.34 | 2.407 | 337 | 4.5 |
| 38.44 | 2.340 | 187 | 2.5 |
| 39.32 | 2.290 | 178 | 2.4 |
| 39.70 | 2.269 | 306 | 4.1 |
| 40.02 | 2.251 | 232 | 3.1 |
| 41.00 | 2.199 | 232 | 3.1 |
| 42.03 | 2.148 | 227 | 3.0 |
| 42.79 | 2.111 | 272 | 3.7 |
| 43.74 | 2.068 | 397 | 5.3 |
| 44.30 | 2.043 | 425 | 5.7 |
| 45.23 | 2.003 | 243 | 3.3 |
| 45.75 | 1.982 | 457 | 6.1 |
| 46.60 | 1.947 | 234 | 3.1 |
| 47.24 | 1.923 | 320 | 4.3 |
| 48.16 | 1.888 | 243 | 3.3 |
| 48.31 | 1.883 | 263 | 3.5 |
| 49.29 | 1.847 | 139 | 1.9 |
| 49.78 | 1.830 | 181 | 2.4 |

TABLE 2

X-Ray Diffraction Data (Form II)

| Angle (2-theta degrees) | d value (Å) | Intensity (counts) | Intensity (%) |
|---|---|---|---|
| 4.74 | 18.631 | 1427 | 21.2 |
| 9.55 | 9.258 | 3843 | 57.1 |
| 12.20 | 7.249 | 599 | 8.9 |
| 13.05 | 6.778 | 667 | 9.9 |
| 14.48 | 6.113 | 2566 | 38.1 |
| 15.42 | 5.742 | 424 | 6.3 |
| 15.68 | 5.649 | 713 | 10.6 |
| 16.23 | 5.458 | 3913 | 58.1 |
| 16.94 | 5.230 | 2002 | 29.7 |
| 18.35 | 4.832 | 304 | 4.5 |
| 18.89 | 4.694 | 2558 | 38.0 |
| 19.27 | 4.602 | 2689 | 39.9 |
| 20.11 | 4.413 | 6308 | 93.7 |
| 20.98 | 4.231 | 212 | 3.1 |
| 21.51 | 4.128 | 1852 | 27.5 |
| 21.82 | 4.070 | 417 | 6.2 |
| 22.16 | 4.009 | 754 | 11.2 |
| 23.08 | 3.851 | 6732 | 100.0 |
| 23.70 | 3.752 | 685 | 10.2 |
| 24.16 | 3.680 | 361 | 5.4 |
| 24.63 | 3.611 | 395 | 5.9 |
| 25.12 | 3.542 | 614 | 9.1 |
| 25.46 | 3.495 | 528 | 7.8 |
| 26.16 | 3.404 | 773 | 11.5 |
| 26.70 | 3.336 | 1445 | 21.5 |
| 27.39 | 3.253 | 867 | 12.9 |

TABLE 2-continued

X-Ray Diffraction Data (Form II)

| Angle (2-theta degrees) | d value (Å) | Intensity (counts) | Intensity (%) |
|---|---|---|---|
| 27.92 | 3.193 | 745 | 11.1 |
| 28.47 | 3.132 | 262 | 3.9 |
| 29.11 | 3.065 | 1048 | 15.6 |
| 29.46 | 3.029 | 271 | 4.0 |
| 30.15 | 2.961 | 305 | 4.5 |
| 30.92 | 2.889 | 1301 | 19.3 |
| 31.86 | 2.806 | 288 | 4.3 |
| 32.55 | 2.748 | 508 | 7.5 |
| 33.01 | 2.711 | 879 | 13.1 |
| 33.57 | 2.667 | 304 | 4.5 |
| 34.06 | 2.630 | 697 | 10.4 |
| 34.31 | 2.611 | 1020 | 15.2 |
| 35.04 | 2.559 | 359 | 5.3 |
| 35.89 | 2.500 | 426 | 6.3 |
| 36.16 | 2.482 | 507 | 7.5 |
| 36.54 | 2.457 | 210 | 3.1 |
| 37.40 | 2.403 | 196 | 2.9 |
| 38.29 | 2.348 | 513 | 7.6 |
| 38.50 | 2.336 | 368 | 5.5 |
| 39.25 | 2.293 | 430 | 6.4 |
| 39.82 | 2.262 | 162 | 2.4 |
| 40.52 | 2.225 | 173 | 2.6 |
| 41.07 | 2.196 | 294 | 4.4 |
| 41.31 | 2.184 | 274 | 4.1 |
| 41.69 | 2.165 | 271 | 4.0 |
| 42.65 | 2.118 | 310 | 4.6 |
| 43.27 | 2.089 | 223 | 3.3 |
| 43.82 | 2.064 | 215 | 3.2 |
| 44.62 | 2.029 | 156 | 2.3 |
| 45.27 | 2.001 | 276 | 4.1 |
| 45.92 | 1.975 | 160 | 2.4 |
| 46.43 | 1.954 | 215 | 3.2 |
| 47.28 | 1.921 | 198 | 2.9 |
| 47.76 | 1.903 | 267 | 4.0 |
| 48.92 | 1.860 | 472 | 7.0 |
| 49.60 | 1.836 | 166 | 2.5 |

TABLE 3

X-Ray Diffraction Data (Form III)

| Angle (2-theta degrees) | d value (Å) | Intensity (counts) | Intensity (%) |
|---|---|---|---|
| 7.78 | 11.350 | 332 | 7.2 |
| 9.96 | 8.872 | 427 | 9.3 |
| 10.50 | 8.420 | 828 | 18.1 |
| 11.12 | 7.947 | 484 | 10.6 |
| 11.69 | 7.563 | 806 | 17.6 |
| 12.44 | 7.108 | 895 | 19.5 |
| 13.50 | 6.555 | 732 | 16.0 |
| 13.94 | 6.349 | 665 | 14.5 |
| 14.38 | 6.154 | 368 | 8.0 |
| 16.41 | 5.398 | 589 | 12.9 |
| 17.94 | 4.940 | 526 | 11.5 |
| 18.22 | 4.865 | 684 | 14.9 |
| 19.05 | 4.656 | 4580 | 100.0 |
| 19.61 | 4.523 | 786 | 17.2 |
| 20.55 | 4.319 | 2261 | 49.4 |
| 21.03 | 4.220 | 1707 | 37.3 |
| 21.73 | 4.086 | 2375 | 51.9 |
| 23.46 | 3.789 | 617 | 13.5 |
| 23.89 | 3.722 | 584 | 12.8 |
| 25.07 | 3.549 | 2483 | 54.2 |
| 26.19 | 3.400 | 598 | 13.1 |
| 26.95 | 3.305 | 686 | 15.0 |
| 27.28 | 3.266 | 605 | 13.2 |

TABLE 3-continued

X-Ray Diffraction Data (Form III)

| Angle (2-theta degrees) | d value (Å) | Intensity (counts) | Intensity (%) |
|---|---|---|---|
| 28.69 | 3.109 | 382 | 8.3 |
| 29.26 | 3.050 | 334 | 7.3 |
| 29.36 | 3.040 | 353 | 7.7 |
| 29.89 | 2.987 | 606 | 13.2 |
| 30.67 | 2.913 | 474 | 10.3 |
| 31.99 | 2.795 | 344 | 7.5 |
| 32.89 | 2.721 | 273 | 6.0 |
| 35.21 | 2.547 | 317 | 6.9 |
| 37.77 | 2.380 | 309 | 6.7 |
| 39.66 | 2.271 | 350 | 7.6 |
| 39.86 | 2.260 | 370 | 8.1 |
| 43.57 | 2.075 | 391 | 8.5 |
| 46.42 | 1.955 | 214 | 4.7 |
| 47.94 | 1.896 | 281 | 6.1 |
| 49.36 | 1.845 | 198 | 4.3 |

TABLE 4

X-Ray Diffraction Data (Acetic Acid Solvate)

| Angle (2-theta degrees) | d value (Å) | Intensity (counts) | Intensity (%) |
|---|---|---|---|
| 4.17 | 21.184 | 2561 | 100.0 |
| 8.30 | 10.638 | 1507 | 58.8 |
| 11.55 | 7.652 | 256 | 10.0 |
| 12.16 | 7.270 | 333 | 13.0 |
| 13.05 | 6.779 | 512 | 20.0 |
| 14.84 | 5.966 | 904 | 35.3 |
| 16.29 | 5.437 | 575 | 22.5 |
| 16.98 | 5.216 | 166 | 6.5 |
| 17.88 | 4.957 | 454 | 17.7 |
| 18.32 | 4.839 | 1581 | 61.7 |
| 19.25 | 4.606 | 947 | 37.0 |
| 20.15 | 4.404 | 885 | 34.6 |
| 20.65 | 4.298 | 1791 | 69.9 |
| 21.11 | 4.205 | 1912 | 74.7 |
| 22.08 | 4.022 | 939 | 36.7 |
| 22.73 | 3.909 | 671 | 26.2 |
| 24.65 | 3.609 | 978 | 38.2 |
| 25.00 | 3.559 | 627 | 24.5 |
| 25.45 | 3.497 | 587 | 22.9 |
| 26.70 | 3.336 | 698 | 27.3 |
| 27.76 | 3.211 | 361 | 14.1 |
| 28.43 | 3.137 | 542 | 21.2 |
| 29.30 | 3.046 | 779 | 30.4 |
| 29.77 | 2.998 | 202 | 7.9 |
| 30.81 | 2.900 | 488 | 19.1 |
| 32.10 | 2.786 | 439 | 17.1 |
| 32.47 | 2.755 | 425 | 16.6 |
| 33.23 | 2.694 | 356 | 13.9 |
| 33.72 | 2.656 | 530 | 20.7 |
| 34.33 | 2.610 | 414 | 16.2 |
| 35.16 | 2.550 | 360 | 14.1 |
| 35.44 | 2.531 | 363 | 14.2 |
| 36.09 | 2.486 | 321 | 12.5 |
| 38.14 | 2.358 | 318 | 12.4 |
| 38.53 | 2.335 | 281 | 11.0 |
| 39.43 | 2.283 | 270 | 10.5 |
| 42.99 | 2.102 | 196 | 7.7 |
| 43.55 | 2.076 | 161 | 6.3 |
| 47.58 | 1.910 | 258 | 10.1 |
| 47.72 | 1.904 | 241 | 9.4 |
| 49.29 | 1.847 | 296 | 11.6 |

TABLE 5

X-Ray Diffraction Data (NMP Solvate)

| Angle (2-theta degrees) | d value (Å) | Intensity (counts) | Intensity (%) |
| --- | --- | --- | --- |
| 8.00 | 11.041 | 1134 | 22.9 |
| 9.18 | 9.630 | 212 | 4.3 |
| 10.32 | 8.566 | 948 | 19.2 |
| 12.11 | 7.301 | 762 | 15.4 |
| 12.38 | 7.143 | 704 | 14.2 |
| 15.34 | 5.771 | 1272 | 25.7 |
| 15.75 | 5.622 | 1914 | 38.7 |
| 16.46 | 5.382 | 826 | 16.7 |
| 18.23 | 4.863 | 934 | 18.9 |
| 18.92 | 4.686 | 2758 | 55.7 |
| 19.36 | 4.580 | 1770 | 35.8 |
| 20.38 | 4.354 | 4950 | 100.0 |
| 21.11 | 4.205 | 1511 | 30.5 |
| 22.00 | 4.036 | 2324 | 46.9 |
| 22.43 | 3.961 | 1725 | 34.8 |
| 23.08 | 3.850 | 1437 | 29.0 |
| 23.84 | 3.729 | 538 | 10.9 |
| 24.45 | 3.637 | 1331 | 26.9 |
| 24.78 | 3.591 | 1959 | 39.6 |
| 25.09 | 3.547 | 1120 | 22.6 |
| 25.64 | 3.472 | 2581 | 52.1 |
| 26.35 | 3.379 | 1170 | 23.6 |
| 26.81 | 3.323 | 908 | 18.3 |
| 27.68 | 3.220 | 1277 | 25.8 |
| 27.91 | 3.194 | 1964 | 39.7 |
| 28.85 | 3.092 | 471 | 9.5 |
| 29.22 | 3.054 | 421 | 8.5 |
| 29.80 | 2.996 | 457 | 9.2 |
| 30.44 | 2.934 | 509 | 10.3 |
| 30.68 | 2.912 | 668 | 13.5 |
| 31.20 | 2.865 | 544 | 11.0 |
| 31.75 | 2.816 | 382 | 7.7 |
| 32.63 | 2.742 | 676 | 13.7 |
| 32.94 | 2.717 | 485 | 9.8 |
| 33.94 | 2.639 | 299 | 6.0 |
| 34.20 | 2.620 | 261 | 5.3 |
| 34.95 | 2.565 | 311 | 6.3 |
| 35.78 | 2.507 | 270 | 5.5 |
| 36.38 | 2.468 | 292 | 5.9 |
| 36.66 | 2.450 | 326 | 6.6 |
| 37.08 | 2.422 | 328 | 6.6 |
| 37.85 | 2.375 | 544 | 11.0 |
| 39.32 | 2.289 | 491 | 9.9 |
| 39.50 | 2.279 | 417 | 8.4 |
| 40.25 | 2.239 | 459 | 9.3 |
| 40.69 | 2.215 | 357 | 7.2 |
| 41.49 | 2.174 | 264 | 5.3 |
| 42.90 | 2.106 | 355 | 7.2 |
| 43.23 | 2.091 | 499 | 10.1 |
| 44.38 | 2.040 | 345 | 7.0 |
| 45.51 | 1.992 | 266 | 5.4 |
| 46.71 | 1.943 | 358 | 7.2 |
| 47.55 | 1.911 | 436 | 8.8 |
| 47.93 | 1.897 | 469 | 9.5 |

TABLE 6

X-Ray Diffraction Data (Monohydrate)

| Angle (2-theta degrees) | d value (Å) | Intensity (counts) | Intensity (%) |
| --- | --- | --- | --- |
| 8.36 | 10.563 | 1901 | 20.1 |
| 9.48 | 9.320 | 282 | 3.0 |
| 11.17 | 7.912 | 1007 | 10.7 |
| 12.53 | 7.058 | 610 | 6.5 |
| 12.92 | 6.846 | 1686 | 17.9 |
| 13.75 | 6.436 | 366 | 3.9 |
| 14.58 | 6.071 | 619 | 6.6 |
| 15.65 | 5.659 | 228 | 2.4 |
| 15.96 | 5.550 | 359 | 3.8 |
| 16.80 | 5.273 | 411 | 4.4 |
| 17.05 | 5.195 | 896 | 9.5 |
| 18.27 | 4.853 | 681 | 7.2 |
| 18.82 | 4.712 | 4383 | 46.4 |
| 19.20 | 4.618 | 9439 | 100.0 |
| 20.05 | 4.425 | 3435 | 36.4 |
| 20.68 | 4.291 | 5858 | 62.1 |
| 21.36 | 4.156 | 525 | 5.6 |
| 21.89 | 4.057 | 773 | 8.2 |
| 22.16 | 4.008 | 1548 | 16.4 |
| 22.54 | 3.941 | 1928 | 20.4 |
| 22.84 | 3.890 | 1691 | 17.9 |
| 23.62 | 3.764 | 423 | 4.5 |
| 24.45 | 3.637 | 339 | 3.6 |
| 24.91 | 3.571 | 3802 | 40.3 |
| 25.67 | 3.467 | 1553 | 16.5 |
| 26.07 | 3.416 | 1384 | 14.7 |
| 26.34 | 3.381 | 1795 | 19.0 |
| 27.69 | 3.219 | 1060 | 11.2 |
| 28.10 | 3.172 | 634 | 6.7 |
| 28.34 | 3.146 | 1060 | 11.2 |
| 28.91 | 3.086 | 581 | 6.2 |
| 29.19 | 3.057 | 479 | 5.1 |
| 29.61 | 3.015 | 471 | 5.0 |
| 30.14 | 2.962 | 511 | 5.4 |
| 30.49 | 2.929 | 1229 | 13.0 |
| 30.94 | 2.888 | 368 | 3.9 |
| 31.22 | 2.862 | 500 | 5.3 |
| 31.95 | 2.799 | 431 | 4.6 |
| 32.60 | 2.745 | 274 | 2.9 |
| 33.00 | 2.712 | 566 | 6.0 |
| 33.45 | 2.676 | 340 | 3.6 |
| 33.93 | 2.640 | 834 | 8.8 |
| 35.12 | 2.553 | 421 | 4.5 |
| 35.35 | 2.537 | 365 | 3.9 |
| 36.11 | 2.485 | 224 | 2.4 |
| 37.10 | 2.421 | 258 | 2.7 |
| 37.61 | 2.390 | 270 | 2.9 |
| 38.30 | 2.348 | 292 | 3.1 |
| 39.15 | 2.299 | 596 | 6.3 |
| 39.46 | 2.282 | 514 | 5.4 |
| 40.27 | 2.238 | 449 | 4.8 |
| 40.81 | 2.209 | 603 | 6.4 |
| 41.64 | 2.167 | 366 | 3.9 |
| 42.89 | 2.107 | 370 | 3.9 |
| 43.54 | 2.077 | 292 | 3.1 |
| 44.11 | 2.051 | 370 | 3.9 |
| 44.81 | 2.021 | 244 | 2.6 |
| 45.59 | 1.988 | 379 | 4.0 |
| 46.65 | 1.945 | 415 | 4.4 |
| 47.46 | 1.914 | 350 | 3.7 |
| 47.85 | 1.899 | 302 | 3.2 |
| 48.48 | 1.876 | 316 | 3.3 |
| 48.97 | 1.858 | 316 | 3.3 |

TABLE 7

X-Ray Diffraction Data (Dihydrate)

| Angle (2-theta degrees) | d value (Å) | Intensity (counts) | Intensity (%) |
| --- | --- | --- | --- |
| 7.21 | 12.247 | 2724 | 51.7 |
| 10.42 | 8.483 | 1325 | 25.1 |
| 10.89 | 8.121 | 789 | 15.0 |
| 12.32 | 7.178 | 441 | 8.4 |
| 13.26 | 6.672 | 713 | 13.5 |
| 14.46 | 6.122 | 4623 | 87.7 |
| 15.28 | 5.793 | 371 | 7.0 |
| 15.56 | 5.691 | 959 | 18.2 |
| 17.95 | 4.938 | 818 | 15.5 |

TABLE 7-continued

X-Ray Diffraction Data (Dihydrate)

| Angle (2-theta degrees) | d value (Å) | Intensity (counts) | Intensity (%) |
|---|---|---|---|
| 18.21 | 4.869 | 931 | 17.7 |
| 18.77 | 4.723 | 1557 | 29.5 |
| 19.11 | 4.641 | 1751 | 33.2 |
| 19.38 | 4.576 | 658 | 12.5 |
| 20.14 | 4.405 | 5272 | 100.0 |
| 20.97 | 4.232 | 624 | 11.8 |
| 21.34 | 4.161 | 692 | 13.1 |
| 21.89 | 4.058 | 2085 | 39.5 |
| 22.41 | 3.965 | 478 | 9.1 |
| 22.89 | 3.882 | 338 | 6.4 |
| 23.54 | 3.777 | 3166 | 60.1 |
| 23.84 | 3.729 | 564 | 10.7 |
| 24.09 | 3.692 | 372 | 7.1 |
| 24.57 | 3.620 | 270 | 5.1 |
| 25.15 | 3.539 | 1031 | 19.6 |
| 25.57 | 3.480 | 2938 | 55.7 |
| 26.79 | 3.325 | 3663 | 69.5 |
| 27.02 | 3.297 | 1734 | 32.9 |
| 27.66 | 3.222 | 597 | 11.3 |
| 28.05 | 3.178 | 826 | 15.7 |
| 28.69 | 3.109 | 1252 | 23.7 |
| 29.70 | 3.005 | 677 | 12.8 |
| 30.00 | 2.976 | 596 | 11.3 |
| 30.20 | 2.957 | 472 | 9.0 |
| 30.82 | 2.899 | 502 | 9.5 |
| 31.04 | 2.879 | 474 | 9.0 |
| 31.59 | 2.830 | 271 | 5.1 |
| 32.30 | 2.769 | 528 | 10.0 |
| 32.55 | 2.748 | 783 | 14.9 |
| 32.89 | 2.721 | 416 | 7.9 |
| 33.34 | 2.685 | 488 | 9.3 |
| 33.84 | 2.647 | 216 | 4.1 |
| 34.59 | 2.591 | 367 | 7.0 |
| 35.28 | 2.542 | 220 | 4.2 |
| 35.56 | 2.522 | 323 | 6.1 |
| 35.89 | 2.500 | 304 | 5.8 |
| 36.16 | 2.482 | 401 | 7.6 |
| 36.74 | 2.444 | 650 | 12.3 |
| 37.15 | 2.418 | 341 | 6.5 |
| 37.99 | 2.367 | 423 | 8.0 |
| 38.44 | 2.340 | 348 | 6.6 |
| 39.22 | 2.295 | 428 | 8.1 |
| 39.53 | 2.278 | 939 | 17.8 |
| 40.43 | 2.229 | 367 | 7.0 |
| 41.07 | 2.196 | 302 | 5.7 |
| 41.14 | 2.192 | 250 | 4.7 |
| 41.26 | 2.186 | 289 | 5.5 |
| 42.26 | 2.137 | 603 | 11.4 |
| 42.66 | 2.118 | 344 | 6.5 |
| 43.10 | 2.097 | 335 | 6.4 |
| 43.44 | 2.081 | 518 | 9.8 |
| 44.15 | 2.050 | 506 | 9.6 |
| 45.15 | 2.006 | 1009 | 19.1 |
| 45.64 | 1.986 | 314 | 6.0 |
| 46.36 | 1.957 | 254 | 4.8 |
| 47.00 | 1.932 | 803 | 15.2 |
| 47.74 | 1.904 | 744 | 14.1 |
| 49.62 | 1.836 | 298 | 5.7 |

TABLE 8

X-Ray Diffraction Data (Sodium Salt)

| Angle (2-theta degrees) | d value (Å) | Intensity (counts) | Intensity (%) |
|---|---|---|---|
| 5.68 | 15.551 | 328 | 11.8 |
| 6.16 | 14.327 | 311 | 11.1 |
| 7.81 | 11.313 | 249 | 8.9 |
| 9.83 | 8.988 | 307 | 11.0 |
| 11.40 | 7.759 | 1433 | 51.4 |

TABLE 8-continued

X-Ray Diffraction Data (Sodium Salt)

| Angle (2-theta degrees) | d value (Å) | Intensity (counts) | Intensity (%) |
|---|---|---|---|
| 12.36 | 7.156 | 1009 | 36.2 |
| 12.94 | 6.836 | 427 | 15.3 |
| 13.96 | 6.338 | 387 | 13.9 |
| 14.95 | 5.921 | 471 | 16.9 |
| 15.76 | 5.618 | 384 | 13.8 |
| 16.24 | 5.455 | 674 | 24.2 |
| 16.63 | 5.328 | 646 | 23.2 |
| 17.09 | 5.184 | 769 | 27.6 |
| 18.60 | 4.765 | 1207 | 43.3 |
| 18.89 | 4.694 | 1392 | 49.9 |
| 19.28 | 4.600 | 1304 | 46.7 |
| 19.55 | 4.537 | 2619 | 93.9 |
| 20.08 | 4.418 | 1181 | 42.3 |
| 20.98 | 4.230 | 822 | 29.5 |
| 21.74 | 4.085 | 2790 | 100.0 |
| 22.58 | 3.935 | 1067 | 38.2 |
| 22.90 | 3.881 | 2552 | 91.5 |
| 23.85 | 3.727 | 818 | 29.3 |
| 24.41 | 3.644 | 2611 | 93.6 |
| 24.90 | 3.572 | 1102 | 39.5 |
| 25.57 | 3.481 | 1081 | 38.7 |
| 25.93 | 3.433 | 943 | 33.8 |
| 26.18 | 3.401 | 808 | 29.0 |
| 26.68 | 3.339 | 784 | 28.1 |
| 27.21 | 3.275 | 843 | 30.2 |
| 27.46 | 3.246 | 725 | 26.0 |
| 29.33 | 3.043 | 749 | 26.8 |
| 29.83 | 2.993 | 533 | 19.1 |
| 30.18 | 2.959 | 579 | 20.8 |
| 30.93 | 2.889 | 436 | 15.6 |
| 31.47 | 2.840 | 411 | 14.7 |
| 31.85 | 2.807 | 314 | 11.3 |
| 32.71 | 2.735 | 479 | 17.2 |
| 33.40 | 2.680 | 462 | 16.6 |
| 34.31 | 2.611 | 350 | 12.5 |
| 34.52 | 2.596 | 393 | 14.1 |
| 35.36 | 2.537 | 419 | 15.0 |
| 36.47 | 2.461 | 297 | 10.6 |
| 37.28 | 2.410 | 317 | 11.4 |
| 39.79 | 2.263 | 442 | 15.8 |
| 42.18 | 2.141 | 392 | 14.1 |
| 43.76 | 2.067 | 377 | 13.5 |
| 44.34 | 2.041 | 371 | 13.3 |
| 45.78 | 1.980 | 329 | 11.8 |
| 47.36 | 1.918 | 303 | 10.9 |

TABLE 9

X-Ray Diffraction Data (Hydrochloride Salt)

| Angle (2-theta degrees) | d value (Å) | Intensity (counts) | Intensity (%) |
|---|---|---|---|
| 4.42 | 19.975 | 291 | 4.8 |
| 7.45 | 11.861 | 464 | 7.7 |
| 9.97 | 8.864 | 949 | 15.7 |
| 10.26 | 8.612 | 417 | 6.9 |
| 10.74 | 8.227 | 378 | 6.3 |
| 12.63 | 7.001 | 1185 | 19.6 |
| 14.30 | 6.188 | 414 | 6.9 |
| 14.59 | 6.067 | 1001 | 16.6 |
| 15.07 | 5.874 | 896 | 14.8 |
| 15.38 | 5.756 | 161 | 2.7 |
| 16.38 | 5.408 | 190 | 3.1 |
| 19.88 | 4.462 | 6039 | 100.0 |
| 20.59 | 4.310 | 3585 | 59.4 |
| 20.78 | 4.272 | 3256 | 53.9 |
| 21.10 | 4.207 | 651 | 10.8 |
| 21.72 | 4.088 | 451 | 7.5 |
| 22.40 | 3.965 | 2508 | 41.5 |
| 22.89 | 3.882 | 1046 | 17.3 |

TABLE 9-continued

X-Ray Diffraction Data (Hydrochloride Salt)

| Angle (2-theta degrees) | d value (Å) | Intensity (counts) | Intensity (%) |
|---|---|---|---|
| 23.30 | 3.814 | 4138 | 68.5 |
| 23.69 | 3.752 | 1152 | 19.1 |
| 24.28 | 3.663 | 427 | 7.1 |
| 24.54 | 3.625 | 939 | 15.5 |
| 24.95 | 3.566 | 798 | 13.2 |
| 25.39 | 3.505 | 251 | 4.2 |
| 26.04 | 3.419 | 355 | 5.9 |
| 26.53 | 3.357 | 408 | 6.8 |
| 26.80 | 3.324 | 201 | 3.3 |
| 27.20 | 3.276 | 245 | 4.1 |
| 27.42 | 3.250 | 409 | 6.8 |
| 28.19 | 3.162 | 1136 | 18.8 |
| 28.76 | 3.101 | 1524 | 25.2 |
| 29.40 | 3.036 | 558 | 9.2 |
| 30.03 | 2.973 | 479 | 7.9 |
| 30.31 | 2.947 | 533 | 8.8 |
| 30.78 | 2.902 | 362 | 6.0 |
| 31.08 | 2.876 | 228 | 3.8 |
| 31.55 | 2.833 | 253 | 4.2 |
| 31.80 | 2.812 | 245 | 4.1 |
| 32.32 | 2.768 | 409 | 6.8 |
| 32.69 | 2.737 | 466 | 7.7 |
| 33.13 | 2.702 | 455 | 7.5 |
| 33.68 | 2.659 | 284 | 4.7 |
| 33.98 | 2.636 | 406 | 6.7 |
| 34.15 | 2.623 | 594 | 9.8 |
| 34.87 | 2.571 | 307 | 5.1 |
| 35.26 | 2.543 | 419 | 6.9 |
| 35.87 | 2.501 | 405 | 6.7 |
| 36.60 | 2.453 | 305 | 5.1 |
| 37.19 | 2.416 | 227 | 3.8 |
| 37.64 | 2.388 | 238 | 3.9 |
| 37.87 | 2.374 | 202 | 3.3 |
| 38.47 | 2.338 | 524 | 8.7 |
| 39.76 | 2.265 | 304 | 5.0 |
| 40.44 | 2.229 | 265 | 4.4 |
| 40.85 | 2.207 | 331 | 5.5 |
| 41.22 | 2.188 | 353 | 5.8 |
| 41.73 | 2.163 | 390 | 6.5 |
| 42.38 | 2.131 | 324 | 5.4 |
| 43.13 | 2.095 | 238 | 3.9 |
| 43.88 | 2.062 | 287 | 4.8 |
| 44.65 | 2.028 | 269 | 4.5 |
| 45.78 | 1.980 | 173 | 2.9 |
| 47.22 | 1.923 | 265 | 4.4 |
| 47.58 | 1.910 | 437 | 7.2 |

TABLE 10

X-Ray Diffraction Data (Mesylate Salt)

| Angle (2-theta degrees) | d value (Å) | Intensity (counts) | Intensity (%) |
|---|---|---|---|
| 7.50 | 11.770 | 285 | 6.7 |
| 8.83 | 10.010 | 382 | 8.9 |
| 10.72 | 8.242 | 559 | 13.1 |
| 12.60 | 7.018 | 426 | 10.0 |
| 14.95 | 5.922 | 464 | 10.8 |
| 15.16 | 5.840 | 493 | 11.5 |
| 16.54 | 5.356 | 291 | 6.8 |
| 16.96 | 5.222 | 1105 | 25.8 |
| 17.61 | 5.033 | 2251 | 52.6 |
| 18.07 | 4.905 | 823 | 19.2 |
| 18.40 | 4.817 | 2144 | 50.1 |
| 18.86 | 4.700 | 2803 | 65.5 |
| 19.78 | 4.484 | 782 | 18.3 |
| 20.17 | 4.398 | 304 | 7.1 |
| 20.99 | 4.229 | 4280 | 100.0 |
| 22.19 | 4.003 | 2680 | 62.6 |
| 22.40 | 3.966 | 1708 | 39.9 |
| 22.68 | 3.917 | 605 | 14.1 |
| 23.02 | 3.860 | 810 | 18.9 |
| 23.35 | 3.807 | 946 | 22.1 |
| 23.80 | 3.735 | 2027 | 47.4 |
| 24.60 | 3.616 | 688 | 16.1 |
| 24.79 | 3.588 | 1105 | 25.8 |
| 25.22 | 3.528 | 392 | 9.2 |
| 25.53 | 3.487 | 268 | 6.3 |
| 25.89 | 3.439 | 194 | 4.5 |
| 26.47 | 3.365 | 702 | 16.4 |
| 26.74 | 3.331 | 471 | 11.0 |
| 27.10 | 3.287 | 583 | 13.6 |
| 27.74 | 3.213 | 538 | 12.6 |
| 28.13 | 3.169 | 768 | 17.9 |
| 29.32 | 3.044 | 294 | 6.9 |
| 29.60 | 3.016 | 482 | 11.3 |
| 30.18 | 2.959 | 934 | 21.8 |
| 30.71 | 2.909 | 541 | 12.6 |
| 30.98 | 2.884 | 520 | 12.1 |
| 31.43 | 2.844 | 258 | 6.0 |
| 31.94 | 2.800 | 194 | 4.5 |
| 32.48 | 2.754 | 322 | 7.5 |
| 32.62 | 2.743 | 360 | 8.4 |
| 32.93 | 2.718 | 371 | 8.7 |
| 33.36 | 2.683 | 770 | 18.0 |
| 33.80 | 2.650 | 230 | 5.4 |
| 34.36 | 2.608 | 200 | 4.7 |
| 34.98 | 2.563 | 242 | 5.7 |
| 35.16 | 2.550 | 269 | 6.3 |
| 35.77 | 2.508 | 410 | 9.6 |
| 36.59 | 2.454 | 474 | 11.1 |
| 37.14 | 2.419 | 428 | 10.0 |
| 37.54 | 2.394 | 338 | 7.9 |
| 38.27 | 2.350 | 325 | 7.6 |
| 38.70 | 2.325 | 235 | 5.5 |
| 39.10 | 2.302 | 193 | 4.5 |
| 39.56 | 2.276 | 202 | 4.7 |
| 40.10 | 2.247 | 297 | 6.9 |
| 40.77 | 2.211 | 243 | 5.7 |
| 41.22 | 2.188 | 249 | 5.8 |
| 41.53 | 2.173 | 253 | 5.9 |
| 42.09 | 2.145 | 287 | 6.7 |
| 43.48 | 2.080 | 252 | 5.9 |
| 44.42 | 2.038 | 289 | 6.8 |
| 45.04 | 2.011 | 245 | 5.7 |
| 45.58 | 1.988 | 410 | 9.6 |
| 46.65 | 1.945 | 226 | 5.3 |
| 47.01 | 1.931 | 234 | 5.5 |
| 47.90 | 1.898 | 221 | 5.2 |
| 48.66 | 1.870 | 177 | 4.1 |
| 49.66 | 1.834 | 185 | 4.3 |

TABLE 11

X-Ray Diffraction Data (Tosylate Salt)

| Angle (2-theta degrees) | d value (Å) | Intensity (counts) | Intensity (%) |
|---|---|---|---|
| 4.86 | 18.169 | 431 | 5.5 |
| 8.15 | 10.844 | 522 | 6.7 |
| 9.29 | 9.514 | 397 | 5.1 |
| 9.70 | 9.113 | 684 | 8.7 |
| 12.35 | 7.162 | 279 | 3.6 |
| 13.00 | 6.805 | 576 | 7.3 |
| 13.90 | 6.366 | 582 | 7.4 |
| 14.16 | 6.251 | 636 | 8.1 |
| 14.58 | 6.071 | 2243 | 28.6 |
| 15.42 | 5.742 | 136 | 1.7 |
| 16.41 | 5.398 | 2295 | 29.3 |
| 17.26 | 5.135 | 199 | 2.5 |

TABLE 11-continued

X-Ray Diffraction Data (Tosylate Salt)

| Angle (2-theta degrees) | d value (Å) | Intensity (counts) | Intensity (%) |
| --- | --- | --- | --- |
| 17.50 | 5.062 | 285 | 3.6 |
| 17.90 | 4.952 | 1013 | 12.9 |
| 18.36 | 4.828 | 1313 | 16.7 |
| 18.70 | 4.742 | 7841 | 100.0 |
| 19.40 | 4.571 | 2445 | 31.2 |
| 20.11 | 4.412 | 194 | 2.5 |
| 20.71 | 4.286 | 1560 | 19.9 |
| 21.34 | 4.161 | 2044 | 26.1 |
| 21.73 | 4.086 | 1368 | 17.4 |
| 22.47 | 3.953 | 2691 | 34.3 |
| 22.76 | 3.904 | 407 | 5.2 |
| 23.20 | 3.830 | 2328 | 29.7 |
| 23.44 | 3.792 | 938 | 12.0 |
| 24.10 | 3.690 | 746 | 9.5 |
| 24.60 | 3.616 | 766 | 9.8 |
| 24.86 | 3.578 | 1648 | 21.0 |
| 25.32 | 3.514 | 683 | 8.7 |
| 26.07 | 3.415 | 1816 | 23.2 |
| 26.89 | 3.313 | 921 | 11.7 |
| 27.58 | 3.232 | 1481 | 18.9 |
| 28.02 | 3.182 | 971 | 12.4 |
| 28.24 | 3.157 | 575 | 7.3 |
| 28.71 | 3.107 | 445 | 5.7 |
| 29.01 | 3.076 | 581 | 7.4 |
| 29.31 | 3.045 | 875 | 11.2 |
| 30.08 | 2.969 | 478 | 6.1 |
| 30.72 | 2.908 | 751 | 9.6 |
| 31.08 | 2.875 | 393 | 5.0 |
| 31.80 | 2.812 | 363 | 4.6 |
| 32.14 | 2.783 | 773 | 9.9 |
| 33.00 | 2.712 | 587 | 7.5 |
| 33.40 | 2.680 | 239 | 3.0 |
| 33.92 | 2.640 | 511 | 6.5 |
| 34.48 | 2.599 | 949 | 12.1 |
| 35.03 | 2.560 | 234 | 3.0 |
| 35.47 | 2.529 | 388 | 4.9 |
| 35.78 | 2.507 | 212 | 2.7 |
| 36.57 | 2.455 | 450 | 5.7 |
| 37.12 | 2.420 | 262 | 3.3 |
| 37.37 | 2.404 | 379 | 4.8 |
| 38.22 | 2.353 | 408 | 5.2 |
| 38.64 | 2.328 | 317 | 4.0 |
| 39.41 | 2.284 | 227 | 2.9 |
| 39.91 | 2.257 | 187 | 2.4 |
| 40.30 | 2.236 | 254 | 3.2 |
| 40.59 | 2.221 | 319 | 4.1 |
| 41.20 | 2.189 | 212 | 2.7 |
| 41.84 | 2.157 | 198 | 2.5 |
| 42.28 | 2.136 | 261 | 3.3 |
| 43.33 | 2.087 | 345 | 4.4 |
| 44.69 | 2.026 | 355 | 4.5 |
| 45.11 | 2.008 | 265 | 3.4 |
| 45.90 | 1.976 | 293 | 3.7 |
| 46.91 | 1.935 | 226 | 2.9 |
| 47.81 | 1.901 | 195 | 2.5 |
| 48.39 | 1.880 | 235 | 3.0 |
| 48.81 | 1.864 | 243 | 3.1 |
| 49.65 | 1.835 | 189 | 2.4 |

The Form I polymorph typically has an X-ray powder diffraction pattern comprising at least one peak selected from the group consisting of 6.2±0.2, 12.3±0.2, 14.9±0.2, 17.1±0.2, and 19.5±0.2 degrees 2θ. In one embodiment of the invention, the solid-state form of Compound 1 is the Form I polymorph having an X-ray powder diffraction pattern comprising a peak at 6.2±0.2 degrees 2θ.

The Form II polymorph typically has an X-ray powder diffraction pattern comprising at least one peak selected from the group consisting of 4.7±0.2, 9.6±0.2, 14.5±0.2, 16.2±0.2 and 20.1±0.2 degrees 2θ. In one embodiment of the invention, the solid-state form of Compound 1 is the Form II polymorph having an X-ray powder diffraction pattern comprising a peak at 4.7±0.2 degrees 2θ.

The Form III polymorph typically has an X-ray powder diffraction pattern comprising at least one peak selected from the group consisting of 10.5±0.2, 11.7±0.2, 12.4±0.2 and 19.1±0.2 degrees 2θ. In one embodiment of the invention, the solid-state form of Compound 1 is the Form III polymorph having an X-ray powder diffraction pattern comprising a peak at 10.5±0.2 degrees 2θ.

The acetic acid solvate typically has an X-ray powder diffraction pattern comprising at least one peak selected from the group consisting of 4.2±0.2, 8.3±0.2, and 18.3±0.2 degrees 2θ. In one embodiment of the invention, the solid-state form of Compound 1 is the acetic acid solvate having an X-ray powder diffraction pattern comprising a peak at 4.2±0.2 degrees 2θ.

The NMP solvate typically has an X-ray powder diffraction pattern comprising at least one peak selected from the group consisting of 8.0±0.2, 10.3±0.2, 15.3±0.2, 15.8±0.2, and 20.4±0.2 degrees 2θ. In one embodiment of the invention, the solid-state form of Compound 1 is the NMP solvate having an X-ray powder diffraction pattern comprising peaks at 8.0±0.2 degrees 2θ and 15.3±0.2 degrees 2θ.

The monohydrate crystalline form typically has an X-ray powder diffraction pattern comprising at least one peak selected from the group consisting of 8.4±0.2, 11.2±0.2, 12.9±0.2, 18.8±0.2, and 19.2±0.2 degrees 2θ. In one embodiment of the invention, the solid-state form of Compound 1 is the monohydrate crystalline form having an X-ray powder diffraction pattern comprising a peak at 8.4±0.2 degrees 2θ.

The dihydrate crystalline form typically has an X-ray powder diffraction pattern comprising at least one peak selected from the group consisting of 7.2±0.2, 10.4±0.2 and 14.5±0.2 degrees 2θ. In one embodiment of the invention, the solid-state form of Compound 1 is the dihydrate crystalline form having an X-ray powder diffraction pattern comprising a peak at 7.2±0.2 degrees 2θ.

The sodium salt typically has an X-ray powder diffraction pattern comprising at least one peak selected from the group consisting of 5.7±0.2, 6.2±0.2, 11.4±0.2, 12.4±0.2, 20.1±0.2, 21.8±0.2, and 22.9±0.2 degrees 2θ. In embodiment of the invention, the solid-state form of Compound 1 is the sodium salt having an X-ray powder diffraction pattern comprising peaks at 5.7±0.2 and 6.2±0.2 degrees 2θ.

The hydrochloride salt typically has an X-ray powder diffraction pattern comprising at least one peak selected from the group consisting of 7.5±0.2, 10.0±0.2, 12.6±0.2, 14.5±0.2, 15.1±0.2, and 19.9±0.2 degrees 2θ. In one embodiment of the invention, the solid-state form of Compound 1 is the hydrochloride salt having an X-ray powder diffraction pattern comprising peaks at 7.5±0.2 degrees 2θ and 15.1±0.2 degrees 2θ.

The mesylate salt typically has an X-ray powder diffraction pattern comprising at least one peak selected from the group consisting of 8.8±0.2, 10.7±0.2, 17.6±0.2, 18.9±0.2, 21.0±0.2, and 22.2±0.2 degrees 2θ. In one embodiment of the invention, the solid-state form of Compound 1 is the mesylate salt having an X-ray powder diffraction pattern comprising a peak at 8.8±0.2 degrees 2θ.

The tosylate salt typically has an X-ray powder diffraction pattern comprising at least one peak selected from the group consisting of 4.9±0.2, 8.2±0.2, 9.7±0.2, 14.6±0.2, 16.4±0.2 and 18.7±0.2 degrees 2θ. In one embodiment of the invention, the solid-state form of Compound 1 is the tosylate salt having an X-ray powder diffraction pattern comprising peaks at 4.9±0.2 degrees 2θ and 8.2±0.2 degrees 2θ.

Minor shifts in peak positioning may be present in the diffraction patterns of the Form I polymorph, the Form II polymorph, the Form III polymorph, the solvated crystalline forms, the hydrated crystalline forms, and the salt forms of Compound 1 as a result of imperfections in the spacing of the crystal diffraction planes associated with the route of manufacture. Further, the solvated crystalline forms and the hydrated crystalline forms are expected to show some shifting in the positioning of the diffraction peaks due to increased mobility of solvent molecules within solvent channels in the crystal lattice.

3. Differential Scanning Calorimetry (DSC

DSC data of the anhydrous forms, the hydrated forms, the solvated forms and the salts of Compound 1 were determined using a TA Instruments 2920 differential scanning calorimeter. Each sample (an amount of about 1 mg to about 2 mg) was placed in an unsealed aluminum pan and heated at 10° C./minute. Transition temperature ranges were defined from the extrapolated onset to the maximum of the peak.

One or more endothermal events at lower temperatures in the DSC thermograms were associated with enthalpy changes that occurred as either water or solvent was lost from the solvate crystal lattice. The highest temperature endotherm or endotherms were associated with the melting of the Form I polymorph.

Table 12 below summarizes typical DSC measurements obtained for the various crystalline forms of Compound 1.

TABLE 12

DSC Analysis

| Crystalline Form | Thermal event | Temperature ° C. |
|---|---|---|
| Form I Polymorph | Endotherm (Form I polymorph melt) | 239–241 |
| Form II Polymorph | (a) Endotherm (Form II polymorph melt) | 210–212 |
|  | (b) Exotherm (recrystallization) | 213–214 |
|  | (c) Endotherm (Form I polymorph melt) | 240–242 |
| Form III Polymorph | Exotherm | 158–163 |
|  | Endotherm | 235–237 |
| Acetic Acid Solvate* | (a) Endotherm (desolvation) | 113–121 |
|  | (b) Endotherm | 211–213 |
|  | (c) Exotherm | 216–219 |
|  | (d) Endotherm | 238–241 |
| NMP Solvate* | (a) Endotherm (desolvation) | 128–145 |
|  | (b) Endotherm | 236–237 |
| Monohydrate Crystalline Form* | (a) Endotherm (dehydration) | 65–96 |
|  | (b) Endotherm | 140–149 |
|  | (c) Exotherm | 152–157 |
|  | (d) Endotherm | 240–241 |
| Dihydrate Crystalline Form* | (a) Endotherm (dehydration) | 55–82 |
|  | (b) Exotherm | 155–165 |
|  | (c) Endotherm | 238–240 |
| Sodium Salt | Endotherm (melting point) | 229–233 |
| Hydrochloric acid Salt | Endotherms (corresponding to weight loss) | 179–199/225 |
| Mesylate Salt | Endotherm (melting point) | 209–212 |
| Tosylate Salt | Endotherm (melting point) | 173–177 |

*Solvent and water loss were confirmed by TG-IR

Figure 12:
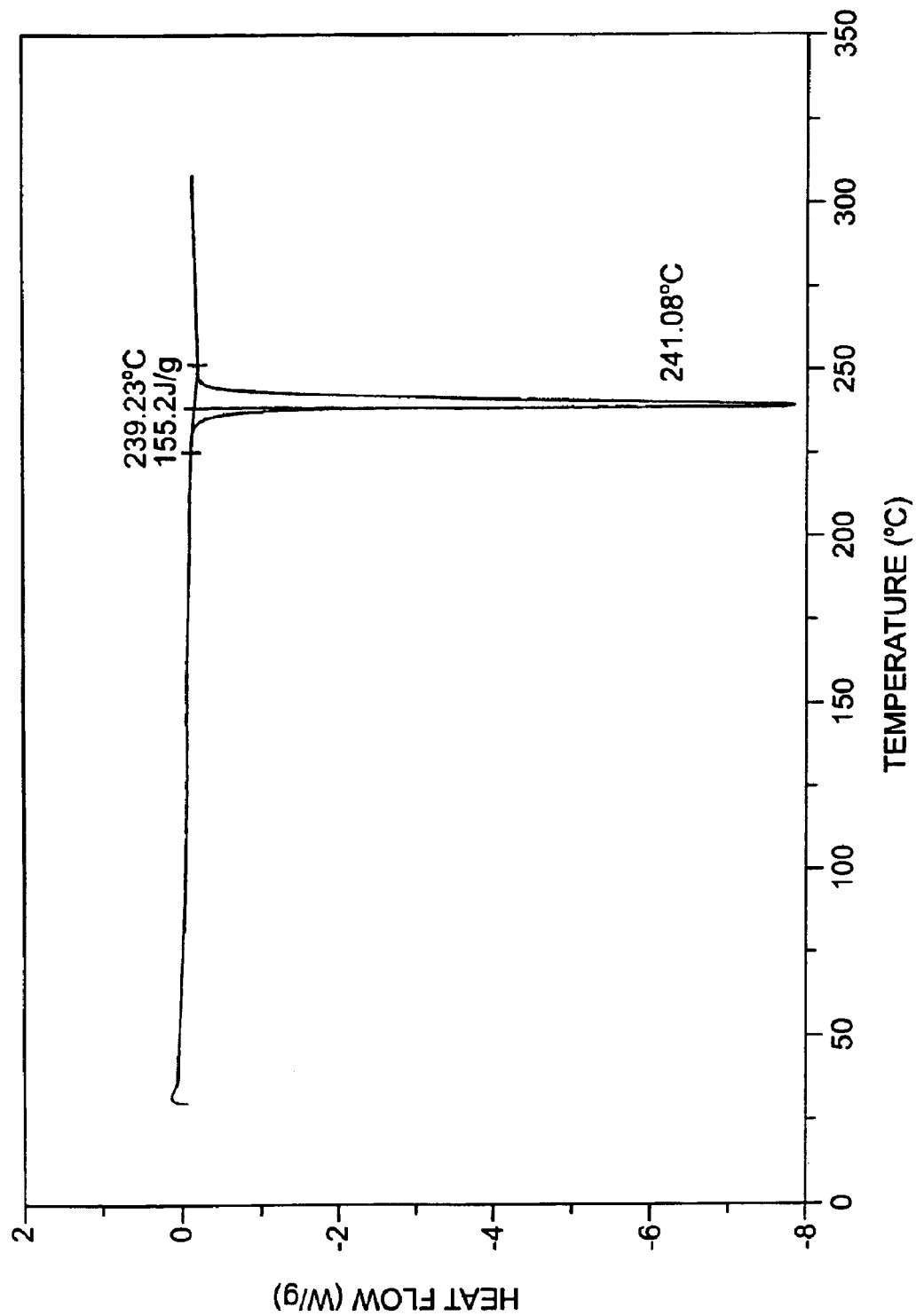
FIG. 12 shows an illustrative differential scanning calorimetry thermogram of Form I polymorph of Compound 1.
Figure 13:
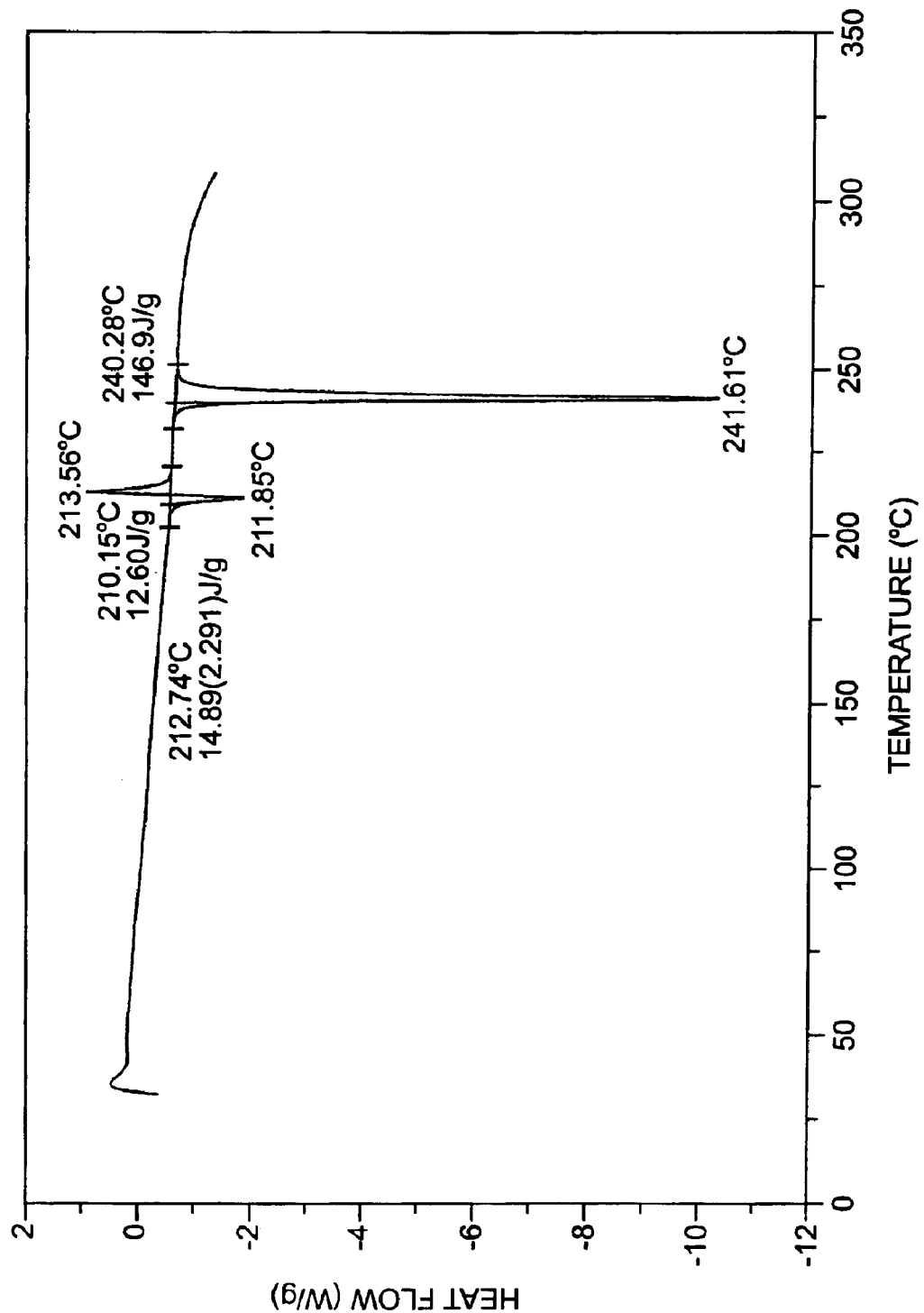
FIG. 13 shows an illustrative differential scanning calorimetry thermogram of Form II polymorph of Compound 1.
Figure 14:
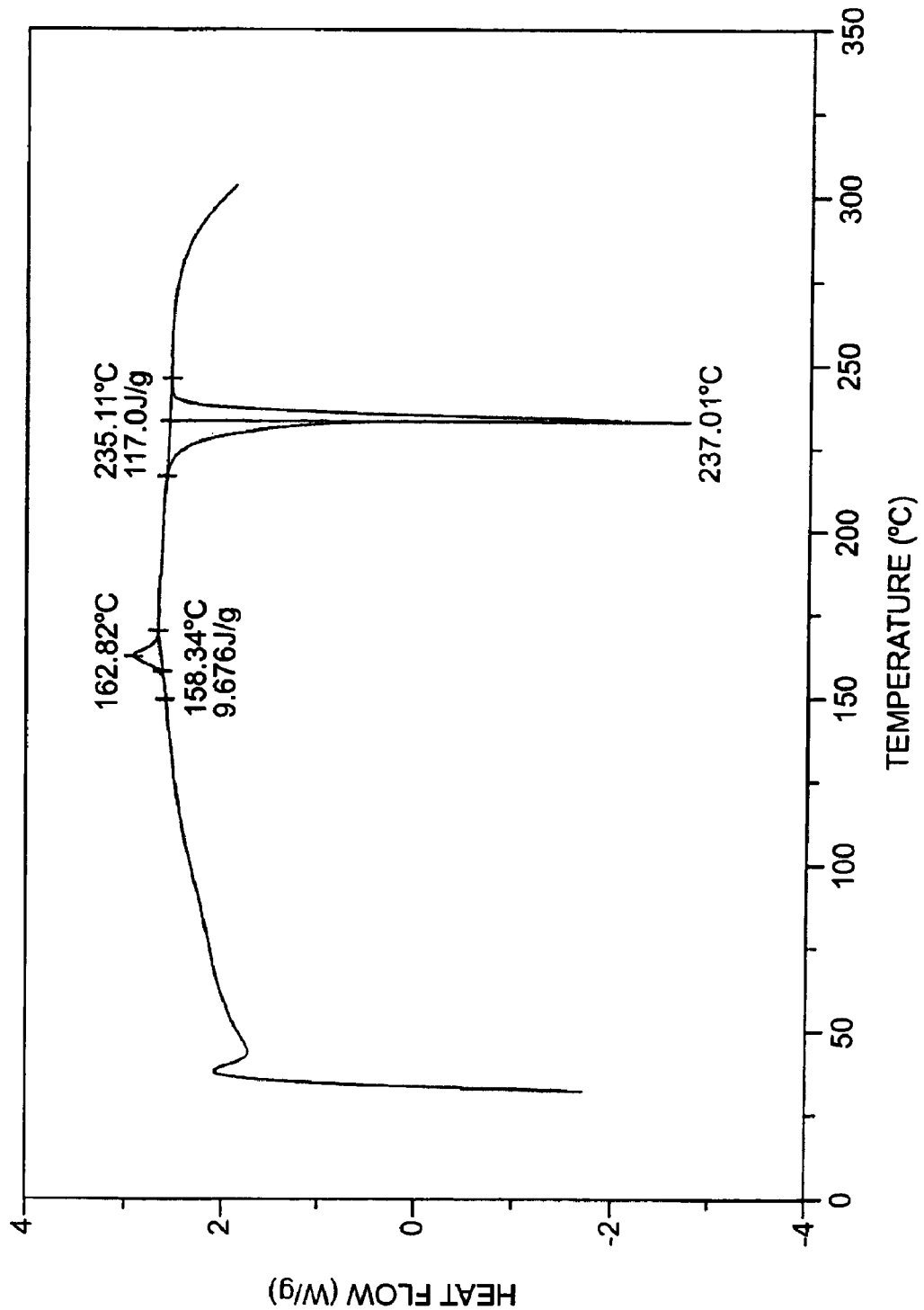
FIG. 14 shows an illustrative differential scanning calorimetry thermogram of Form III polymorph of Compound 1.
Figure 15:
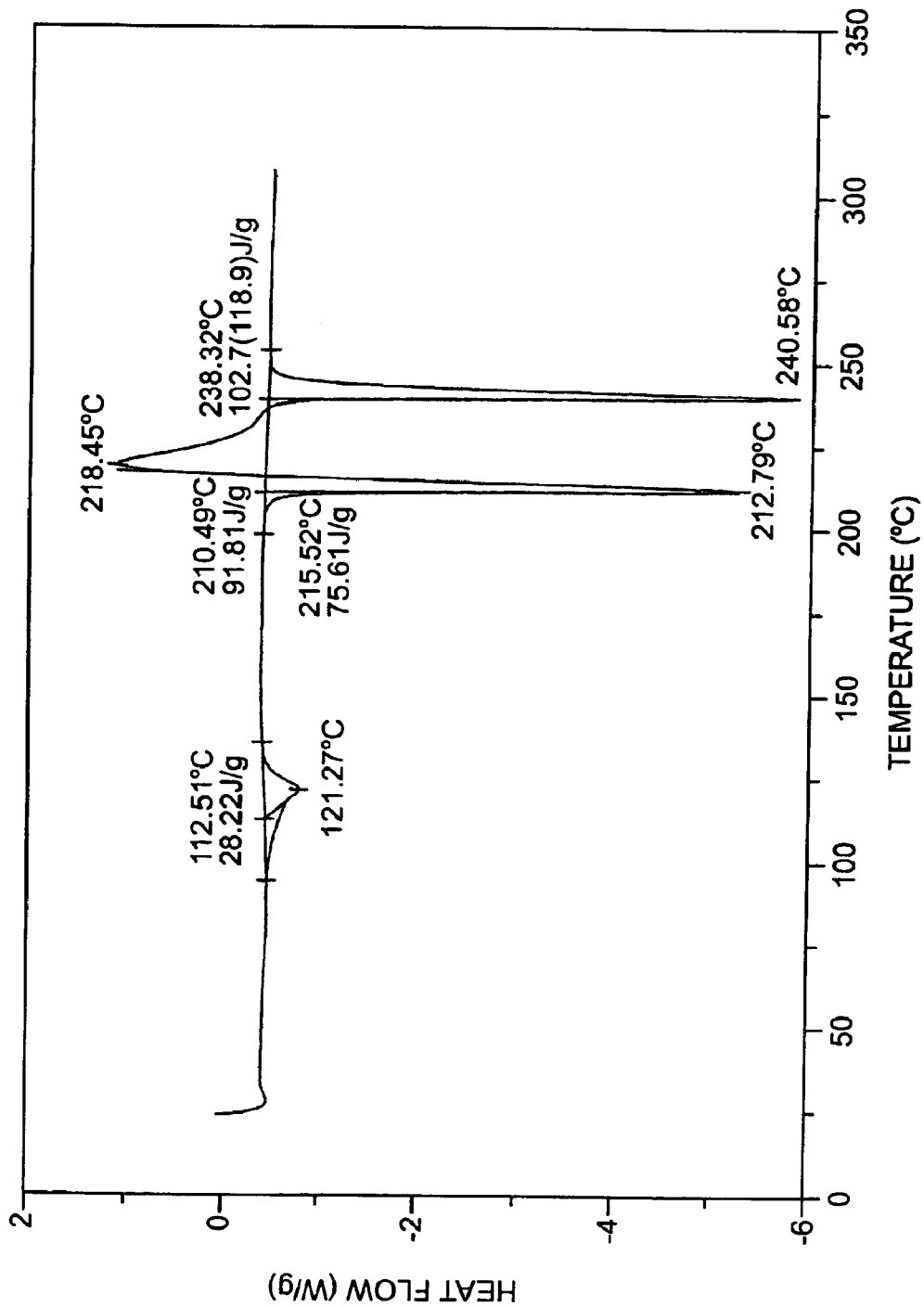
FIG. 15 shows an illustrative differential scanning calorimetry thermogram of the acetic acid solvated crystalline form of Compound 1.
Figure 16:
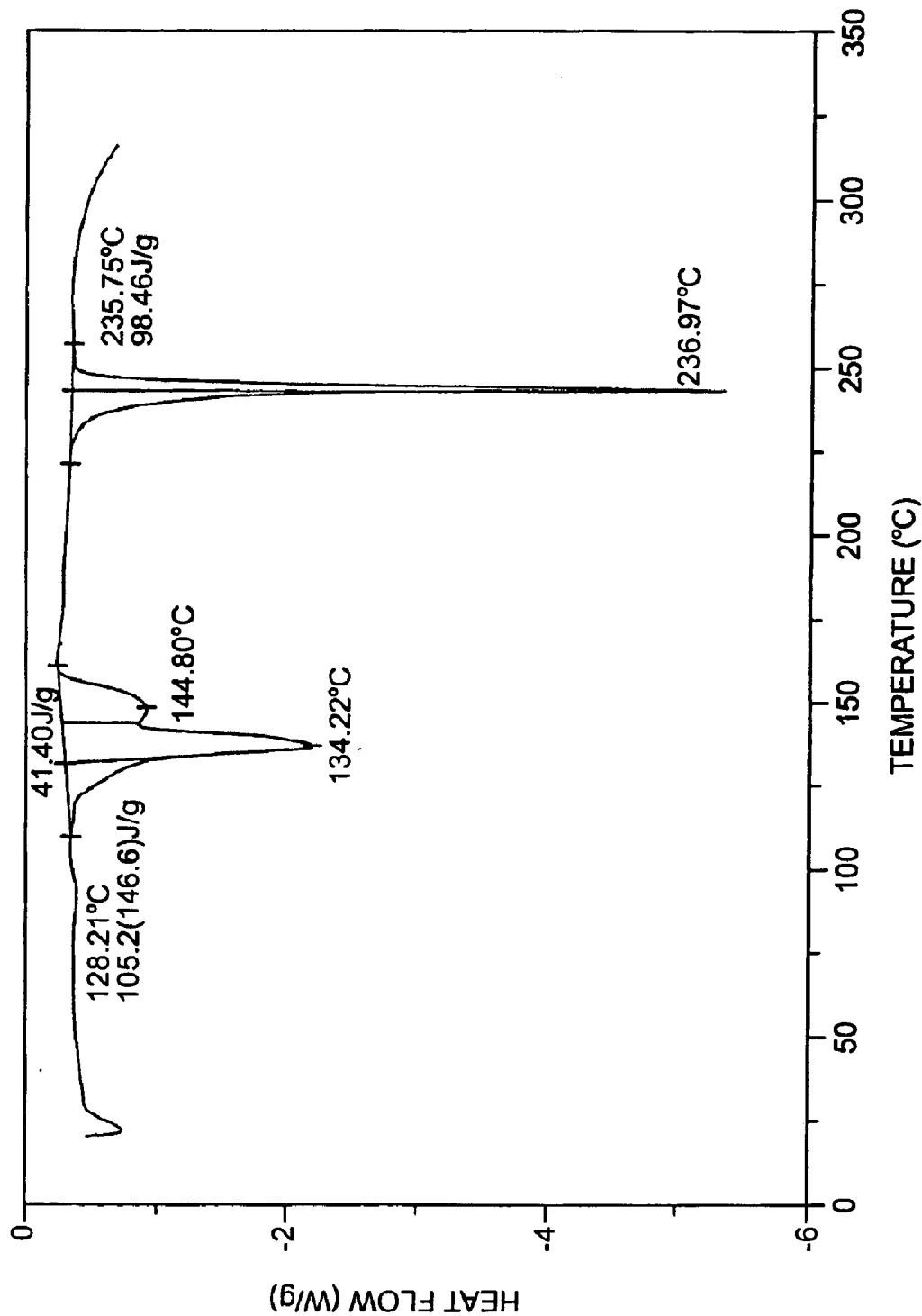
FIG. 16 shows an illustrative differential scanning calorimetry thermogram of the NMP solvated crystalline form of Compound 1.
Figure 17:
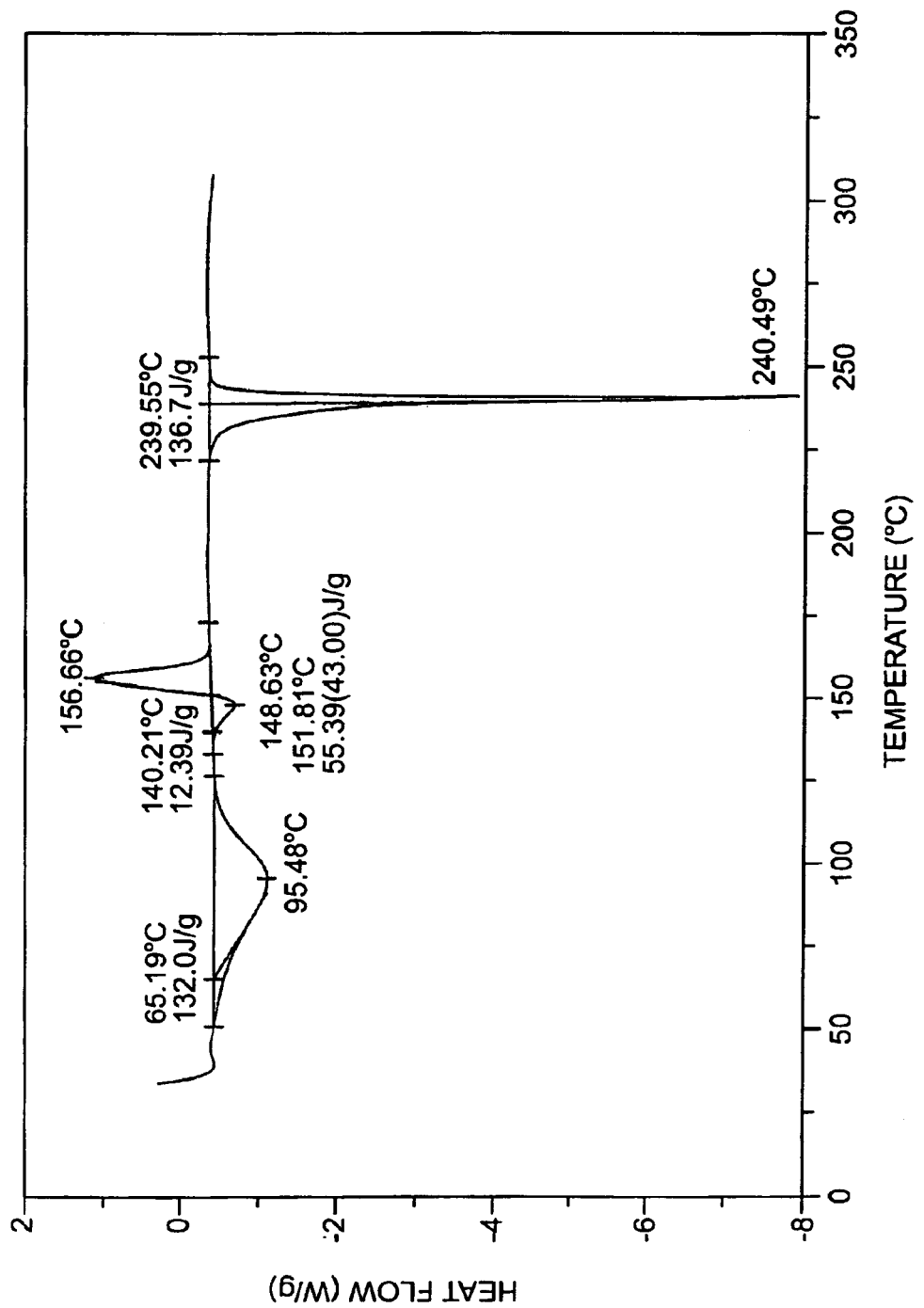
FIG. 17 shows an illustrative differential scanning calorimetry thermogram of the monohydrate crystalline form of Compound 1.
Figure 18:
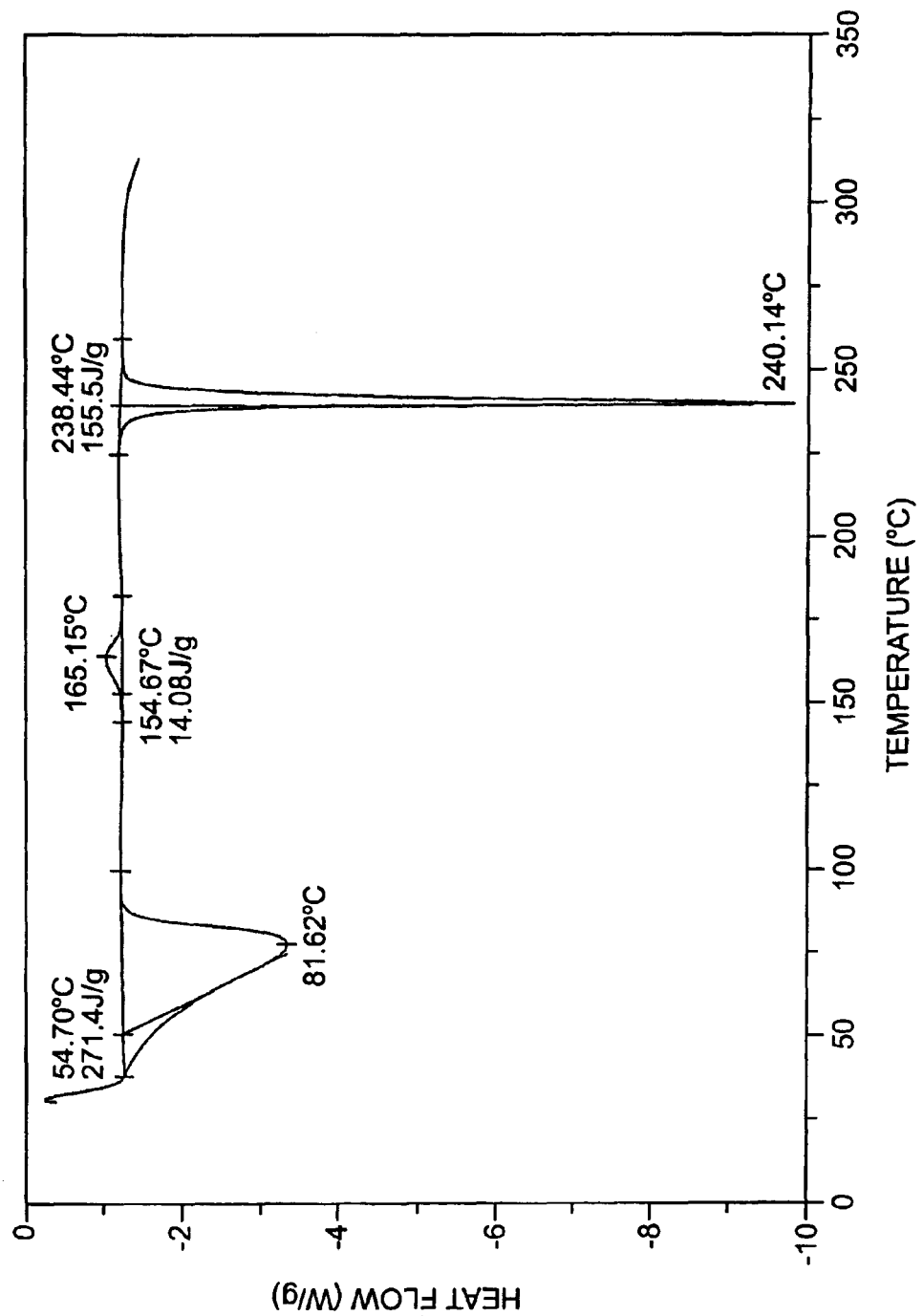
FIG. 18 shows an illustrative differential scanning calorimetry thermogram of the dihydrate crystalline form of Compound 1.
Figure 19:
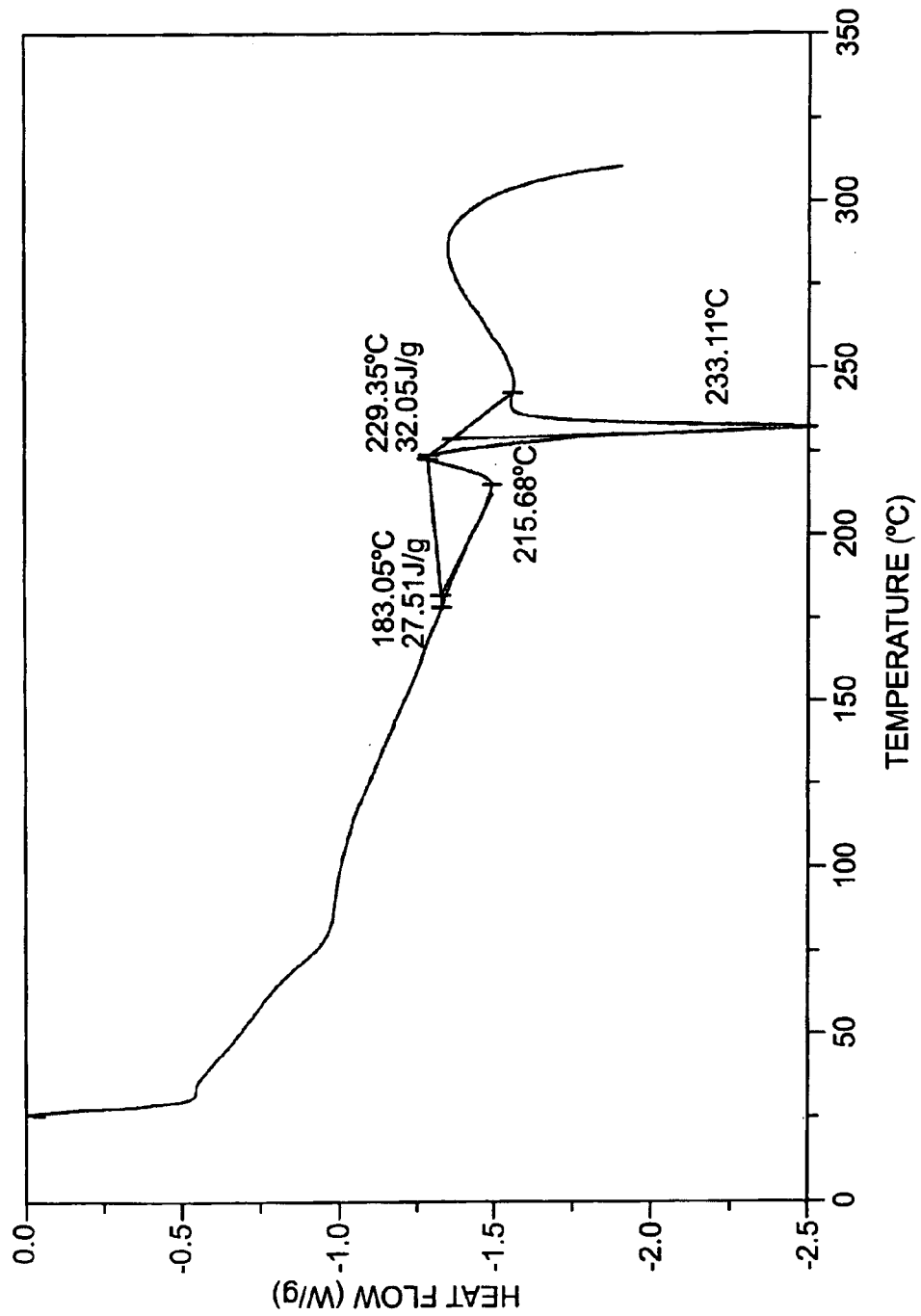
FIG. 19 shows an illustrative differential scanning calorimetry thermogram of the crystalline sodium salt of Compound 1.
Figure 20:
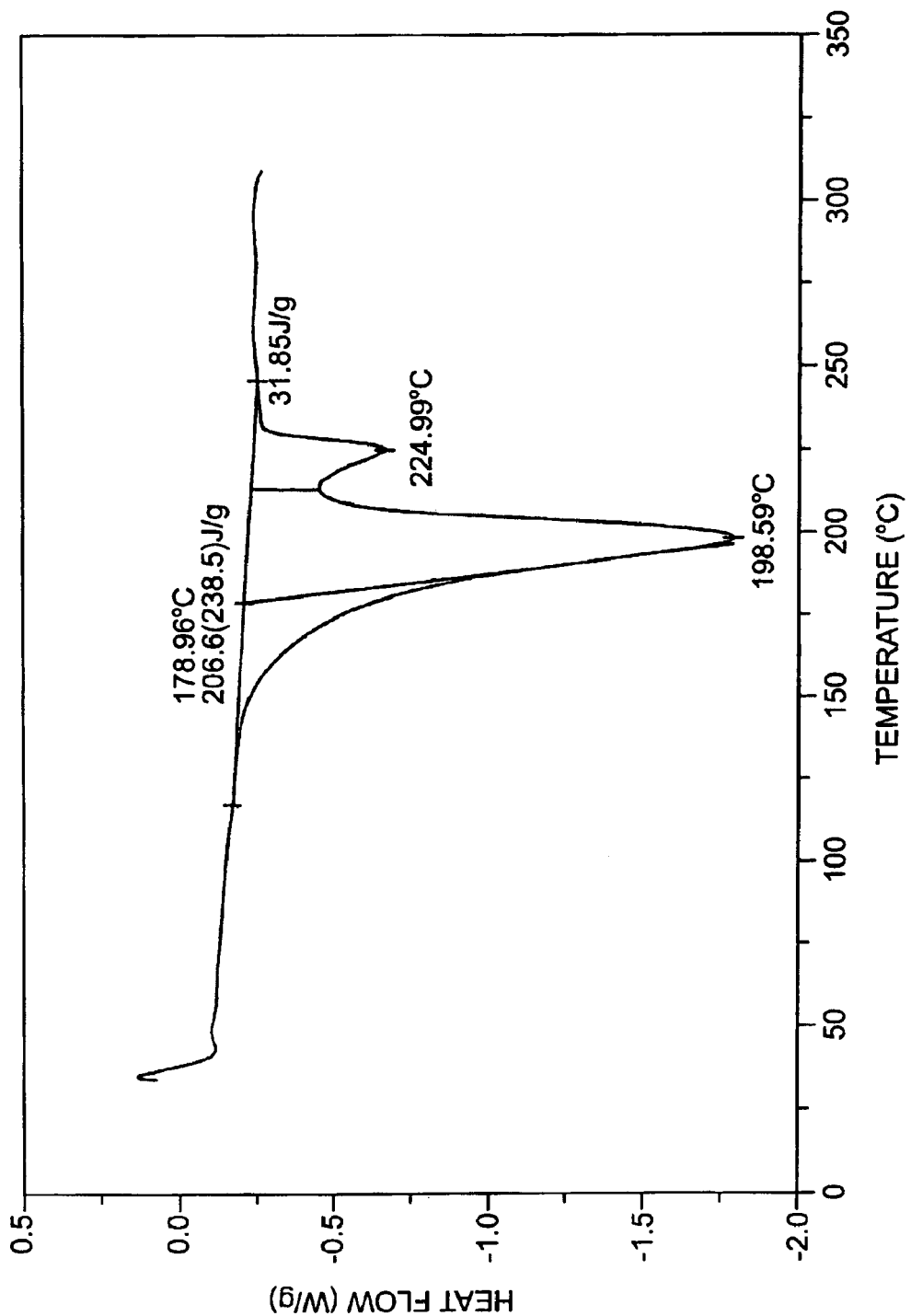
FIG. 20 shows an illustrative differential scanning calorimetry thermogram of the crystalline hydrochloride salt of Compound 1.
Figure 21:
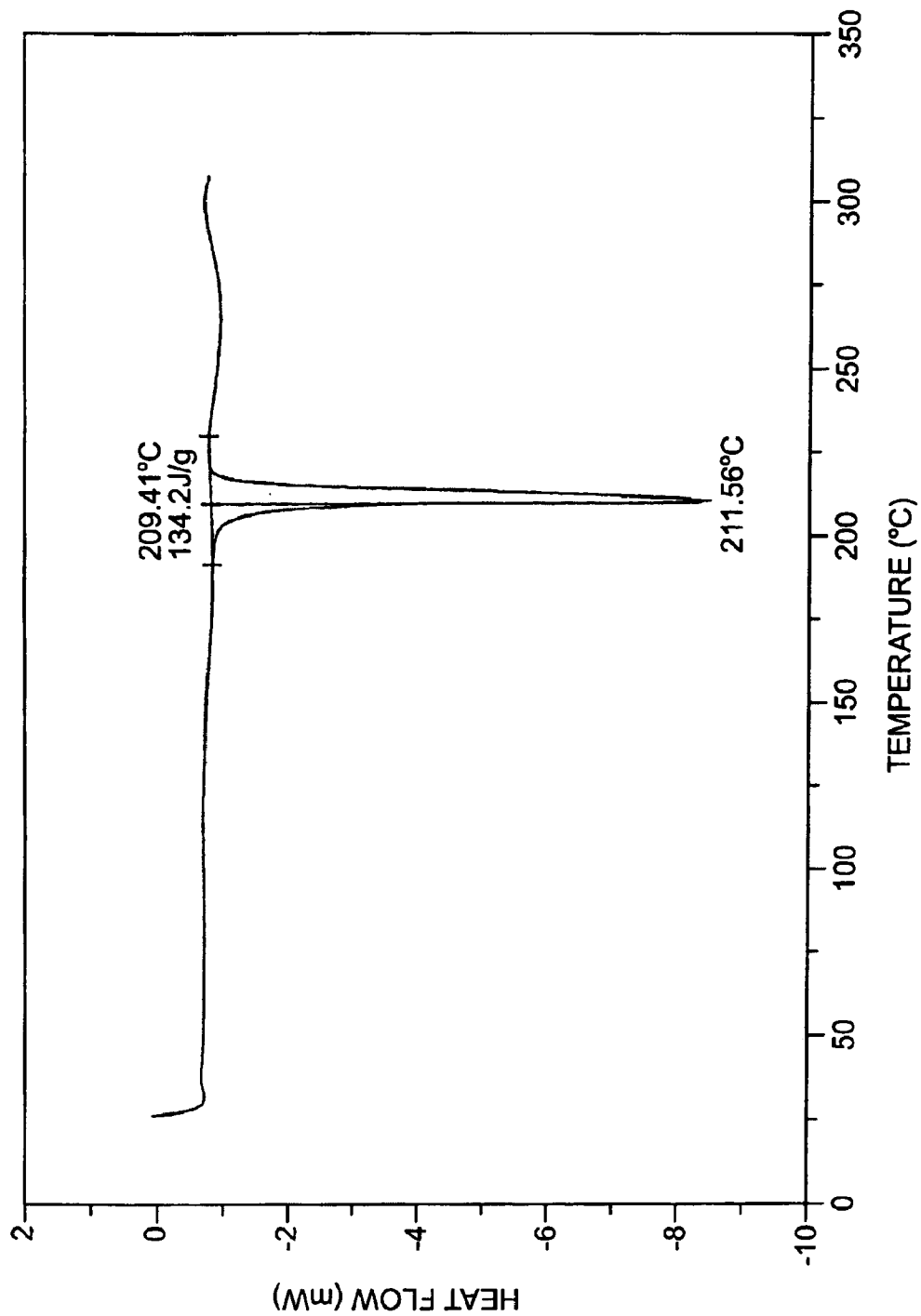
FIG. 21 shows an illustrative differential scanning calorimetry thermogram of the crystalline methanesulfonic acid (mesylate) salt of Compound 1.
Figure 22:
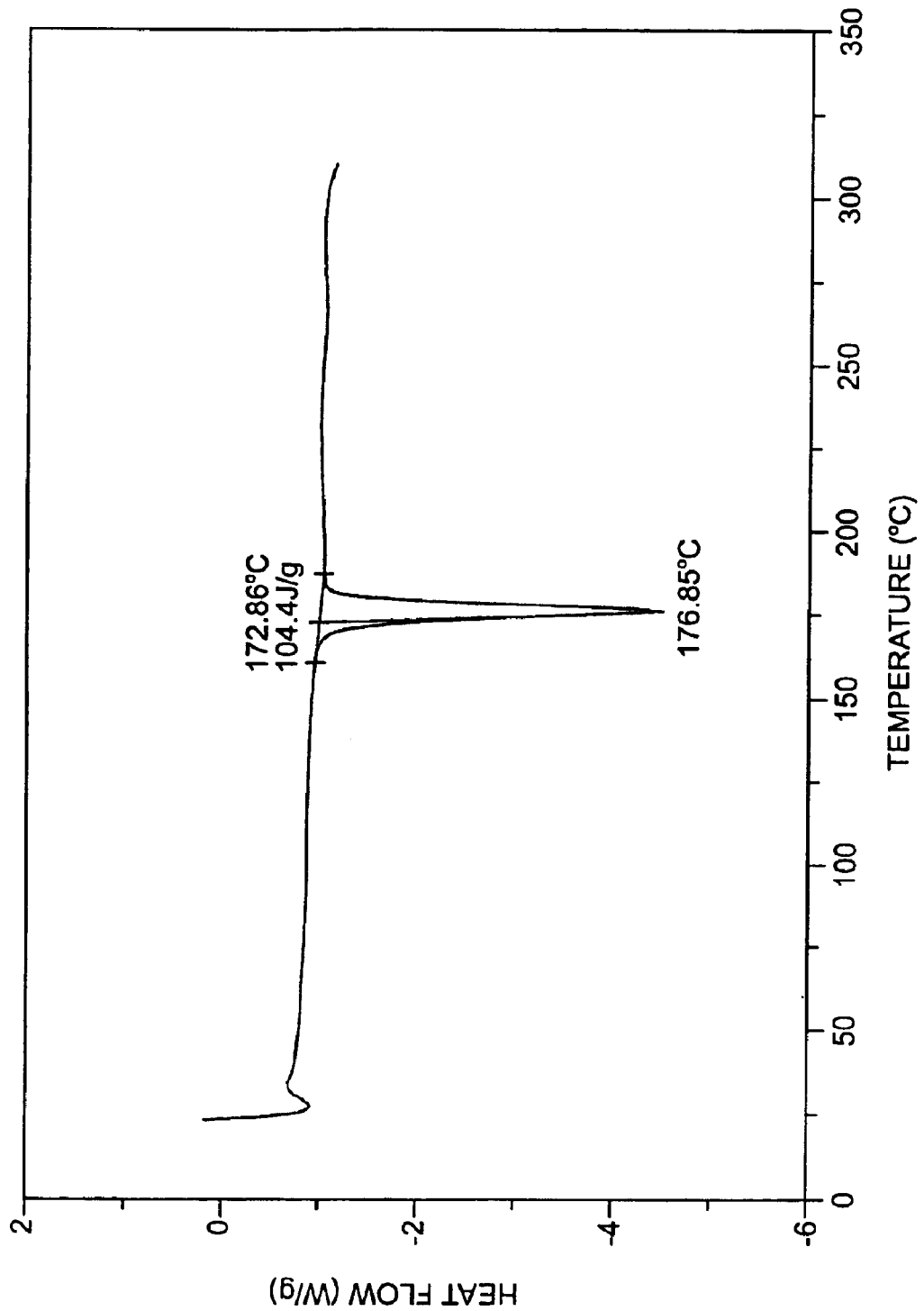
FIG. 22 shows an illustrative differential scanning calorimetry thermogram of the crystalline p-toluenesulfonic acid (tosylate) salt of Compound 1.

FIGS. 12–22 set forth typical DSC thermograms for the following crystalline forms of Compound 1:

(1) the Form I polymorph (FIG. 12);

(2) the Form II polymorph (FIG. 13);

(3) the Form III polymorph (FIG. 14);

(4) the acetic acid solvate (FIG. 15);

(5) the NMP solvate (FIG. 16);

(6) the monohydrate crystalline form (FIG. 17);

(7) the dihydrate crystalline form (FIG. 18);

(8) the crystalline sodium salt of Compound 1 (FIG. 19);

(9) the crystalline hydrochloride salt of Compound 1 (FIG. 20);

(10) the crystalline mesylate salt of Compound 1 (FIG. 21);

(11) the crystalline tosylate salt of Compound 1 (FIG. 22);

The Form I polymorph exhibits a melting point in a range from about 239° C. to about 241° C. The Form II polymorph shows an endothermic transition in a range of about 210° C. to about 212° C. followed by an exothermic transition in a range of about 213° C. to about 214° C. The endothermic transition corresponds to the melting of the Form II polymorph and the exothermic transition corresponds to the recrystallization of Compound 1 to the Form I polymorph. The DSC subsequently shows a melting/decomposition endotherm characteristic of the Form I polymorph at about 240–242° C. The Form III polymorph shows an endothermic transition in a range of about 235° C. to about 237° C. and an exothermic transition in a range of about 158° C. to about 163° C.

4. Thermogravimetric Analysis

Thermogravimetric analysis of Form I, Form II, Form III, sodium salt, hydrochloride salt, mesylate salt and tosylate salt of Compound 1 was performed using a TA Instruments TGA 2950 thermogravimetric analyzer. Samples were placed in an unsealed aluminum pan under nitrogen purge. Data for Form I, Form II, the dihydrate, the sodium salt, the hydrochloride salt, the mesylate salt and the tosylate salt of Compound 1 were collected from room temperature to 300° C. at 10° C./minute.

Thermogravimetric analysis of Form III, the monohydrate, the acetic acid solvate and the NMP solvate of Compound 1 was performed using a TA Instruments TG Analyzer 2050. Samples were placed in an unsealed ceramic pan under nitrogen purge. The monohydrate, the acetic acid solvate and the NMP solvate of Compound 1 data were collected from room temperature to 250° C. at 10° C./minute. Data for Form III were collected from room temperature to 225° C. at 10° C./minute.

Table 13 below summarizes typical thermogravimetry measurements obtained for the various crystalline forms of Compound 1. Weight loss of about 1% or less generally corresponds to loss of surface solvent.

TABLE 13

Thermogravimetric Analysis

| Crystalline Form | Thermal Event | Temperature (° C.) | Weight Loss (%) |
|---|---|---|---|
| Form I Polymorph | — | — | — |
| Form II Polymorph | — | — | — |
| Form III Polymorph | — | — | — |
| Acetic Acid Solvate* | Loss of acetic acid | 115 | 4.7 |
| NMP Solvate* | Loss of NMP | 148 | 22.0 |
| Monohydrate Crystalline Form* | Loss of one mole of water | 87 | 4.0 |
| Dihydrate Crystalline Form* | Loss of two moles of water | 63 | 8.1 |
| Sodium Salt | — | — | — |
| Monohydrochloride Salt | Weight loss | 169 | 4.2 |
|  |  | 208 | 5.7 |
| Mesylate Salt | — | — | — |
| Tosylate Salt | — | — | — |

*Solvent and water loss were confirmed by TG-IR.

Figure 23:
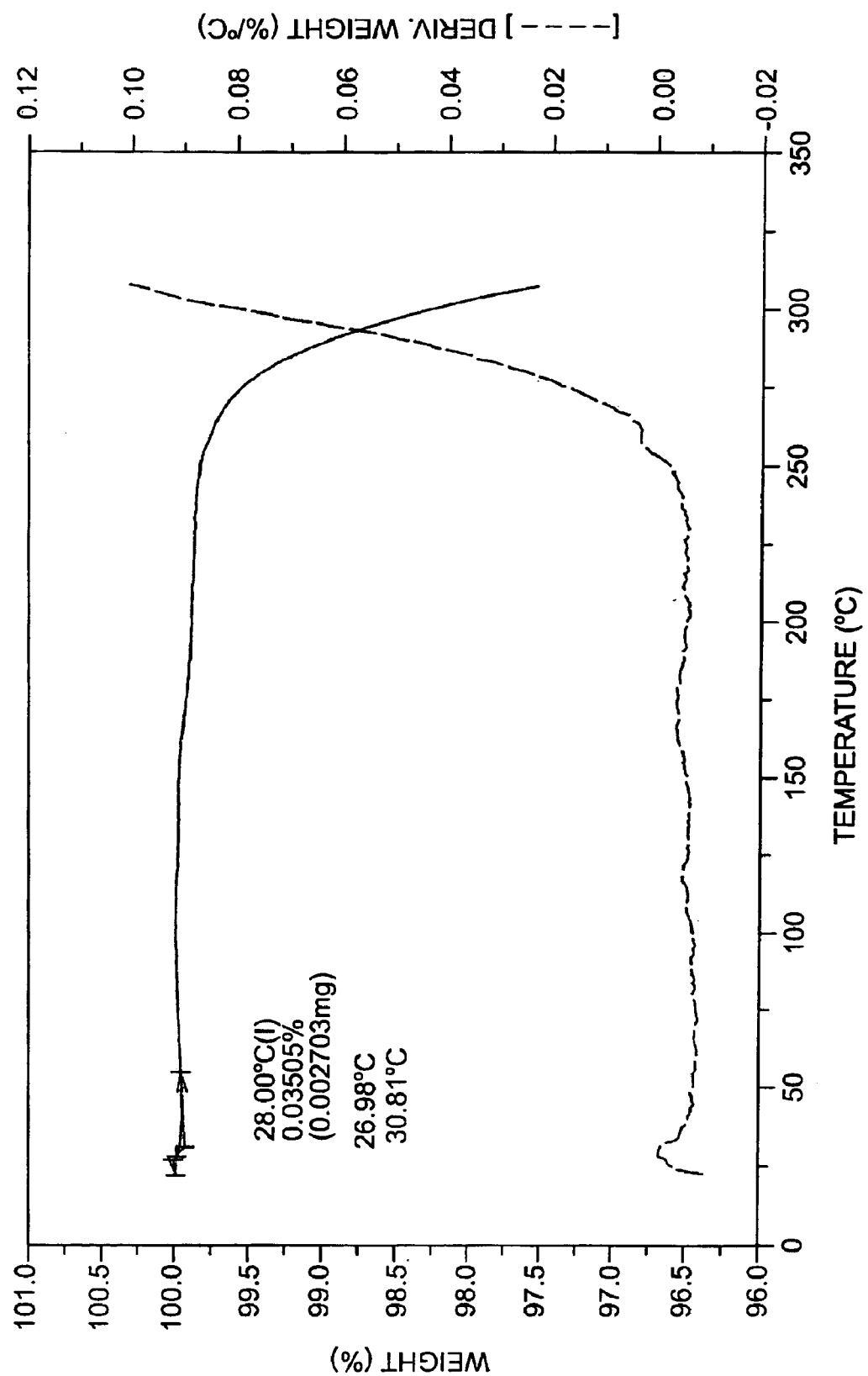
FIG. 23 shows an illustrative thermogravimetric analysis profile of the Form I polymorph of Compound 1.
Figure 24:
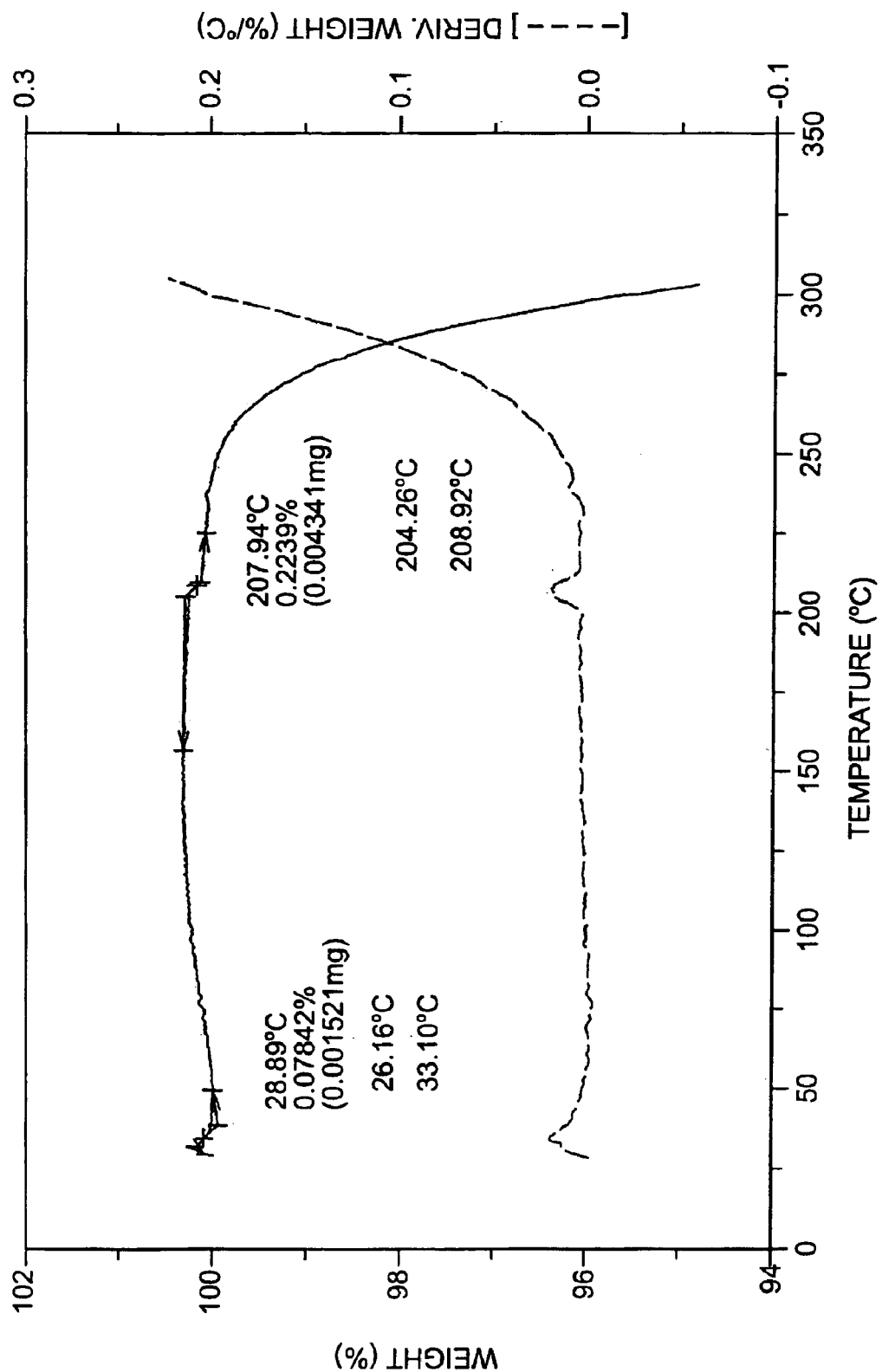
FIG. 24 shows an illustrative thermogravimetric analysis profile of the Form II polymorph of Compound 1.
Figure 25:
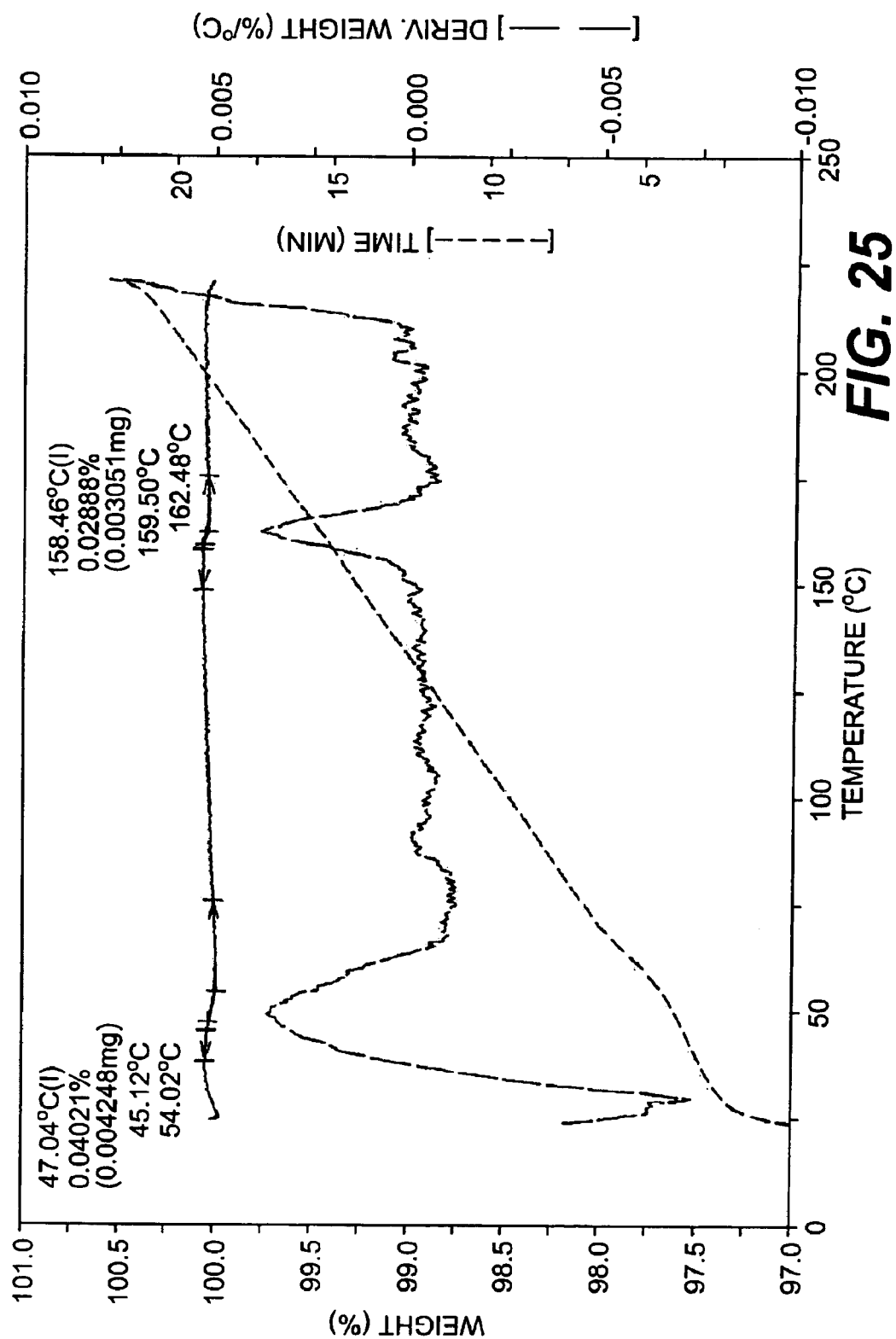
FIG. 25 shows an illustrative thermogravimetric analysis profile of the Form III polymorph of Compound 1.
Figure 26:
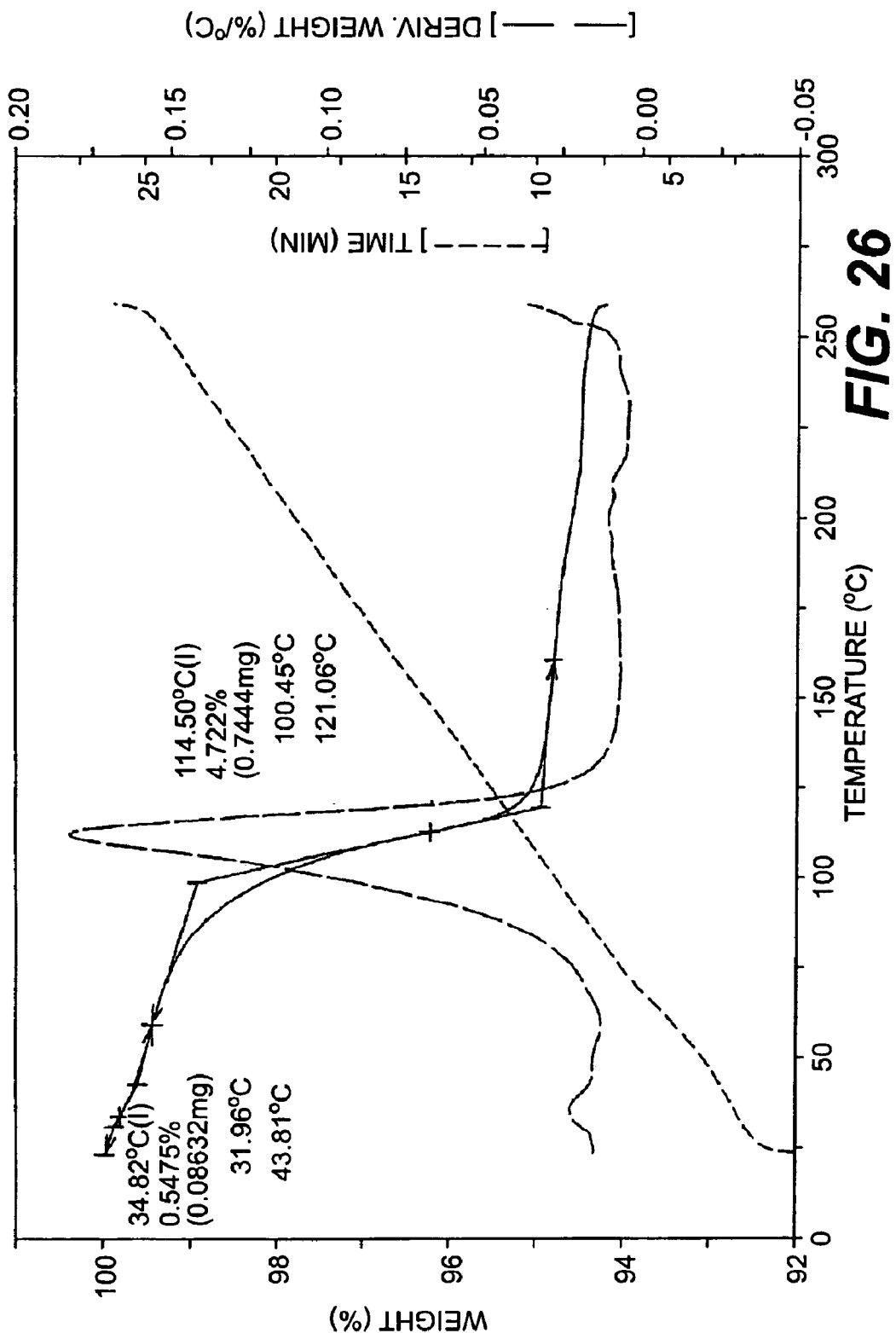
FIG. 26 shows an illustrative thermogravimetric analysis profile of the acetic acid solvate of Compound 1.
Figure 27:
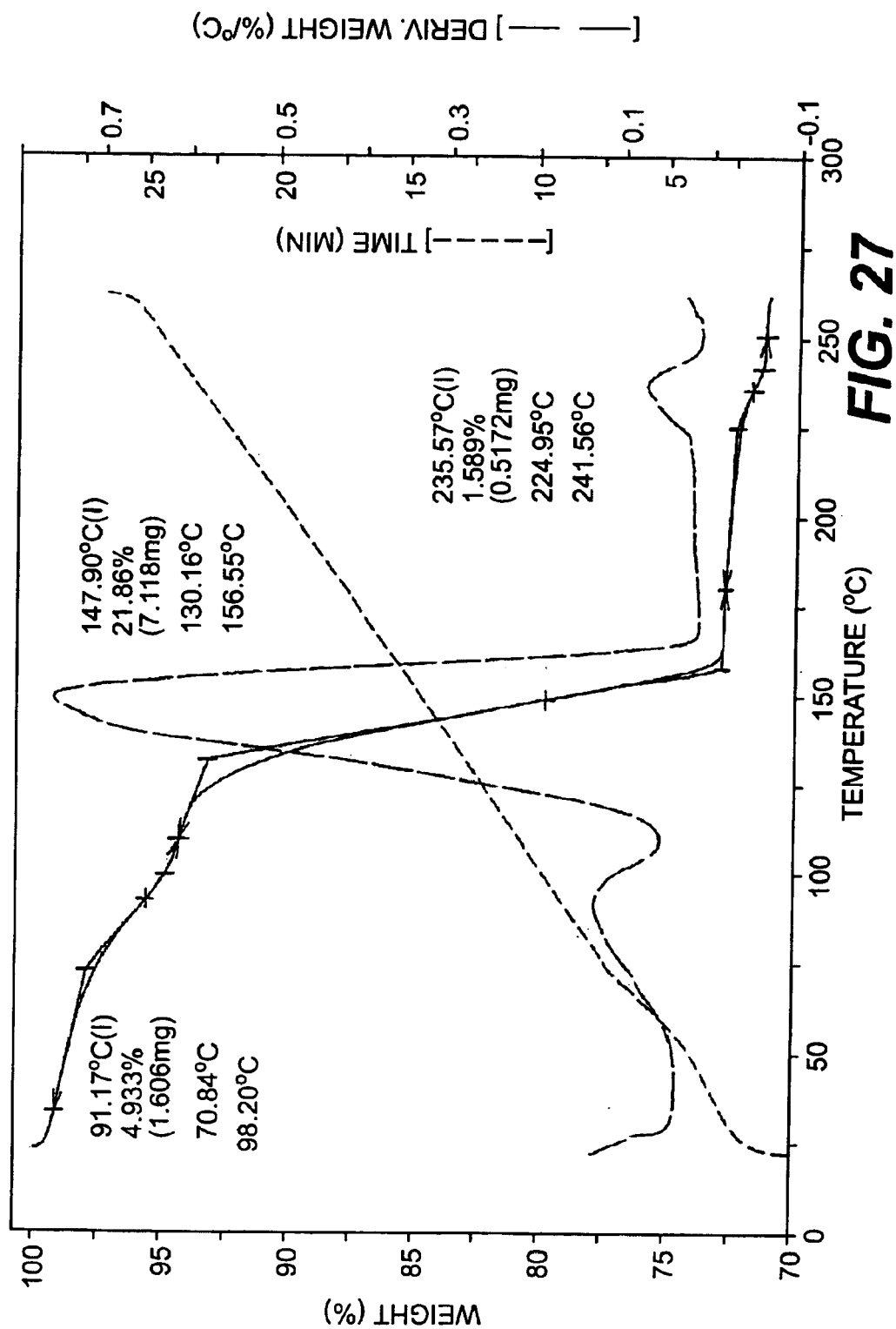
FIG. 27 shows an illustrative thermogravimetric analysis profile of the NMP solvate of Compound 1.
Figure 28:
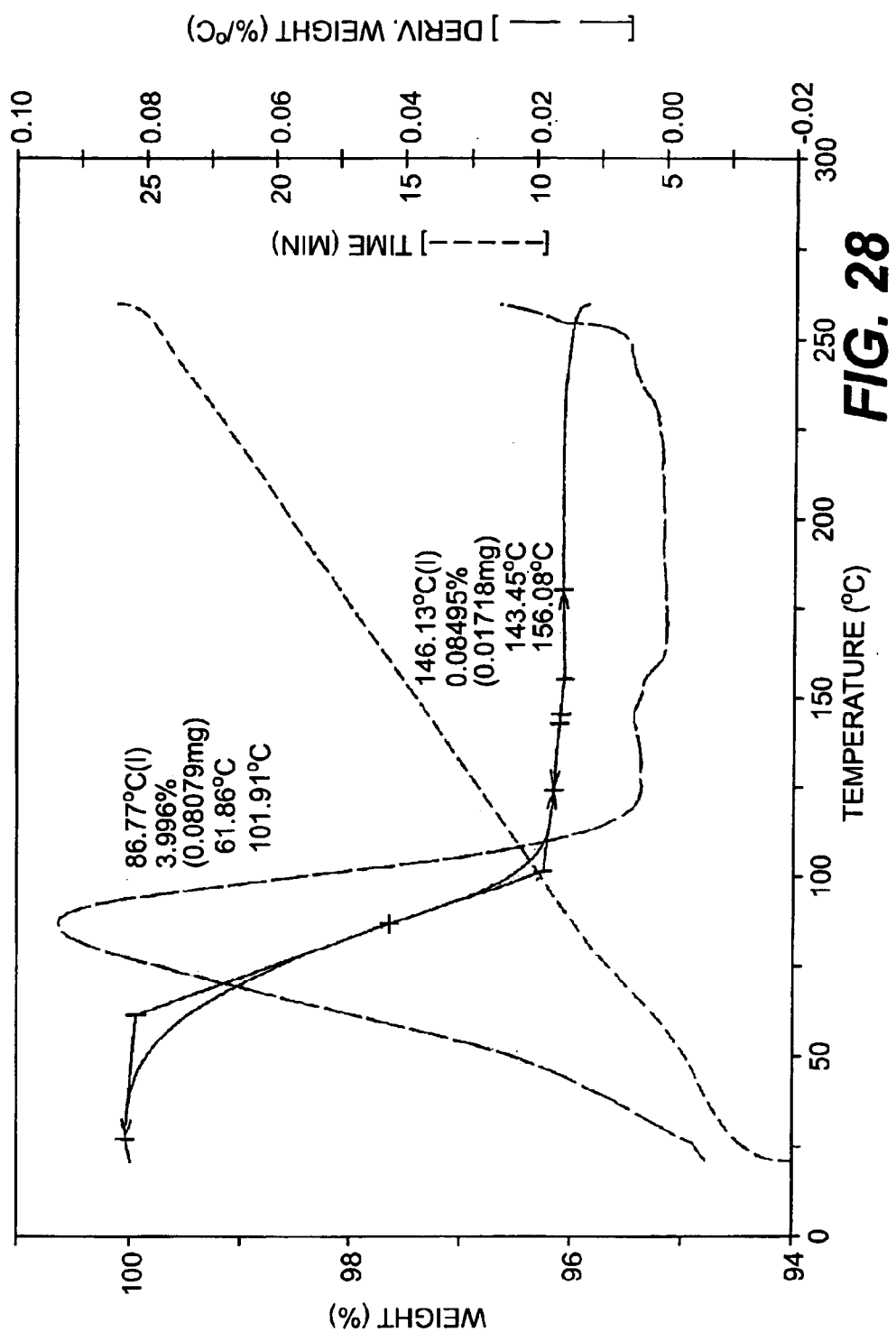
FIG. 28 shows an illustrative thermogravimetric analysis profile of the monohydrate crystalline form of Compound 1.
Figure 29:
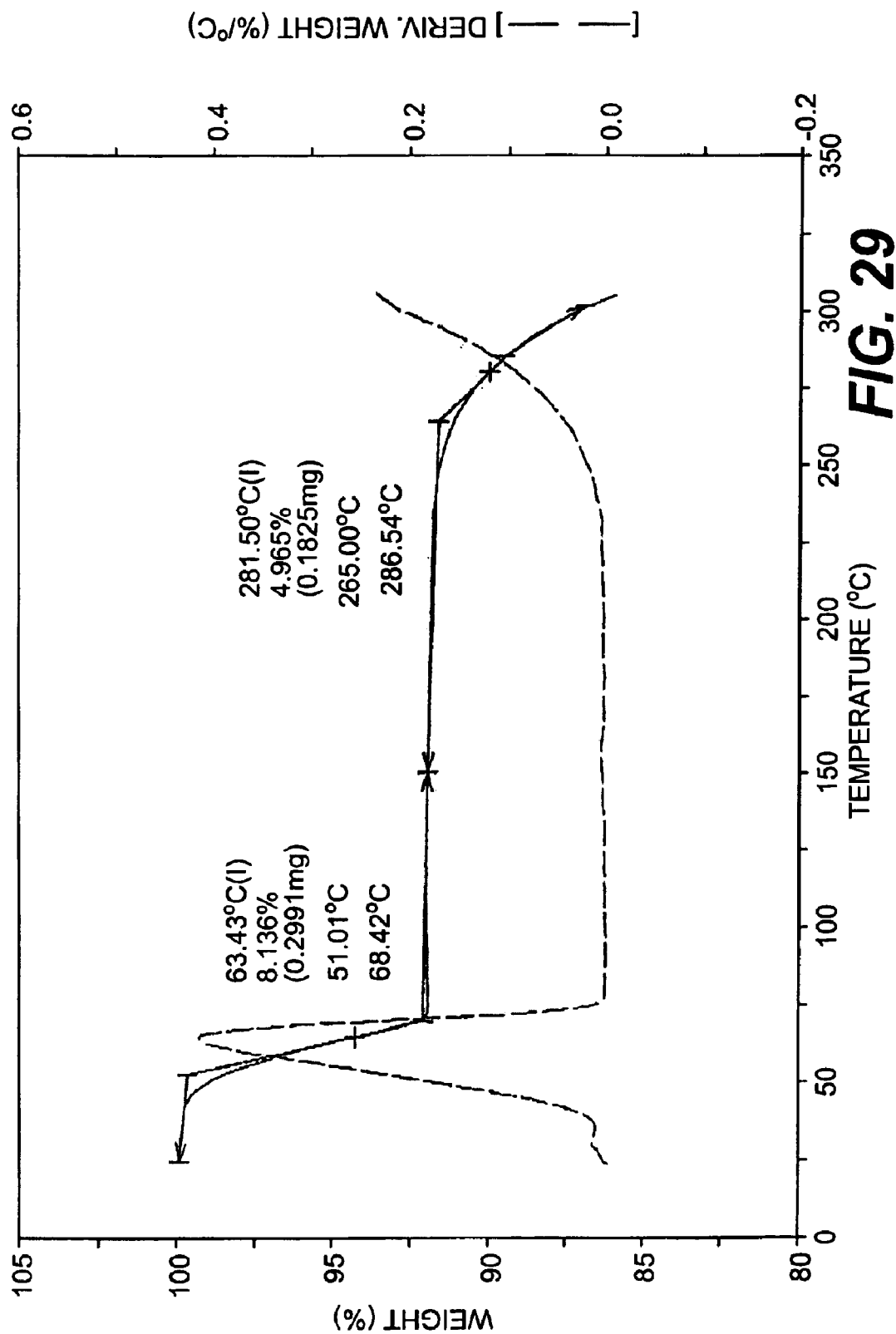
FIG. 29 shows an illustrative thermogravimetric analysis profile of the dihydrate crystalline form of Compound 1.
Figure 30:
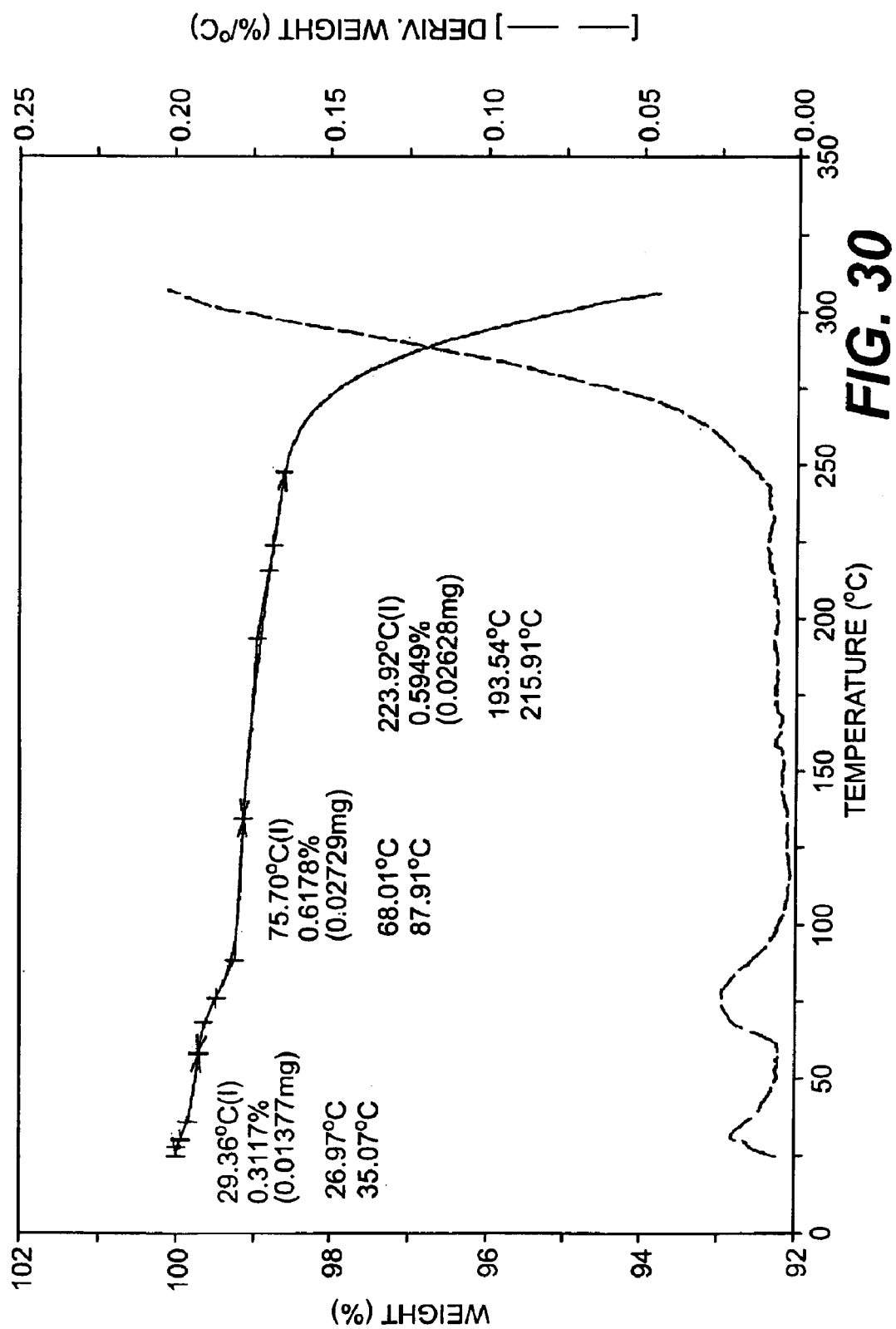
FIG. 30 shows an illustrative thermogravimetric analysis profile of the crystalline sodium salt of Compound 1.

FIGS. 23–33 set forth typical thermogravimetric analysis profiles for the following crystalline forms of Compound 1:

(1) FIG. 23 presents a thermogravimetric analysis profile obtained for a sample of the Form I polymorph;

(2) FIG. 24 presents a thermogravimetric analysis profile obtained for a sample of the Form II polymorph;

(3) FIG. 25 presents a thermogravimetric analysis profile obtained for a sample of the Form III polymorph;

(4) FIG. 26 presents a thermogravimetric analysis profile obtained for a sample of the acetic acid solvate;

(5) FIG. 27 presents a thermogravimetric analysis profile obtained for a sample of the NMP solvate;

(6) FIG. 28 presents a thermogravimetric analysis profile obtained for a sample of the monohydrate crystalline form;

(7) FIG. 29 presents a thermogravimetric analysis profile obtained for a sample of the dihydrate crystalline form; and (8) FIG. 30 presents a thermogrovimetric analysis profile obtained for a sample of the crystalline sodium salt of Compound 1.

Figure 31:
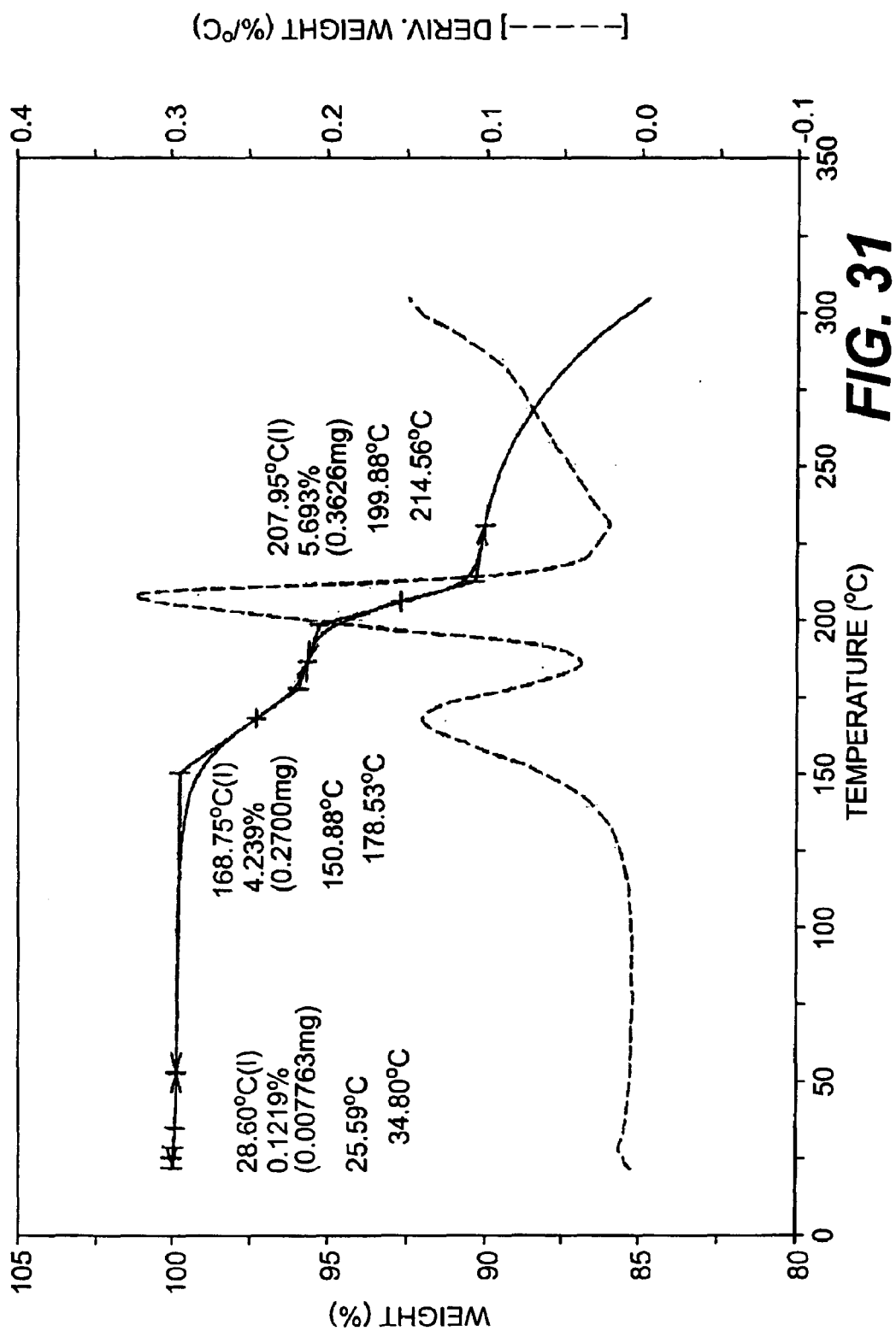
FIG. 31 shows an illustrative thermogravimetric analysis profile of the crystalline hydrochloride salt of Compound 1.

(9) FIG. 31 presents a thermogravimetric analysis profile obtained for a sample of the crystalline hydrochloride salt of Compound 1.

Figure 32:
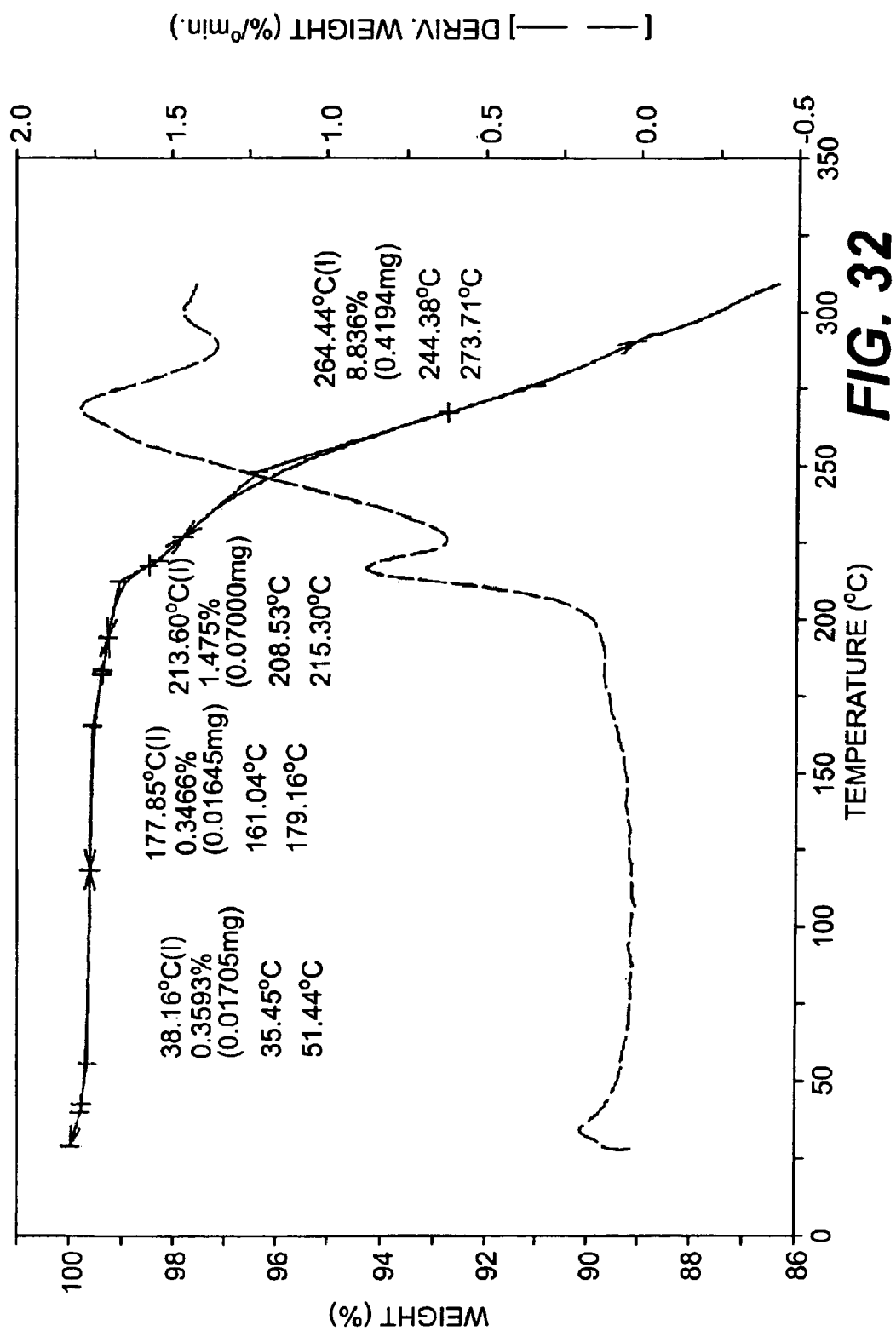
FIG. 32 shows an illustrative thermogravimetric analysis profile of the crystalline methanesulfonic acid (mesylate) salt of Compound 1.

(10) FIG. 32 presents a thermogravimetric analysis profile obtained for a sample of the crystalline mesylate salt of Compound 1.

Figure 33:
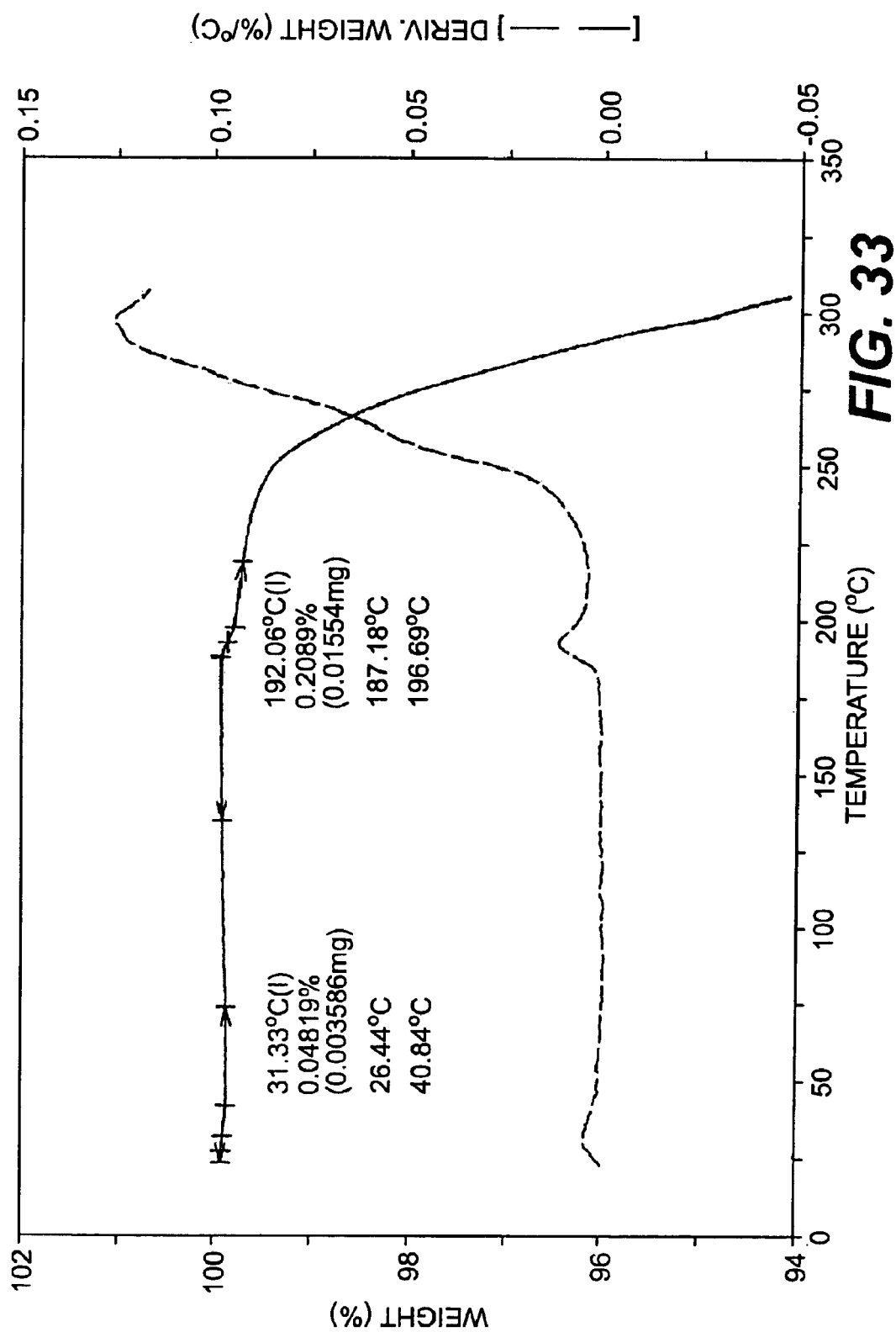
FIG. 33 shows an illustrative thermogravimetric analysis profile of the crystalline p-toluenesulfonic acid (tosylate) salt of Compound 1.

(11) FIG. 33 presents a thermogravimetric analysis profile obtained for a sample of the crystalline tosylate salt of Compound 1.

5. Infrared Spectroscopy

All samples were scanned in the range range 600 to 4000 cm$^{-1}$ using a Bio-RAD FTS-45 spectrophotometer. Spectra of Form I, Form II, acetic acid solvate, sodium salt, monohydrochloride salt, and tosylate salt of Compound 1 were collected using an IBM micro-MIR (multiple internal reflectance) accessory. Spectra of Form III, monohydrate, NMP solvate and mesylate salt of Compound 1 were collected using a Sensir microdiamond ATR (attenuated total reflectance) accessory. A warm saturated solution of Compound 1 in chloroform was analyzed using a solution cell of 0.2 mm path length with sodium chloride salt plates.

Tables 14A, 14B and 14C below summarize typical infrared absorption bands obtained for the various crystalline forms and salts of Compound 1. Typical infrared bands for Compound 1 in chloroform are also disclosed in Table 14A for comparison.

TABLE 14A

IR Bands (cm$^{-1}$)

| Spectral region | Form I Polymorph | Form II Polymorph | Form III Polymorph | Compound 1 In Chloroform |
|---|---|---|---|---|
| ν OH (associated), ν NH | 3379 (broad), 3156 | 3298, 3164 | 3207 (broad) | 3442, 3393(broad), 3163 |
| ν =CH (aromatic) | 3100–3000 | 3100–3000 | 3100–3000 | 3100–3000 (3100, 3075) |
| ν C=O | 1632 | 1635 | 1652 | 1640 |
| ν C=C (aromatic), pyrazole & pyrimidine ring stretching modes (ν C=C, C=N), *also δ CH$_2$, **also ν CNH (pyrazole) | 1579, 1502, 1485, 1464*, 1438* | 1578, 1496, 1465*, 1438* | 1582, 1500**, 1446*,1417 | 1584, 1541, 1498**, 1486, 1465*, 1439* |
| Pyrazole ring stretching mode | 1373 | 1388 | 1393 | 1389, 1373 |
| Pyrimidine ring stretching modes | 1274, 1224 | 1274, 1224 | 1272, 1220 | 1274, 1226 |
| ν =C—Cl | 1092 | 1091 | 1096 | 1093 |
| Pyrazole & Pyrimidine ring breathing modes, *also ν C-O (p-alcohol) | 1003*, 986, 973 | 1013*, 977 | 1015*, 980 | 1003*, 973 |
| δ =CH(para-substituted benzene, also 4(6)-substituted pyrimidine | 855, 840, 821 | 843, 823 | 846, 829 | 836 |

TABLE 14B

IR Bands (cm$^{-1}$)

| Spectral region | Monohydrate Crystalline Form | NMP Solvate | Acetic Acid Solvate |
|---|---|---|---|
| ν OH (associated), * also ν NH | p_OH & hydrate) 3500–3100 (broad) (3470*, 3292, 3170, 3153 | 3421*, 3213* (broad) | 3308* (broad) |

TABLE 14B-continued

IR Bands (cm$^{-1}$)

| Spectral region | Monohydrate Crystalline Form | NMP Solvate | Acetic Acid Solvate |
|---|---|---|---|
| ν =CH (aromatic) | 3100–3000 (3042) | 3100–3000 (3083, 3051, 3011) | 3100–3000 (3054, 3001) |
| Overtones/combination bands of acid dimer | | | 2800–2200 (2764, 2591) |
| ν C=O | 1626 | 1658, 1642 | (acid) 1719, (amide)1637 |
| ν C=C (aromatic) pyrazole & pyrimidine ring stretching modes (ν C=C, C=N), * also δ CH$_2$ | 1602, 1581, 1547, 1494, 1446*, 1437* | 1580, 1494 (broad) and 1446*, (broad) (and δ$_{as}$ CH$_3$) | 1581, 1517, 1498 (broad), 1467* (and δ$_{as}$ CH$_3$), 1438* (and δ$_{as}$ CH$_3$ ) |
| Pyrazole ring stretching mode | 1389 | 1380 | 1390 |
| ν C—O (acid dimmer | | | 1274 (broad) |
| Pyrimidine ring stretching modes | 1273, 1217 | 1273, 1221 | |
| ν =C—Cl | 1092 | 1080 | 1092 |
| Pyrazole & Pyrimidine ring breathing modes, *also ν C—O (p-alcohol) | 1016*, 989 | 1012*, 1008*, 987, 983 | 1015*, 977 |
| δ =CH (para-substituted benzene, also 4(6)-substituted pyrimidine | 845, 829 | 842 | 844, 832 |

TABLE 14C

IR Bands (cm$^{-1}$)

| Spectral region | Sodium Salt | Hydrochloride Salt | Mesylate Salt | Tosylate Salt |
|---|---|---|---|---|
| ν OH (associated) | 3412 (broad) | 3394 (broad) | 3391 (broad) | 3322 (broad) |
| ν NH$_2$$^+$, *ν NH | 3161* | 3200–2700 (3124), 2700–2300 (2713), 2107 | 3200–2800 (3159, 3121, 2850), | 3200–2800 (3193, 2849, 2808), 2800–2400 |
| ν =CH (aromatic) | 3100–3000 (3098, 3036) | 3100–3000 (3078, 3022) | 3100–3000 (3082, 3018) | 3100–3000 (3091, 3034) (3091, 3034) |
| ν C=O, *also δ NH$_2$$^+$ | 1631 | 1645, 1626* | 1645, 1630 | 1629 |
| ν C=C (aromatic) pyrazole & pyrimidine ring stretching modes (ν C=C, C=N), *also δ CH$_2$ | 1580, 1503*, 1485*, 1464*, 1439* | 1572, 1519, 1487, 1464*, 1450*, 1435* | 1581, 1515, 1500, 1473*, 1458* 1432* | 1602, 1569, 1506, 1489, 1442* |
| Pyrazole ring stretching mode | 1375 | 1402 | 1380 | 1379 |
| ν$_{as}$ & ν$_s$SO$_3$$^-$ | | | 1234, 1161 | 1260, 1174, 1163 |
| Pirymidine ring stretching modes | 1269, 1212 | 1270, 1227 | 1269 | 1227 |
| ν =C—Cl | 1092 | 1076 | 1086 | 1090 |
| Pyrazole & | 1006*, | 1008*, 987 | 1003*, | 1005*, |

TABLE 14C-continued

| | IR Bands (cm$^{-1}$) | | | |
|---|---|---|---|---|
| Spectral region | Sodium Salt | Hydrochloride Salt | Mesylate Salt | Tosylate Salt |
| Pyrimidine ring breathing modes, * also ν C—O (p-alcohol) | 974 | | 968 | 995, 978 |
| δ =CH(para-substituted benzene, also 4(6)-substituted pyrimidine | 855, 839, 822 | 855, 828 | 851, 827, 811 | 843, 813 |

Differences in the IR bands of the various crystalline forms of Compound 1 were observed. For example, differences can be observed in the ester carbonyl stretch of the Form I polymorph (about 1632 cm$^{-1}$), the Form II polymorph (about 1635 cm$^{-1}$), the Form III polymorph (about 1640 cm$^{-1}$), the acetic acid solvate (about 1719 cm$^{-1}$ for the acid and 1637 cm$^{-1}$ for the amide), the NMP solvate (about 1658 and 1642 cm$^{-1}$), the monohydrate crystalline form (about 1626 cm$^{-1}$), the crystalline sodium salt (about 1631 cm$^{-1}$), the hydrochloride salt (about 1645 and 1626 cm$^{-1}$), the mesylate salt (about 1645 and 1630 cm$^{-1}$), the tosylate salt (about 1629cm$^{-1}$) and a chloroform solution of Compound 1 (about 1640 cm$^{-1}$).

Figure 34:
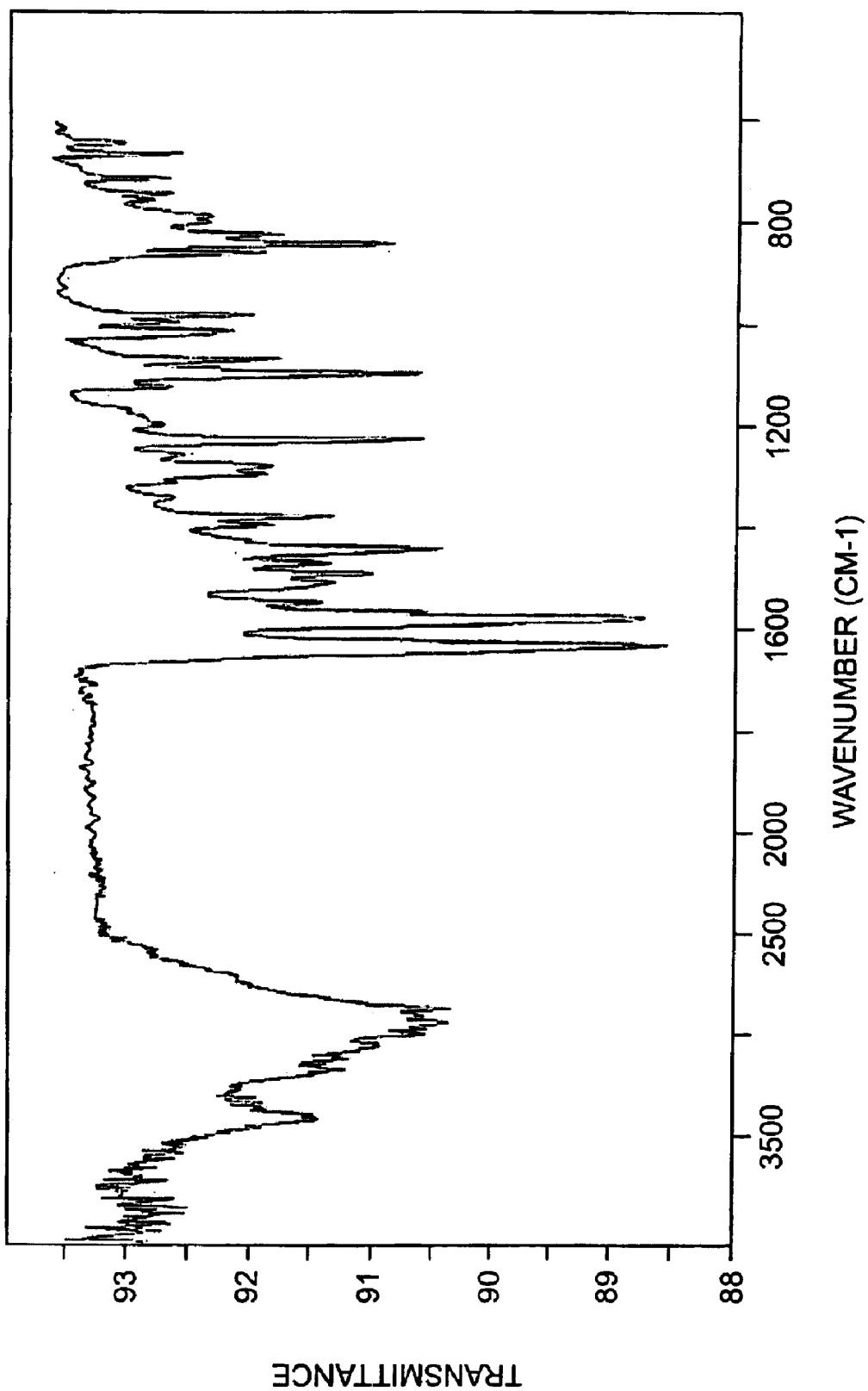
FIG. 34 shows an illustrative infrared (IR) spectrum (attenuated total reflectance, ATR) of the Form I polymorph of Compound 1.
Figure 35:
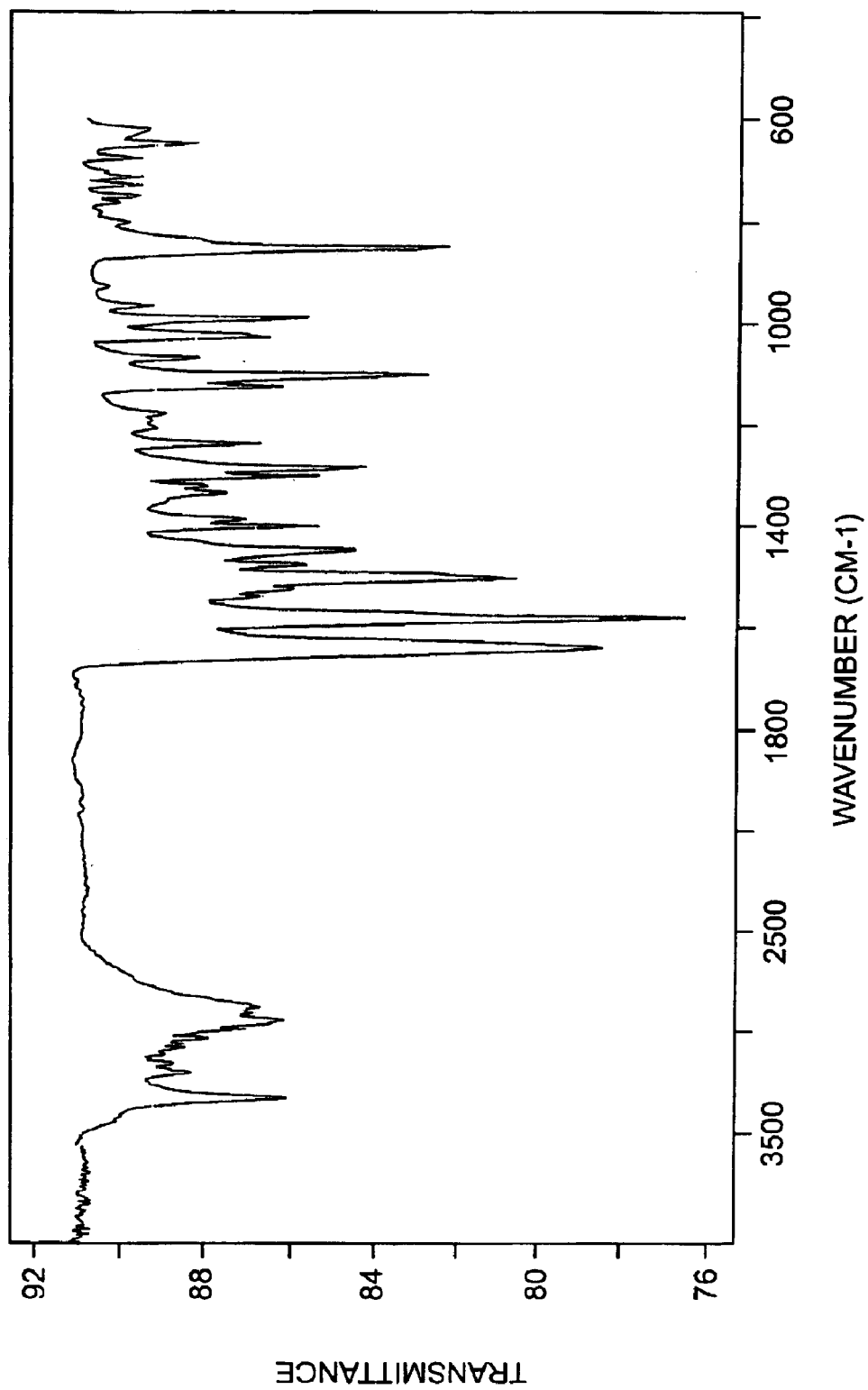
FIG. 35 shows an illustrative infrared (IR) spectrum (attenuated total reflectance, ATR) of the Form II polymorph of Compound 1.
Figure 36:
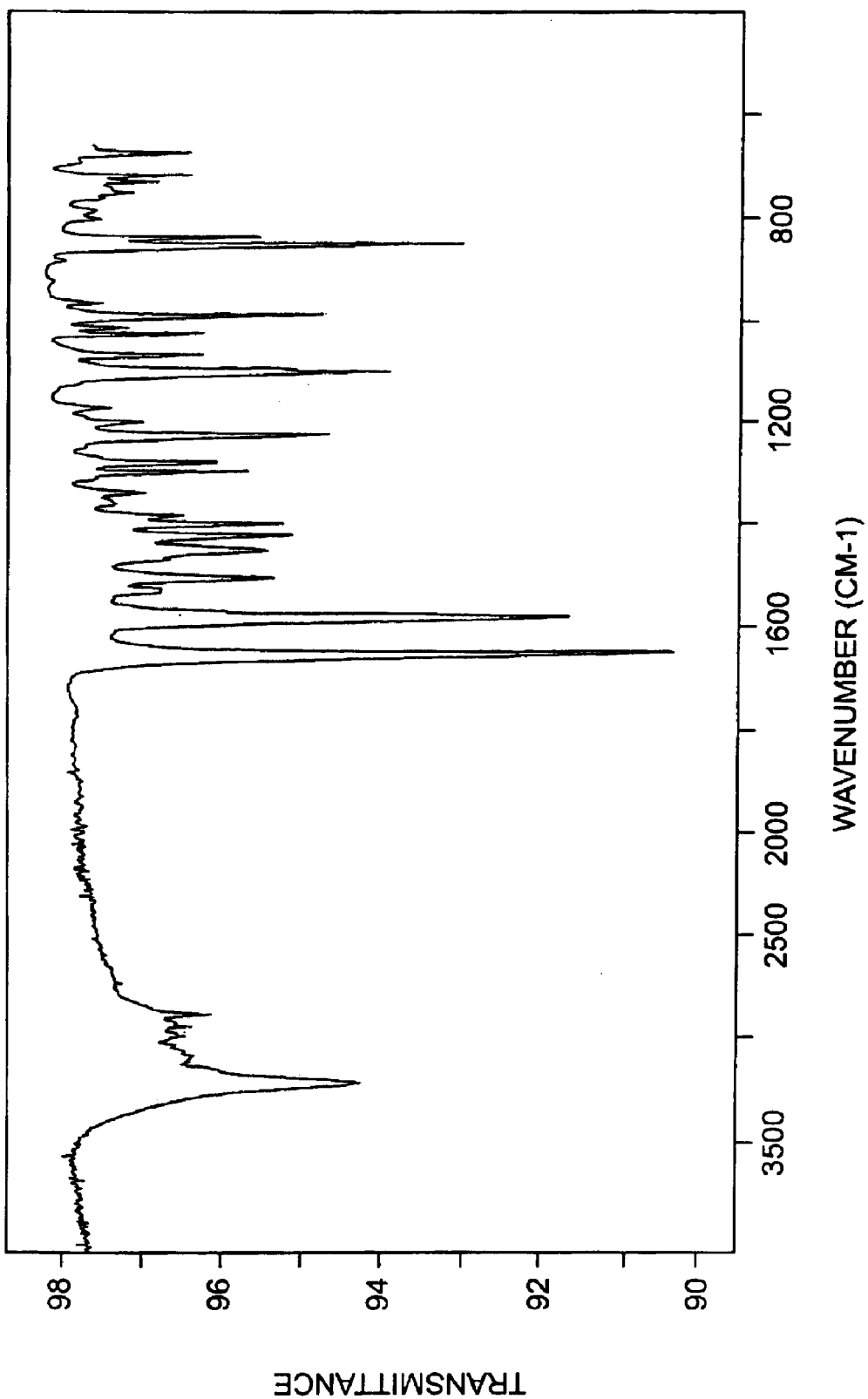
FIG. 36 shows an illustrative infrared (IR) spectrum (attenuated total reflectance, ATR) of the Form III polymorph of Compound 1.
Figure 37:
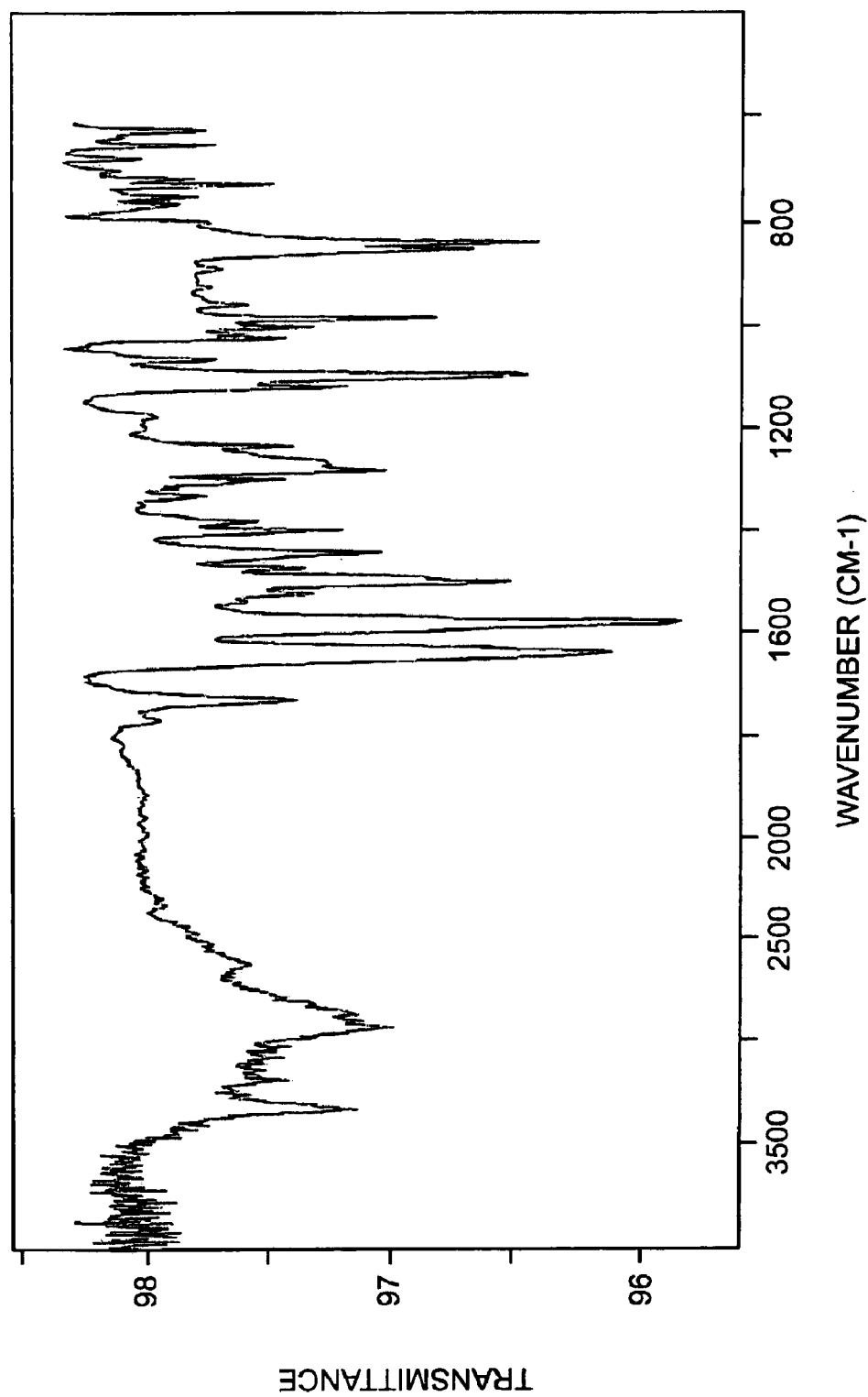
FIG. 37 shows an illustrative infrared (IR) spectrum (attenuated total reflectance, ATR) of the acetic acid solvate of Compound 1.
Figure 38:
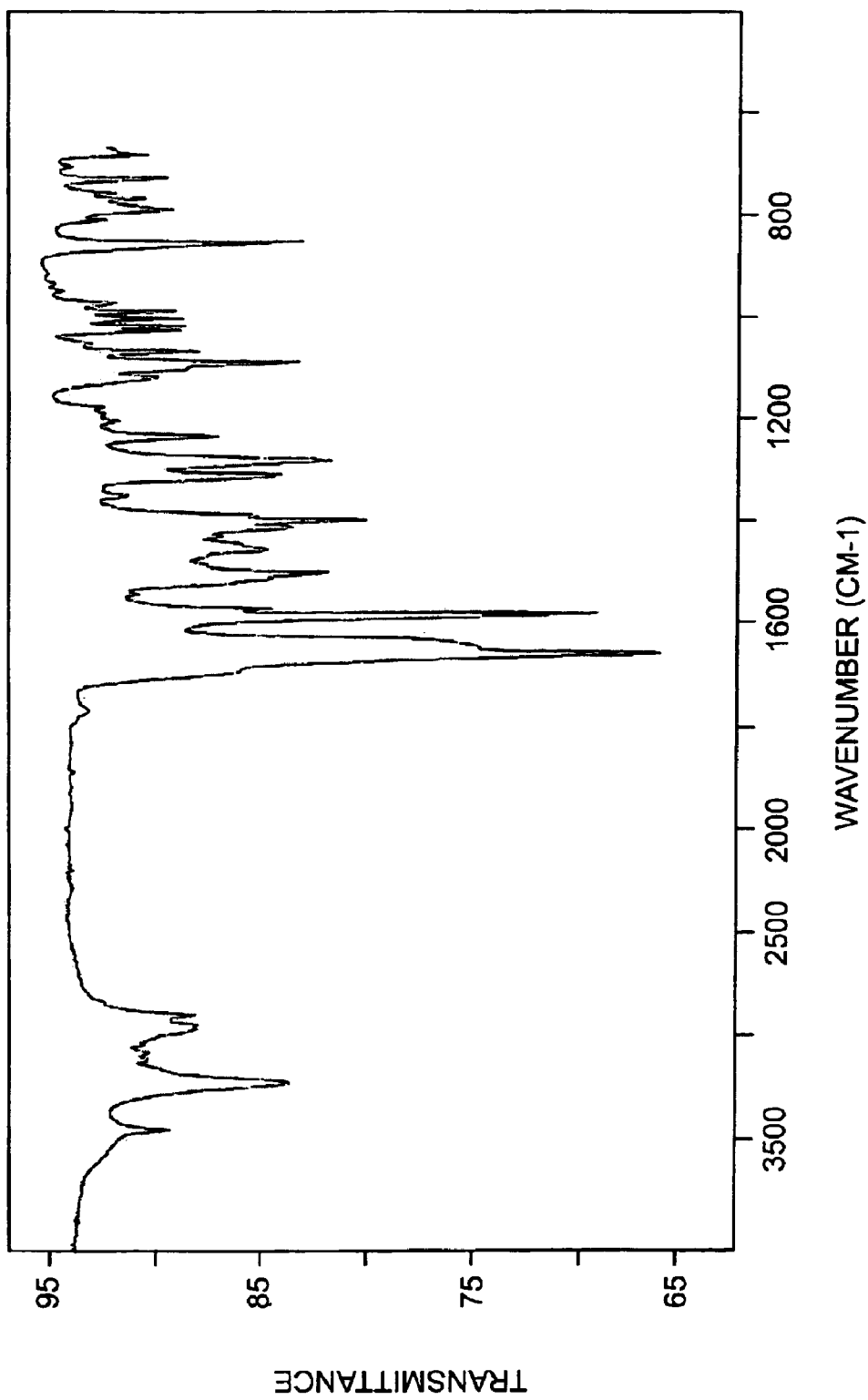
FIG. 38 shows an illustrative infrared (IR) spectrum (attenuated total reflectance, ATR) of the NMP solvate of Compound 1.
Figure 39:
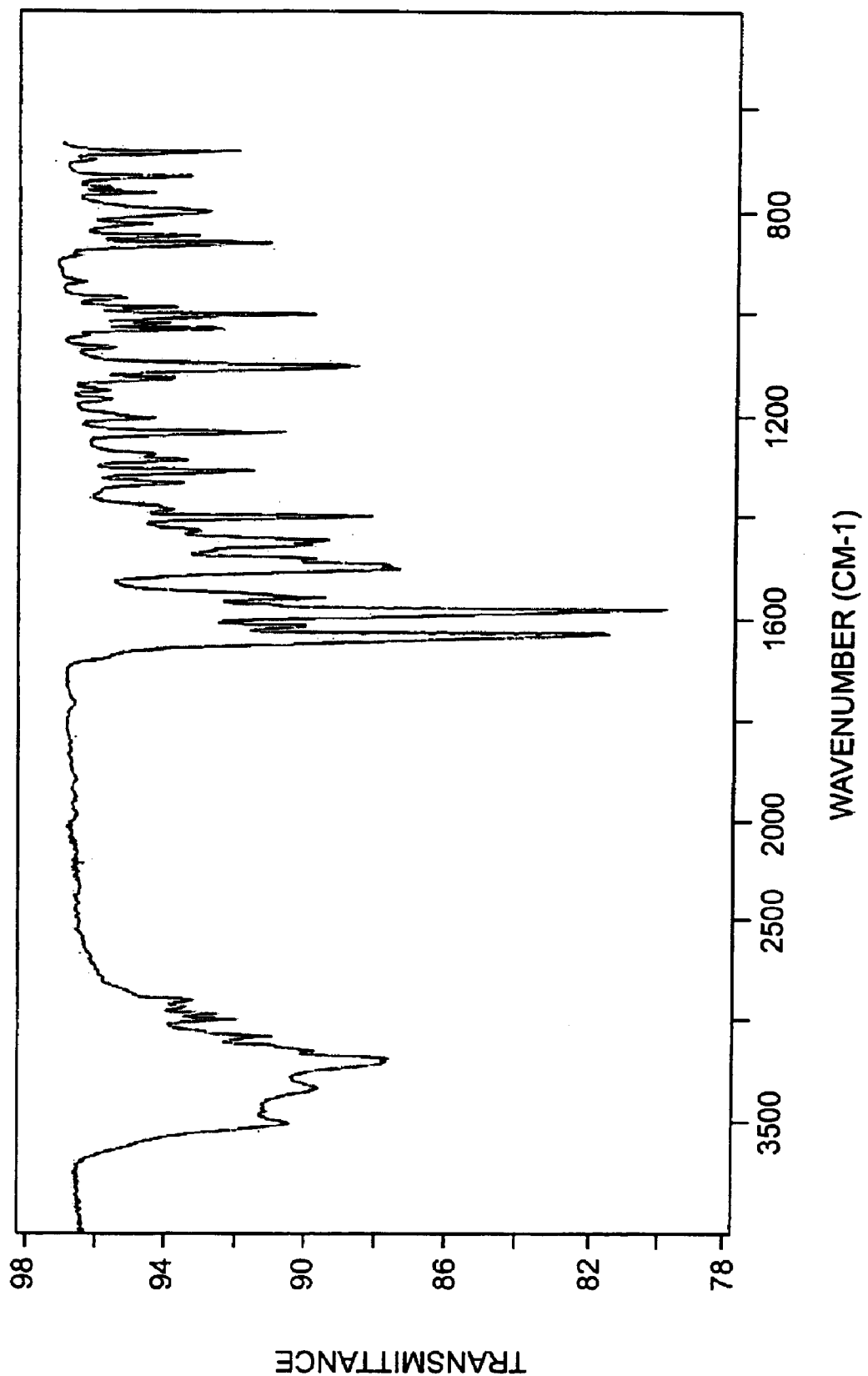
FIG. 39 shows an illustrative infrared (IR) spectrum (attenuated total reflectance, ATR) of the monohydrate crystalline form of Compound 1.
Figure 40:
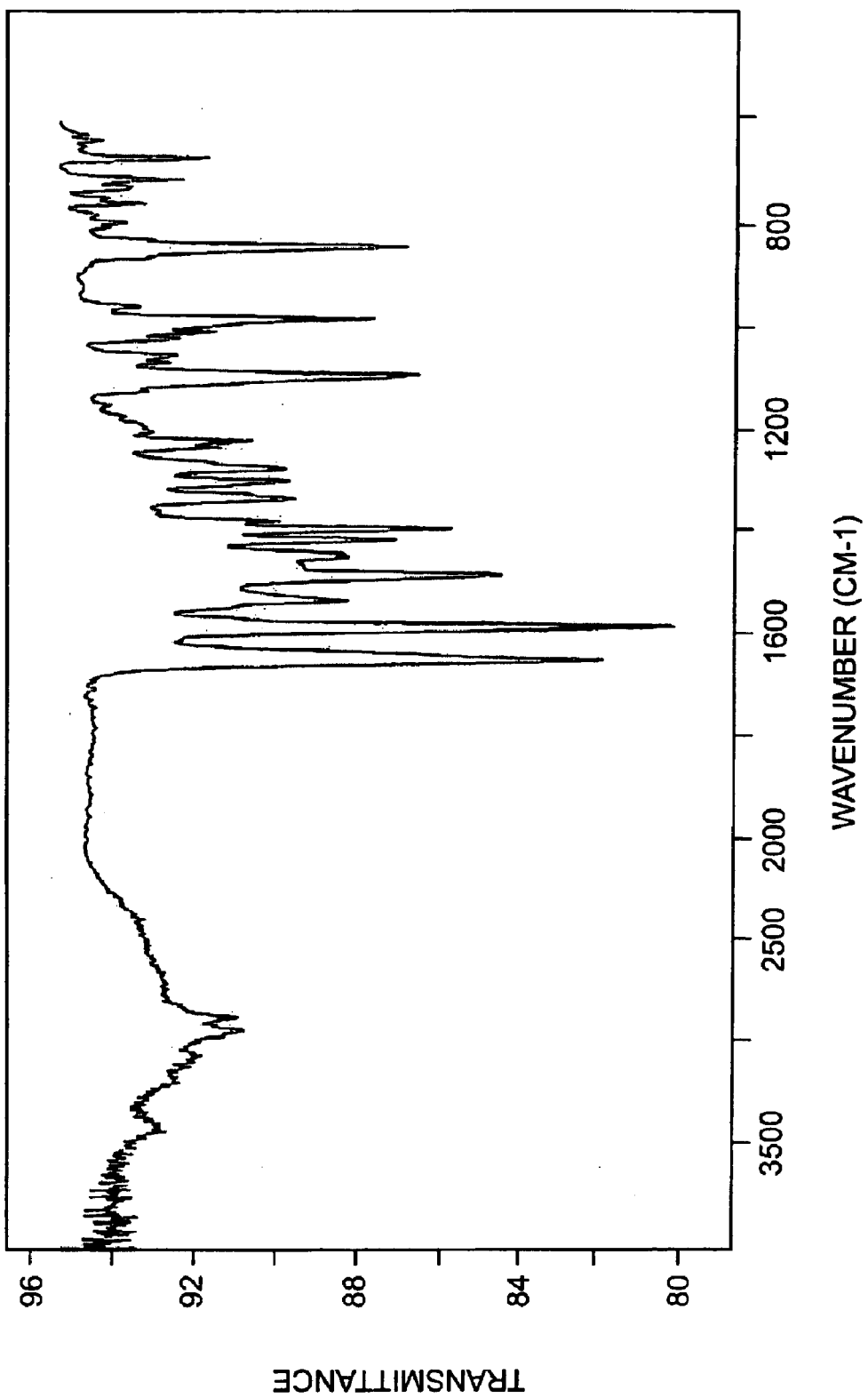
FIG. 40 shows an illustrative infrared (IR) spectrum (attenuated total reflectance, ATR) of the crystalline sodium salt of Compound 1.
Figure 41:
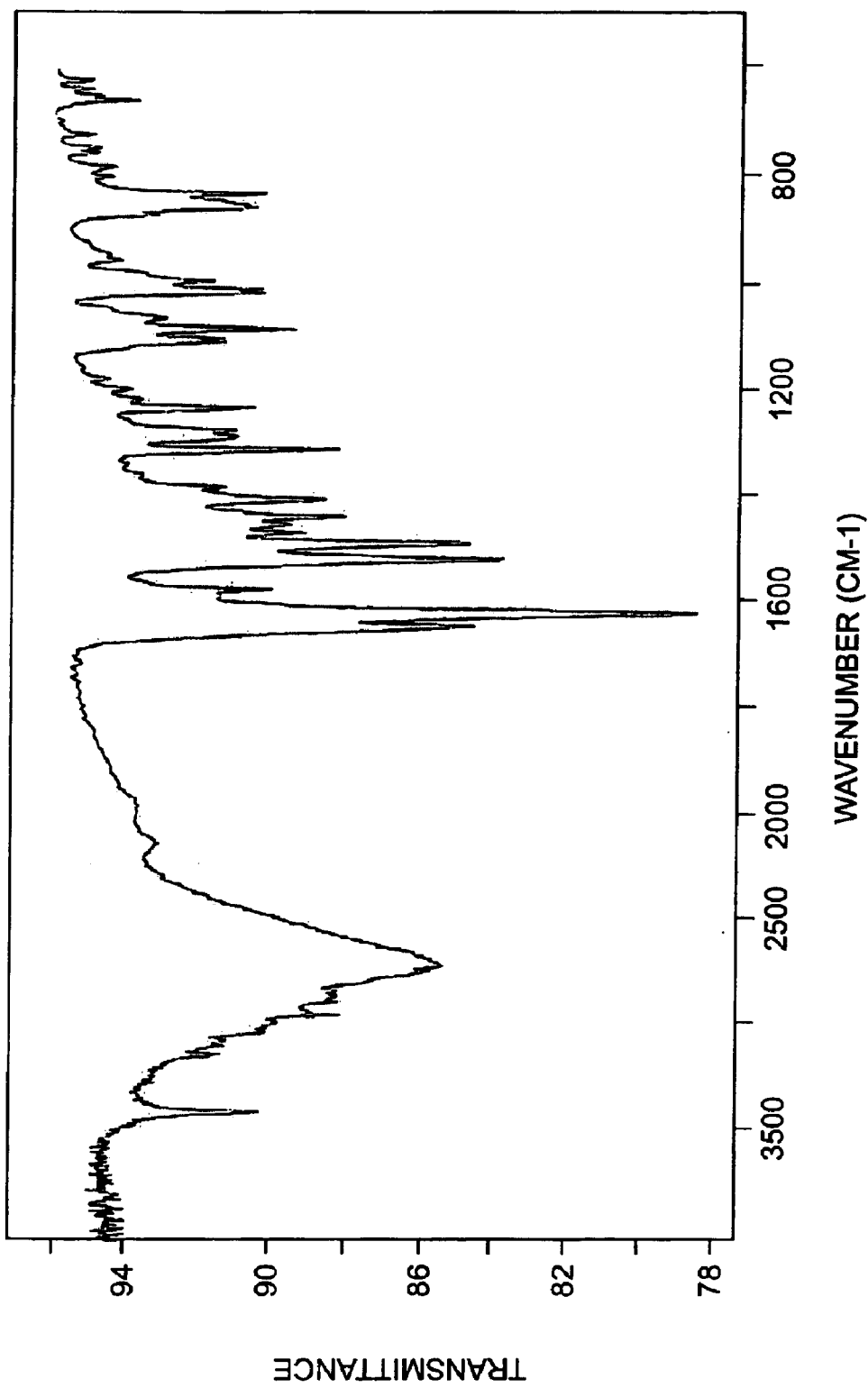
FIG. 41 shows an illustrative infrared (IR) spectrum (attenuated total reflectance, ATR) of the crystalline hydrochloride salt of Compound 1.
Figure 42:
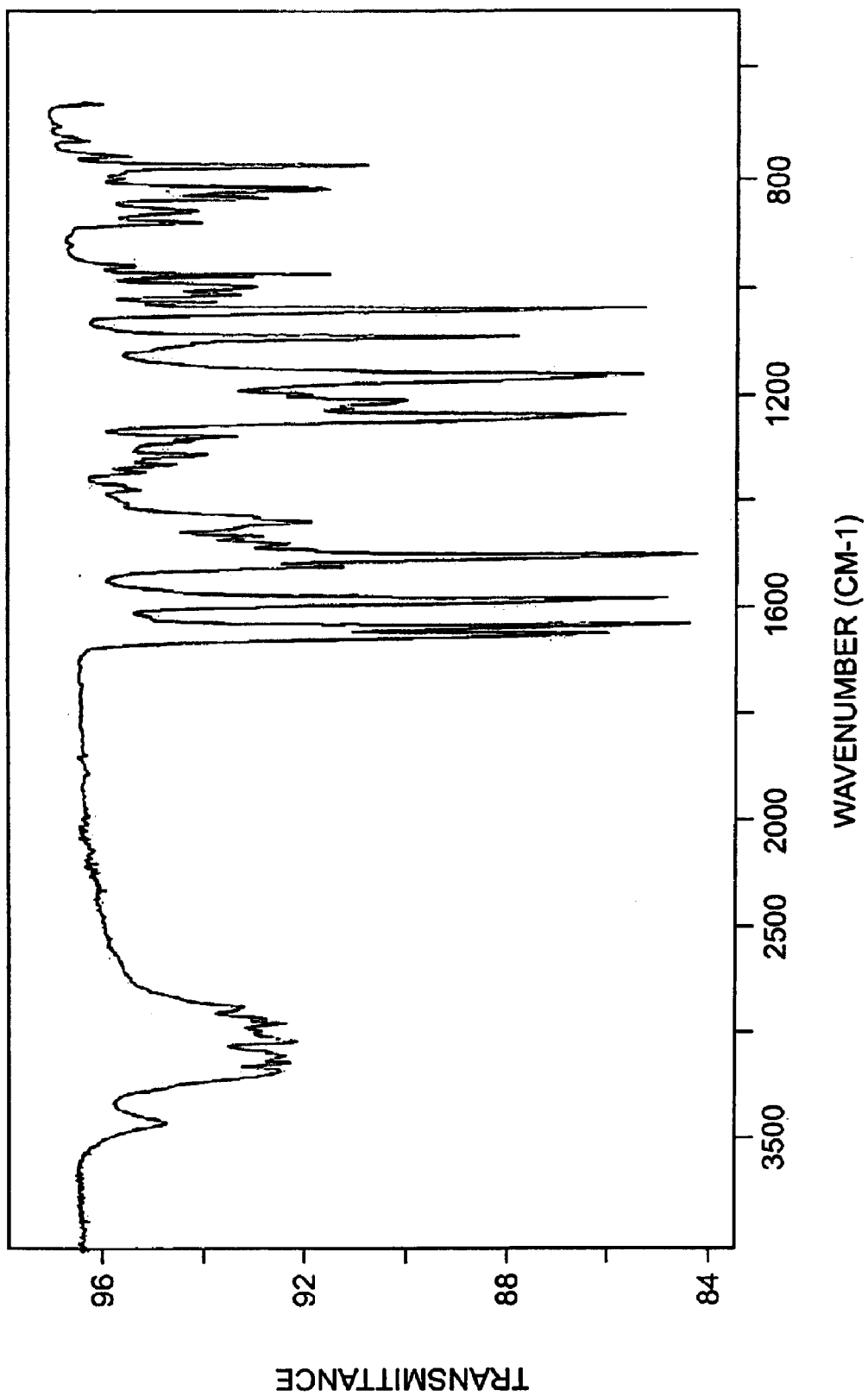
FIG. 42 shows an illustrative infrared (IR) spectrum (attenuated total reflectance, ATR) of the crystalline methanesulfonic acid (mesylate) salt of Compound 1.
Figure 43:
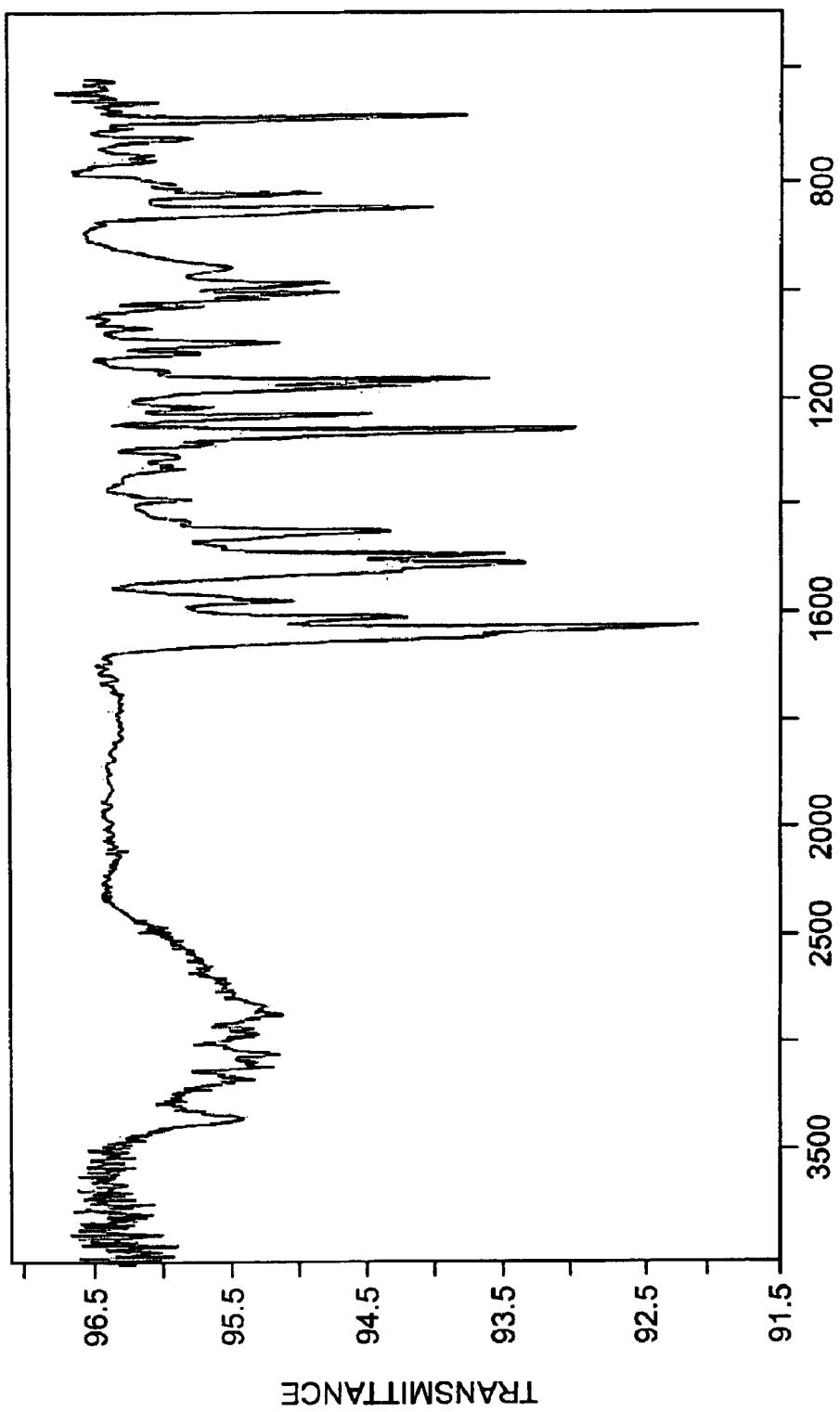
FIG. 43 shows an illustrative infrared (IR) spectrum (attenuated total reflectance, ATR) of the crystalline p-toluenesulfonic acid (tosylate) salt of Compound 1.

FIGS. 34–44 set forth typical infrared absorption band profiles for the following crystalline forms of Compound 1:

(1) FIG. 34 presents an infrared absorption band profile obtained for a sample of the Form I polymorph;

(2) FIG. 35 presents an infrared band profile obtained for a sample of the Form II polymorph;

(3) FIG. 36 presents an infrared band profile obtained for a sample of the Form III polymorph;

(4) FIG. 37 presents an infrared band profile obtained for a sample of the acetic acid solvate;

(5) FIG. 38 presents an infrared band profile obtained for a sample of the NMP solvate;

(6) FIG. 39 presents an infrared band profile obtained for a sample of the monohydrate crystalline form;

(7) FIG. 40 presents an infrared band profile obtained for a sample of the crystalline sodium salt of Compound 1;

(8) FIG. 41 presents an infrared band profile obtained for a sample of the crystalline hydrochloride salt of Compound 1;

(9) FIG. 42 presents an infrared band profile obtained for a sample of the crystalline mesylate salt of Compound 1;

(10) FIG. 43 presents an infrared band profile obtained for a sample of the crystalline tosylate salt of Compound 1; and

Figure 44:
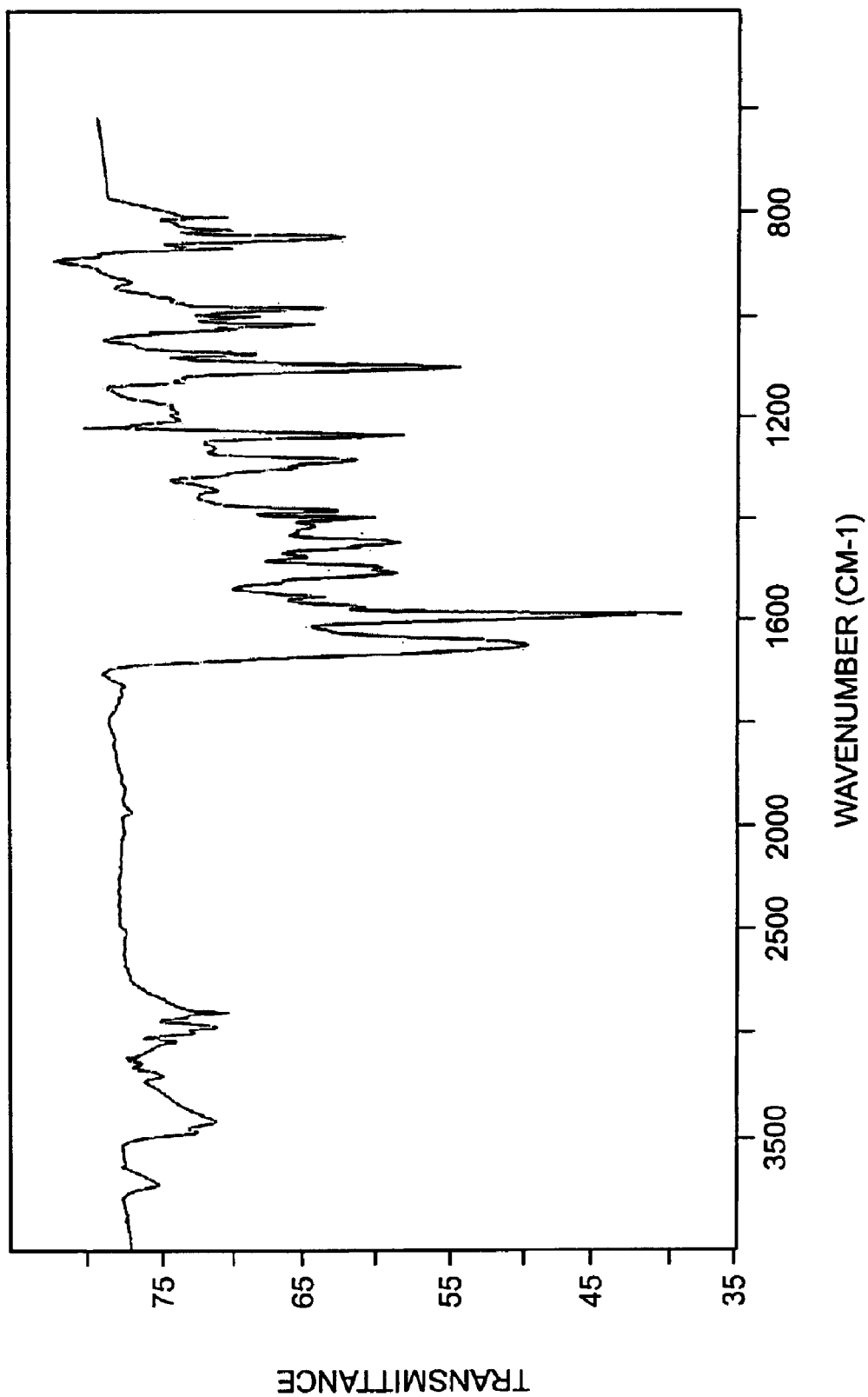
FIG. 44 shows an illustrative infrared (IR) spectrum (solution) of Compound 1 in chloroform.

(11) FIG. 44 presents an infrared band profile obtained for a sample of Compound 1 in chloroform solution.

6. Unit Cell Parameters

Table 15 below summarizes the unit cell parameters determined for the Form I polymorph, the dihydrate crystalline form and the NMP solvate.

TABLE 15

Unit Cell Parameters

| Parameter | Form I Polymorph | Dihydrate Crystalline Form | NMP Solvate |
|---|---|---|---|
| Crystal System | Triclinic | Triclinic | Monoclinic |
| Empirical Formula | C$_{20}$H$_{20}$N$_5$ClO$_2$ | C$_{20}$H$_{24}$N$_5$ClO$_4$ | C$_{25}$H$_{29}$N$_6$ClO$_3$ |
| Formula Weight | 397.86 | 433.89 | 496.99 |
| a (Å) | 6.3726 (3) | 9.0799 (6) | 11.4269(3) |
| b (Å) | 10.5558 (2) | 9.6863 (7) | 9.2313(2) |
| c (Å) | 14.5425 (6) | 12.8919 (9) | 22.5489(5) |
| α (°) | 78.406 (2) | 98.07 | 90.00 |
| β (°) | 78.336 (2) | 103.361 (2) | 98.8770(10) |
| γ (°) | 76.291 (2) | 105.656 (2) | 90.00 |
| Volume(Å$^3$), Z | 931.26 (6), 2 | 1037.06 (12), 2 | 2350.08 (10), 4 |
| Space Group | P – 1 (No. 2) | P – 1 (No. 2) | P2$_1$/c (No. 14) |

Preparation of Compound 1

The Compound 1 starting material (i.e., N-(2-hydroxyacetyl)-5-(4-piperidyl)-4-(4-pyrimidinyl)-3-(4-chlorophenyl)pyrazole) used to prepare the novel crystalline forms of the present invention can be synthesized by the methods set forth in the above-cited International Patent Publication No. WOOO/31067, particularly Examples D-1 and D-2 set forth in this publication.

Preparation of Solid-State Forms of Compound 1
Preparation of Solvated Crystalline Forms The solvated crystalline forms of Compound 1 can be prepared by crystallization of Compound 1 from a suitable solvent. Where the term solvent is used in this application, it can encompass either a single solvent or a mixture of solvents. A suitable solvent generally comprises an organic polar aprotic solvent and/or organic acid in which Compound 1 is substantially soluble at elevated temperature (generally a temperature of at least about 90° C. for organic acids and 115° C. for aprotic solvents), but which preferentially crystallizes the solvate upon cooling. The solubility of Compound 1 in the solvent at elevated temperature generally is sufficient to provide at least about a 10 weight percent solution, particularly at least about a 15 weight percent solution, and more particularly at least about a 20 weight percent solution, of Compound 1 in the solvent. The solubility of Compound 1 in the solvent at room temperature typically is less than about 5 weight percent, and commonly is in the range of about 0.1 to about 5 weight percent, particularly about 1 to about 3 weight percent. Suitable solvents from which solvates can be crystallized include acetic acid and N-methylpyrrolidone, and are hypothesized to include dimethylsulfoxide and dimethylformamide.

The amount of Compound 1 starting material added to the solvent generally will depend on the solubility of Compound 1 in the solvent selected. Typically, the amount of Compound 1 added to the solvent is an amount that will not materially solubilize in, and that will form a slurry with, the solvent at room temperature, but will substantially solubilize in the solvent at elevated temperature. The amount of Compound 1 starting material used will vary from solvent to solvent, but commonly will be up to about 25 weight percent, particularly about 10 to about 25 weight percent, and more particularly about 15 to about 25 weight percent of the resulting mixture.

Once Compound 1 has been added to the solvent, the mixture is heated until Compound 1 has substantially solubilized in the solvent. After Compound 1 has substantially solubilized in the solvent, the resulting solution is cooled. An illustrative but non-limiting cooling rate is 1° C./minute or less. It should be noted, however, that the duration, rate and amount of heating and cooling can vary widely without adversely affecting the crystallization although heating the mixture in a manner that leads to degradation of Compound 1 should be avoided.

The endpoint at which the solvated crystals of Compound 1 are harvested can vary and generally will depend upon the solubility curve of the solvent. For most of the solvents described herein, for example, a convenient illustrative endpoint is equal to or less than about 5° C. The solvated crystals can be harvested by conventional means such as, but not limited to, filtration or centrifugation.

Using an anti-solvent typically can enhance crystallization of Compound 1 solvates. Suitable anti-solvents include, but are not limited to, ethyl acetate, water, methanol and ethanol. The amount of anti-solvent, rate of addition, ratio of solvent to anti-solvent, and temperature can affect the crystalline form that results. For example, if anti-solvent is added quickly to a solution of Compound 1 in NMP resulting in about a 20 weight percent solution of anti-solvent, the crystalline form obtained typically is the NMP solvate. If, however, anti-solvent is added quickly to a solution of Compound 1 in NMP resulting in about a 50 weight percent solution of anti-solvent, the crystalline form obtained typically is the Form II polymorph. The Form I polymorph can be grown by refluxing the anti-solvent in the solvent containing a solid form of Compound 1 (such as the NMP solvate or the Form II polymorph). The reflux temperature depends on the solvent, although illustrative reflux temperatures include about 65° C. where methanol is the solvent and about 80° C. when ethanol is the solvent.

While anti-solvent addition may be helpful to increase yield, it is not an absolute requirement. As noted above, solvates can still be grown directly from pure solvent or slurry conversion without the use of anti-solvent addition 1. Preparation of Acetic Acid Solvate The acetic acid solvate of Compound 1 can be prepared, for example, by first solubilizing Compound 1 in acetic acid. The solubilization generally takes place at a temperature above 40° C., preferably at least above about 45° C., and more preferably at least above about 55° C. The weight fraction of Compound 1 in this mixture can vary widely, although about 10 weight percent to about 25 weight percent typically is a convenient range. Nucleation of the acetic acid solvate is thought to occur at a temperature of about 40° C. Accordingly, the acetic acid solution is cooled to about 40° C. and optionally held at that temperature for a period of time. A convenient, but non-limiting, cooling rate and holding period are about 1° C./minute and about one hour, respectively. After the initial optional holding period, the resulting slurry is further cooled to a lower temperature and optionally subjected to an additional holding period. This temperature and optional additional holding period preferably are coordinated to maximize the crystallization of the acetic acid solvate. For example, one convenient method is to cool the slurry to a temperature of about 0° C. and to maintain the slurry at that temperature until less than about 1 weight percent of Compound 1 is left in solution. Typically, this holding period is about 12 hours. Anti-solvent addition (such as with ethyl acetate in an amount up to about 60 weight percent) can improve crystallization yield.

An alternative route to prepare the acetic acid solvate is to slurry a second solid-state form of Compound 1, such as the Form II polymorph (the preparation of which is described below), in acetic acid under conditions suitable for the conversion of the second form to the acetic acid solvate. For purposes of illustration, but not limitation, such conversion can be carried out by preparing a slurry of the second form in acetic acid and maintaining that slurry at or below about 25° C. for at least about two hours or until the second form has substantially converted to the acetic acid solvate.

2. Preparation of NMP Solvate

The NMP solvate of Compound 1 can be prepared in essentially the same manner as described above for the acetic acid solvate with the exception that NMP is used as the solvent instead of acetic acid. The NMP solvate can be prepared, for example, by initially solubilizing Compound 1 in an NMP solution and cooling this solution, with or without seeding, until the NMP solvate crystallizes. The yield of this crystallization can be improved by using anti-solvent addition technology. For example, the NMP solvate can be advantageously crystallized from mixtures of NMP and an anti-solvent such as water (less than about 50 weight percent) comprising Compound 1.

In addition, it is hypothesized that the NMP solvate can be prepared from a second solid-state form of Compound 1 by dissolving or slurrying of that crystalline form in NMP at lower temperature (generally at or below about 25° C.).

Preparation of Form I Polymorph

1. Preparation of Form I Polymorph through Intermediate Salt

The Form I polymorph can be crystallized from solution by proceeding through an intermediate salt form of Compound 1. Compound 1 need not be soluble in the solvent selected (i.e., Compound 1 can be substantially present as a slurry of solids in the solvent) so long as, upon basification of the solvent, Compound 1 is converted to the corresponding base addition salt. Suitable solvents/slurry media typically include any solvent that is as polar or more polar than NMP. These include alcohols (such as methanol) or mixtures of an alcohol and a non-polar solvent (such as methanol and xylene). A suitable base is then added to the mixture of Compound 1 and solvent to form a base addition salt of Compound 1. The amount of base relative to Compound 1 typically is at least about 1 molar equivalent, particularly at least about 1.2 molar equivalents or higher.

Illustrative base addition salts that can be used include (but are not limited to) the sodium, potassium, calcium and magnesium salts of Compound 1. The formation of the base addition salt can be carried out in any convenient manner. Typically, a base such as an alkali metal hydroxide (for example, sodium hydroxide or potassium hydroxide), an alkaline earth metal hydroxide (for example, calcium hydroxide, magnesium hydroxide, and barium hydroxide), or a rare earth metal hydroxide is added to the mixture of Compound 1 and solvent.

Although a wide range of temperatures can be employed, the base addition reaction preferably is carried out at a low temperature below about 5° C. (such as about 0° C.). The pH of the mixture is then reduced with a mineral acid (such as hydrochloric acid or sulfuric acid) or an organic acid (such as acetic acid) thereby converting the Compound 1 salt back to the non-salt form of Compound 1. This step preferably is carried out at a low temperature (such as about 0° C.). In one embodiment, a substantially equivalent number of moles of acid are added (relative to base originally added) to neutralize the solvent system. The resulting mixture is then heated to a temperature (which will vary depending upon the solvent used) suitable to promote the conversion of Compound 1 to the Form I polymorph. Typically, the temperature of the mixture should be raised to at least about 40° C., preferably at least about 50° C., and more preferably at least about 65° C. It has been found that the rate of Form I crystal growth can be materially increased through this use of the intermediate salt and appropriate manipulation of pH. Cooling rate and heating rate are not narrowly critical.

2. Preparation of Form I Polymorph by Refluxing Second Solid-State Form

The Form I polymorph also can be prepared by refluxing a slurry of a second solid-state form of Compound 1 particularly the Form II polymorph) in a suitable solvent. Illustrative solvents include, but are not limited to, alcohols (such as methanol or ethanol). Typical refluxing time is about two hours or less. Once refluxing is discontinued, the solution is cooled (generally to a range between about 5° C. to about 25° C.) to yield the Form I polymorph. A cooling period of at least two hours generally is used to avoid the formation of the Form II polymorph. The cooling rate is not narrowly critical and can vary widely. One non-limiting illustrative cooling rate is about 0.3° C./minute.

3. Preparation of Form I Polymorph by Slurry Conversion

The more thermodynamically stable Form I polymorph can be prepared from a second solid-state form of Compound 1 (preferably selected from the group consisting of the amorphous form, the NMP solvate, the Form II polymorph, and combinations thereof) by slurrying the second form in a suitable solvent, preferably at an elevated temperature. Typically, the solvent is one in which Compound 1 has a solubility up to about 5 weight percent, particularly about 1 to about 3 weight percent, at room temperature, such as but not limited to ethers, combinations of ethers and other solvents, alcohols (such as methanol or ethanol), and combinations of alcohols and other solvents. For the NMP solvate, if the solvent system used includes NMP, at least one additional solvent will be present in a material amount. The slurry conversion may initially result in the formation of the Form II polymorph rather than the Form I polymorph. Allowing additional time for the conversion and/or adding heat generally converts any Form II polymorph present to the Form I polymorph. Accordingly, the slurry conversion process typically is carried out at a temperature in excess of about 50° C. to favor the formation of the Form I polymorph.

4. Preparation of Form I Polymorph From Hydrated Crystalline Forms

It is hypothesized that the Form I polymorph also can be prepared from the monohydrate crystalline form or the dihydrate crystalline form by refluxing a slurry of that crystalline form in a suitable solvent such as, for example, methanol.

5. Preparation of Form I Polymorph by Desolvation of NMP Solvate

It is further hypothesized that the Form I polymorph can be prepared directly from the NMP solvate by desolvation. Desolvation can be accomplished by any suitable desolvation means such as heating the solvate, reducing the ambient pressure surrounding the solvate or combinations thereof. The maximum temperature during desolvation generally does not exceed about 150° C. Conversion at one atmospheric pressure has been seen to occur at about 140° C. by DSC. The pressure under which the desolvation is carried out is not narrowly critical and typically is one atmosphere or less.

Preparation of Form II Polymorph

1. Preparation of Form II Polymorph by Slurry Conversion

The Form II polymorph can be prepared from the acetic acid solvate by slurrying the solvate, preferably at an elevated temperature, in a solvent in which Compound 1 has low solubility at room temperature, such as but not limited to ethyl acetate or combinations of ethyl acetate and other solvents. This process typically is carried out at a temperature in excess of about 50° C. Similarly, the Form II polymorph can be prepared from the NMP solvate by the addition of an anti-solvent to a slurry of the NMP solvate in a suitable solvent. A wide range of solvents can be used for the slurry conversion, including, but not limited to, ethyl acetate, combinations of ethyl acetate and other solvents, alcohols (such as methanol or ethanol), and combinations of alcohols and other solvents. The temperature at which the slurry conversion is conducted preferably is at least about 10° C. below the boiling temperature of the anti-solvent. While the slurry conversion can be carried out at a temperature in excess of about 50° C., lower temperatures or limited time at elevated temperatures may be preferable since the Form II polymorph is not the thermodynamically stable crystalline form. In fact, if the time during which the slurry conversion is conducted at elevated temperature exceeds the initial crystallization time, the Form I polymorph may result.

2. Preparation of Form II Polymorph by Desolvation of Acetic Acid Solvate

In addition, it is hypothesized that the Form II polymorph also can be prepared directly from the acetic acid solvate by desolvation. Desolvation can be accomplished by any suitable desolvation means such as heating the solvate, reducing the ambient pressure surrounding the solvate or combinations thereof. The maximum temperature during desolvation generally does not exceed about 100° C. to avoid undesired solid-state conversions and/or degradation of Compound 1. The pressure under which the desolvation is carried out is not narrowly critical and typically is one atmosphere or less.

Preparation of Form III Polymorph

1. Preparation of Form III Polymorph From Hydrated Crystalline Forms

The Form III polymorph can be prepared from a second solid-state form of Compound 1 (preferably selected from the group consisting of the monohydrate or dihydrate) by drying the solids preferably at a temperature at or below 50 degrees Celsius, under vacuum.

Preparation of Monohydrate and Dihydrate Crystalline Forms

1. Preparation of Monohydrate and Dihydrate Crystalline Forms Using Anti-Solvent Addition The monohydrate and dihydrate crystalline forms of Compound 1 can be prepared, for example, using anti-solvent addition technology. In one illustrative approach, an amount of Compound 1 (for example, an amount sufficient to form a 15 weight percent solution of Compound 1 in solvent) is first solubilized in acetic acid. This solubilization typically will take place at a higher than ambient temperature. A temperature of at least about 70° C., for example, should ensure that substantially all Compound 1 has been solubilized in the acetic acid. Water is then added to the acetic acid solution and the solution is cooled. The rate of cooling typically controls whether the crystalline form obtained is the monohydrate or the dihydrate crystalline form. A faster cooling rate favors the formation of the dihydrate crystalline form while a slower cooling rate favors the formation of the monohydrate crystalline form.

In an illustrative, but non-limiting, example for the preparation of the monohydrate crystalline form, a slurry of Compound 1 in acetic acid (an amount sufficient to form a 15 weight percent solution of Compound 1 in acetic acid) is heated to 90° C. to solubilize the Compound 1. A sufficient amount of water is then added to provide a 40/60 v/v solution of acetic acid/water. This solution is then cooled from about 90° C. to about 0° C. over a period of about six hours (i.e., about 15° C./hour) to yield the monohydrate crystalline form.

In an illustrative, but non-limiting, example for the preparation of the dihydrate crystalline form, a slurry of Compound 1 in acetic acid (an amount sufficient to form a 15 weight percent solution of Compound 1 in acetic acid) is heated to 90° C. to solubilize the Compound 1. A sufficient amount of water is then added to provide a 40/60 v/v solution of acetic acid/water. This solution is then cooled from about 90° C. to about 0° C. over a period of about three hours (i.e., about 30° C./hour) to yield the dihydrate crystalline form.

Alternatively, the acetic acid/water system can be replaced with another solvent/anti-solvent system such as an NMP/water anti-solvent system.

2. Preparation of Dihydrate Crystalline Form From Form II Polymorph

The dihydrate crystalline form of Compound 1 also can be prepared, for example, by slurry conversion of the Form II polymorph in a tetrahydrofuran/water mixture. A sufficient amount of the Form II polymorph is added to an 80:20 tetrahydrofuran/water mixture (volume basis) to form a saturated solution at 25° C. The solution then spontaneously desaturates by precipitating dihydrate crystals. Once precipitated, the dihydrate crystals eventually convert to the more thermodynamically stable Form I polymorph. This conversion, however, does not take place for about four days under the conditions described.

Preparation of Amorphous Form

1. Preparation of Amorphous Form by Lyophilization

It is hypothesized that the amorphous form of Compound 1 can be prepared by lyophilizing a solution, including a saturated solution, of Compound 1.

2. Preparation of Amorphous Form by Rapid Cooling

It is also hypothesized that the amorphous form of Compound 1 can be prepared by rapid cooling of a solution, including a saturated solution, of Compound 1. Such rapid cooling can be performed by a number of methods, well known by one of ordinary skill in the art. A non-limiting example would be to immerse a vessel containing a solution of Compound 1 in a dewar flask containing liquid nitrogen.

3. Preparation of Amorphous Form by Mechanical Means

It is also hypothesized that the amorphous form of Compound 1 can be prepared from another solid-state form of Compound 1, by grinding the solid state material in an apparatus such as a standard mortar and pestle.

The processes discussed above for preparing the various crystalline forms of Compound 1 can be combined in sequences or cycles that further enhance the purification of the final crystalline form product. For example, conversion of the Form I polymorph to the NMP solvate followed by the conversion of that NMP solvate back to the Form I polymorph can materially increase the purity of the Form I polymorph obtained relative to the original Form I polymorph starting material.

Product-by-Process Crystalline Forms

Embodiments of the present invention also include specific crystalline forms of Compound 1 and combinations thereof prepared in accordance with the processes disclosed in this application. In one embodiment, for example, the invention comprises the Form I polymorph of Compound 1, alone or in combination with one or more additional solid-state forms (including the Form II polymorph, the Form III polymorph, the solvated crystalline forms of Compound 1, the hydrated crystalline forms of Compound 1, the crystalline salts of Compound 1, and amorphous Compound 1) prepared as set forth in this application. In another embodiment, the invention comprises the Form II polymorph of Compound 1, alone or in combination with one or more additional solid-state forms (including the Form I polymorph, the Form III polymorph, the solvated crystalline forms of Compound 1, the hydrated crystalline forms of Compound 1, the crystalline salts of Compound 1, and amorphous Compound 1) prepared as set forth in this application. In another embodiment, the invention comprises the Form III polymorph of Compound 1, alone or in combination with one or more additional solid-state forms (including the Form I polymorph, the Form II polymorph, the solvated crystalline forms of Compound 1, the hydrated crystalline forms of Compound 1, the crystalline salts of Compound 1, and amorphous Compound 1) prepared as set forth in this application. Other embodiments of the invention are directed, for example, to the solvated or hydrated crystalline forms of Compound 1, or the crystalline salt forms, useful as intermediates in preparation of Form I polymorph and/or Form II and/or Form III polymorph, and prepared as set forth in this application.

Compound 1 Particle Size

The above solid-state forms of Compound 1 and combinations thereof can embrace a broad range of Compound 1 particle sizes. Based on drug product processing and bioavailability considerations, however, it is generally desirable to use a solid-state form of Compound 1 having a $D_{90}$ particle size of less than about 400 microns. This $D_{90}$ particle size can be measured as either the $D_{90}$, particle size of unformulated Compound 1 used as a starting material in preparing a pharmaceutical composition or the $D_{90}$ particle size of Compound 1 as formulated in a pharmaceutical composition. In one embodiment, the $D_{90}$ particle size is less than about 400 microns. In another embodiment, the $D_{90}$ particle size is less than about 300 microns. In still another embodiment, the $D_{90}$ particle size is less than about 200 microns. In still another embodiment, the $D_{90}$ particle size is less than about 150 microns. In still another embodiment, the $D_{90}$ particle size is less than about 100 microns. In still another embodiment, the $D_{90}$ particle size is less than about 50 microns. In still another embodiment, the $D_{90}$ particle size is between about 1 micron and about 400 microns. In another embodiment, the $D_{90}$ particle size is between about 1 micron and about 300 microns. In still another embodiment, the $D_{90}$ particle size is between about 1 micron and about 200 microns. In still another embodiment, the $D_{90}$ particle size is between about 1 micron and about 150 microns. In still another embodiment, the $D_{90}$ particle size is between about 1 micron and about 100 microns. In still another embodiment, the $D_{90}$ particle size is between about 1 micron and about 50 microns.

Any milling, grinding, micronizing or other particle size reduction method known in the art can be used to bring the crystalline form of Compound 1 into any desired size range as set forth above. For example, air-jet or milling can be effective for this purpose.

Where higher bioavailability is desired with less regard to cost, it is hypothesized that reduction of the particle size of a solid state form of Compound 1 to a $D_{90}$ particle size of less than about 1 micron can further enhance the bioavailability of unformulated Compound 1 and of pharmaceutical compositions comprising that solid state form of Compound 1, even by comparison with $D_{90}$ particle size ranges defined above. In one embodiment, therefore, the $D_{90}$, particle size is less than about 1 micron. In another embodiment, the $D_{90}$ particle size is less than about 800 nm. In still another embodiment, the $D_{90}$, particle size is less than about 600 nm. In still another embodiment, the $D_{90}$ particle size is less than about 500 nm. In still another embodiment, the $D_{90}$ particle size is between about 100 nm and about 1 micron. In still another embodiment, the $D_{90}$ particle size is between about 500 nm and about 1 micron. In still another embodiment, the $D_{90}$ particle size is between about 600 nm and about 1 micron. In still another embodiment, the $D_{90}$ particle size is between about 800 nm and about 1 micron.

Solid state forms of Compound 1 having a $D_{90}$ particle size less than about 1 micron can be prepared in accordance with applicable particle size reduction techniques known in the art. Such techniques include, but are not limited to, those described in the following patents and publications, each of which is incorporated herein by reference.

U.S. Pat. No. 4,826,689 to Violanto & Fischer.
U.S. Pat. No. 5,145,684 to Liversidge et al.
U.S. Pat. No. 5,298,262 to Na & Rajagopalan.
U.S. Pat. No. 5,302,401 to Liversidge et al.
U.S. Pat. No. 5,336,507 to Na & Rajagopalan.
U.S. Pat. No. 5,340,564 to Illig & Sarpotdar.
U.S. Pat. No. 5,346,702 to Na & Rajagopalan.
U.S. Pat. No. 5,352,459 to Hollister et al.
U.S. Pat. No. 5,354,560 to Lovrecich.
U.S. Pat. No. 5,384,124 to Courteille et al.
U.S. Pat. No. 5,429,824 to June.
U.S. Pat. No. 5,503,723 to Ruddy et al.
U.S. Pat. No. 5,510,118 to Bosch et al.
U.S. Pat. No. 5,518,187 to Bruno et al.
U.S. Pat. No. 5,518,738 to Eickhoff et al.
U.S. Pat. No. 5,534,270 to De Castro.
U.S. Pat. No. 5,536,508 to Canal et al.
U.S. Pat. No. 5,552,160 to Liversidge et al.
U.S. Pat. No. 5,560,931 to Eickhoff et al.
U.S. Pat. No. 5,560,932 to Bagchi et al.
U.S. Pat. No. 5,565,188 to Wong et al.
U.S. Pat. No. 5,569,448 to Wong et al.
U.S. Pat. No. 5,571,536 to Eickhoff et al.
U.S. Pat. No. 5,573,783 to Desieno & Stetsko.
U.S. Pat. No. 5,580,579 to Ruddy et al.
U.S. Pat. No. 5,585,108 to Ruddy et al.
U.S. Pat. No. 5,587,143 to Wong.
U.S. Pat. No. 5,591,456 to Franson et al.
U.S. Pat. No. 5,622,938 to Wong.
U.S. Pat. No. 5,662,883 to Bagchi et al.
U.S. Pat. No. 5,665,331 to Bagchi et al.
U.S. Pat. No. 5,718,919 to Ruddy et al.
U.S. Pat. No. 5,747,001 to Wiedmann et al.
International Patent Publication No. WO 93/25190.
International Patent Publication No. WO 96/24336.
International Patent Publication No. WO 98/35666.

In an illustrative process, coarse solid state Compound 1 is added to a liquid medium in which it is essentially insoluble to form a premix suspension. The concentration of the Compound 1 in the liquid medium can vary from about 0.1% to about 60%, and preferably is about 5% to about 30%, by weight. The apparent viscosity of the premix suspension is preferably less than about 1000 cP.

The premix can be directly subjected to mechanical means, for example using a ball mill, to reduce the $D_{90}$ particle size of Compound 1 to a desired range. Alternatively, the premix can first be agitated, e.g., using a roller mill or a Cowles type mixer, until a homogeneous dispersion is observed in which there are no large agglomerates visible to the naked eye, and then subjected to attrition, for example using a recirculating media mill.

The particles can be milled in presence of a surface modifying agent, for example a polymer or wetting agent. Alternatively, the particles can be contacted with a surface modifying agent after attrition. The surface modifying agent can reduce agglomeration of the particles, and have other benefits.

The particles should be reduced in size at a temperature that does not significantly degrade Compound 1. Processing temperatures of less than about 30–40° C. are ordinarily preferred. If desired, the processing equipment can be cooled with conventional cooling equipment. The method is conveniently carried out at ambient temperature and at processing pressures that are safe and effective for the milling process. For example, ambient processing pressures are typical of ball mills, attritor mills and vibratory mills. Control of the temperature can be achieved by jacketing or immersion of the milling chamber in ice water. Processing pressures from about 0.07 to about 3.5 $kg/cm^2$ are contemplated, with pressures of about 0.7 to 1.4 $kg/cm^2$ being typical.

After milling is completed, the grinding medium is separated from milled product, in either a dry or liquid dispersion form, using conventional separation techniques, such as filtration, sieving through a mesh screen or the like.

Combinations of Solid-State Forms

The present invention also is directed to combinations comprising a first solid-state form of Compound 1 and a second solid-state form of Compound 1, wherein the first solid-state form is selected from the Form I polymorph, the Form II polymorph, the Form III polymorph, the solvated crystalline forms of Compound 1, the hydrated crystalline forms of Compound 1, and the crystalline salts of Compound 1, and the second solid-state form of Compound 1 is selected differentially from the Form I polymorph, the Form II polymorph, the Form III polymorph, the solvated crystalline forms of Compound 1, the hydrated crystalline forms of Compound 1, the crystalline salts of Compound 1, and amorphous Compound 1.

Any suitable weight ratio of the first to the second solid-state form can be used. Suitable weight ratios of the first to the second solid-state form generally will range, for example, from about 1:99 to about 99:1, about 5:95 to about 95:5, about 1:9 to about 9:1, about 1:5 to about 5:1, about 1:3 to about 3:1, or about 1:2 to about 2:1. In various embodiments of the present invention, for example, the weight ratio of the first to the second solid-state form is about 99:1, about 98:2, about 97:3, about 96:4, about 95:5, about 94:6, about 93:7, about 92:8, about 91:9, about 90:10, about 85:15, about 80:20, about 75:25, about 70:30, about 65:35, about 60:40, about 55:45, or about 1:1.

In one embodiment, the first solid-state form is the Form I polymorph and the second solid-state form is selected from the group consisting of the Form II polymorph, the Form III polymorph, the solvated crystalline forms of Compound 1, the hydrated crystalline forms of Compound 1, and the crystalline salts of Compound 1.

In another embodiment, the first solid-state form is the Form II polymorph and the second solid-state form is selected from the group consisting of the Form I polymorph, the Form III polymorph, the solvated crystalline forms of Compound 1, the hydrated crystalline forms of Compound 1, and the crystalline salts of Compound 1.

In another embodiment, the first solid-state form is the Form III polymorph and the second solid-state form is selected from the group consisting of the Form I polymorph, the Form II polymorph, the solvated crystalline forms of Compound 1, the hydrated crystalline forms of Compound 1, and the crystalline salts of Compound 1.

In another embodiment, the first solid-state form is the Form I polymorph and the second solid-state form is the Form II polymorph or the Form III polymorph.

In another embodiment, a third solid-state form is also present.

Pharmaceutical Compositions

The present invention is further directed to pharmaceutical compositions comprising at least one crystalline form of Compound 1. In one embodiment, the pharmaceutical composition comprises (i) the Form I polymorph, optionally together with one or more additional solid-state forms of Compound 1 selected from the group consisting of the Form II polymorph, the Form III polymorph, the solvated crystalline forms of Compound 1, the hydrated crystalline forms of Compound 1, the crystalline salts of Compound 1, and amorphous Compound 1, and (ii) one or more pharmaceutically acceptable carriers and/or diluents and/or adjuvants (collectively referred to herein as "excipients") and, optionally, (iii) one or more active ingredients other than Compound 1.

In another embodiment, essentially the entire amount of Compound 1 contained in the composition is present as substantially phase pure Form I polymorph; however, if a combination of solid-state forms is present, preferred weight ratios of solid-state forms are as set out below.

In another embodiment, the pharmaceutical composition comprises (i) the Form II polymorph, optionally together with one or more additional solid-state forms of Compound 1 selected from the group consisting of the Form I polymorph, the Form III polymorph, the solvated crystalline forms of Compound 1, the hydrated crystalline forms of Compound 1, the crystalline salts of Compound 1, and amorphous Compound 1, and (ii) one or more pharmaceutically acceptable excipients, and, optionally, (iii) one or more active ingredients other than Compound 1.

In another embodiment, essentially the entire amount of Compound 1 contained in the composition is present as substantially phase pure Form II polymorph; however, if a combination of solid-state forms is present, preferred weight ratios of solid-state forms are as set out below.

In another embodiment, the first pharmaceutical composition comprises the Form I polymorph and the Form II polymorph of Compound 1.

In another embodiment, the pharmaceutical composition comprises (i) the Form III polymorph, optionally together with one or more additional solid-state forms of Compound 1 selected from the group consisting of the Form I polymorph, the Form II polymorph, the solvated crystalline forms of Compound 1, the hydrated crystalline forms of Compound 1, the crystalline salts of Compound 1, and amorphous Compound 1, and (ii) one or more pharmaceutically acceptable excipients, and, optionally, (iii) one or more active ingredients other than Compound 1.

In another embodiment, essentially the entire amount of Compound 1 contained in the composition is present as substantially phase pure Form III polymorph; however, if a combination of solid-state forms is present, preferred weight ratios of solid-state forms are as set out below.

In other embodiments, essentially the entire amount of Compound 1 contained in the composition is present as a substantially phase pure solvated crystalline form of Compound 1, a phase pure hydrated form of Compound 1, or a phase pure crystalline salt of Compound 1.

In still another embodiment of the invention, the composition comprises two solid-state forms of Compound 1, at least one of which is a crystalline form of Compound 1. The weight ratio of the first solid-state form to the second solid-state form in the composition generally will range, for example, from about 1:99 to about 99:1, about 5:95 to about 95:5, about 1:9 to about 9:1, about 1:5 to about 5:1, about 1:3 to about 3:1, or about 1:2 to about 2:1. In various embodiments of the present invention, for example, the weight ratio of the first to the second solid-state form in the composition is about 99:1, about 98:2, about 97:3, about 96:4, about 95:5, about 94:6, about 93:7, about 92:8, about 91:9, about 90:10, about 85:15, about 80:20, about 75:25, about 70:30, about 65:35, about 60:40, about 55:45, or about 1:1.

Compositions of the invention can be adapted to any suitable route of administration, including without limitation oral, buccal, sublingual, parenteral, e.g., intravascular, intraperitoneal, subcutaneous or intramuscular, topical and rectal (e.g., by suppository) routes. These compositions comprise Compound 1 in a desired amount in combination with one or more pharmaceutically-acceptable excipients appropriate to the desired route of administration.

The compositions of the invention generally can be presented in a dosage form containing about 0.1 mg to about 1000 mg of one or more crystalline forms of Compound 1. In other embodiments, the dosage form contains about 0.2 mg to about 600 mg, about 0.3 mg to about 250 mg, about 0.4 mg to about 150 mg, about 0.5 mg to about 100 mg, about 0.6 mg to about 50 mg, about 0.7 mg to about 25 mg, about 0.8 mg to about 15 mg, about 0.9 mg to about 10 mg, or about 1 mg to about 5 mg of one or more crystalline forms of Compound 1. In still other embodiments, the dosage form contains less than about 100 mg, less than about 75 mg, less than about 50 mg, less than about 25 mg, or less than about 10 mg of one or more crystalline forms of Compound 1.

Illustrative non-limiting dosage unit forms of the pharmaceutical compositions can typically contain, for example, 0.1, 0.2, 0.5, 1, 2, 3, 4, 5, 6, 7, 8, 9 10, 20, 25, 30, 37.5, 40, 50, 75, 100, 125, 150, 175, 200, 250, 300, 350 or 400 mg of one or more crystalline forms of Compound 1.

Methods of Treatment and/or Prophylaxis

The present invention also embraces a method for treatment and/or prophylaxis of a p38 kinase-mediated condition, the method comprising treating a subject having or susceptible to such condition or disorder with a therapeutically effective amount of a solid-state form of Compound 1 or a pharmaceutical composition containing a solid-state form of Compound 1.

In one embodiment, at least a detectable fraction of Compound 1 is present in the form of the Form I polymorph, the balance comprising one or more of the Form II polymorph, the Form III polymorph, the solvated crystalline forms of Compound 1, the hydrated crystalline forms of Compound 1, the crystalline salts of Compound 1, and amorphous Compound 1.

In another embodiment, at least a detectable fraction of Compound 1 is present in the form of the Form II polymorph, the balance comprising one or more of the Form I polymorph, the Form III polymorph, the solvated crystalline forms of Compound 1, the hydrated crystalline forms of Compound 1, the crystalline salts of Compound 1, and amorphous Compound 1.

In another embodiment, at least a detectable fraction of Compound 1 is present in the form of the Form III polymorph, the balance comprising one or more of the Form I polymorph, the Form II polymorph, the solvated crystalline forms of Compound 1, the hydrated crystalline forms of Compound 1, the crystalline salts of Compound 1, and amorphous Compound 1.

Such a method is useful for treatment and/or prophylaxis of a condition in a subject where administration of a p38 kinase inhibitor is indicated, including, but not limited to, treatment of those conditions previously disclosed above.

Besides being useful for human treatment, the solid-state forms of Compound 1 and pharmaceutical compositions thereof are also useful for veterinary treatment of companion, exotic and farm animals, for example horses, dogs, and cats.

The solid-state forms of Compound 1 and compositions thereof also can be used (i) in therapies partially or completely in place of other anti-inflammatory drugs, and/or (ii) in combination therapies with other drugs. Such anti-inflammatory and other drugs may include, but are not limited to, steroids, cyclooxygenase-2 inhibitors, DMARD's, immunosuppressive agents, NSAIDs, 5-lipoxygenase inhibitors, $LTB_4$ antagonists and $LTA_4$ hydrolase inhibitors. The phrase "combination therapy" embraces administration of each drug in a sequential manner in a regimen that will provide beneficial effects of the drug combination, as well as co-administration of the drugs in a substantially simultaneous manner, such as in a single capsule or injection having a fixed ratio of these active agents or in multiple, separate dosage forms or injections, one for each agent.

EXAMPLES

The following Examples contain detailed descriptions of methods of preparation of various crystalline forms of Compound 1 described herein. These detailed descriptions fall within the scope of the invention and illustrate the invention without in any way restricting that scope. All percentages are by weight unless otherwise indicated. Unless otherwise stated, the Compound 1 starting material used in each of the following Examples is prepared in accordance with Example D-1 or D-2 of the above-cited International Patent Publication No. WO 00/31063.

Example 1
Preparation of Acetic Acid Solvate by Direct Crystallization 149.4 g of Compound 1 (i.e., an amount of Compound 1 that should completely dissolve in about 800 mL of acetic acid at 55° C.) is charged to a 3-liter 5-necked jacketed reactor equipped with a nitrogen blanket, condenser, thermometer probe, and overhead stirrer. Charging 800 mL of acetic acid to the reactor then forms a slurry of Compound 1 in acetic acid. The contents of the reactor are heated to 55° C. until all of the Compound 1 is dissolved. The solution should be clear once all of Compound 1 is dissolved. 1200 mL of ethyl acetate is then added to the solution. The contents of the reactor are heated again to 55° C. After the solution has reached a temperature of 55° C., heating is stopped and the solution is then cooled according to the following cooling ramp protocol: (a) cool the solution to about 40° C. over a period of about 15 minutes; (b) hold the solution at a temperature of about 40° C. for about one hour (nucleation typically will occur during this step of the cooling ramp protocol); (c) cool the solution to about 30° C. over a period of about 15 minutes; (d) hold the solution at a temperature of about 30° C. for about 2.5 hours; and (e) cool the solution to about 0° C. over a period of about two hours. The temperature of the reactor is then maintained at about 0° C. and the solution is stirred until the concentration of Compound 1 in solution is less than 1.0 weight percent of the total weight of the solution. Extended stirring times generally will produce no adverse effects on the acetic acid solvate. The resulting slurry is then filtered to yield a solid product that is the acetic acid solvate.

Example 2
Preparation of Acetic Acid Solvate by Slurry Conversion 1.5 g of the Form II polymorph of Compound 1 is placed in a flask. 5.4 mL of acetic acid (i.e., an amount of acetic acid that just forms a slurry with the Form II polymorph) is added. The crystals are slurried at room temperature for 21 hours. The slurry is filtered and a solid product is isolated that is the acetic acid solvate.

Example 3
Alternative A: Preparation of NMP Solvate by Direct Crystallization (without Anti-Solvent)

40 g of Compound 1 is added to 226.7 g of N-methylpyrrolidone (i.e., an amount of Compound 1 sufficient to form a 15 weight percent slurry of Compound 1 in N-methylpyrrolidone). The slurry is then heated to about 58° C. Dissolution of Compound 1 typically is noted at about 40° C. The resulting solution is then cooled to about −10° C. over a period of about five hours with crystallization initiating between about 40° C. and about 28° C. The slurry is then filtered to remove a solid product that is the NMP solvate. This solid product is washed twice with N-methylpyrrolidone.

Alternative B: NMP Solvate from Reaction Mixture

A 100 mL reactor is charged with 10 g of 5-(4-piperidyl)-4-(4-pyrimidinyl)-3-(4-chlorophenyl) pyrazole (Compound 2; prepared as set forth in Example D-1 of WO00/31063), 20 g of N-methylpyrrolidinone ("NMP"), 9.8 g of butyl glycolate, and 0.45 g of 1,8-diazabicyclo[5.4.0]undec-7-ene ("DBU"). The resulting mixture is heated to 110° C. and held for 3 hours. The mixture is cooled to 0° C. Crystallization typically occurs between 50° C. and 0° C. The NMP solvated crystalline form of Compound 1 is isolated.

Alternative C: NMP Solvate from Reaction Mixture with Seeding

A 1000 mL reactor is charged with 10 g of 5-(4-piperidyl)-4-(4-pyrimidinyl)-3-(4-chlorophenyl) pyrazole (Compound 2; prepared as set forth in Example D-1 of WO00/31063), 20 g of N-methylpyrrolidinone ("NMP"), 9.8 g of butyl glycolate, and 0.45 g of 1,8-diazabicyclo[5.4.0]undec-7-ene ("DBU"). The resulting mixture is heated to 110° C. and held for 3 hours. The mixture is cooled to 75° C. and seeded with approximately 1 weight % NMP solvate crystals. Crystallization typically occurs after seeding at approximately 75° C. The mixture is then cooled to 0° C. at 0.5° C./min and filtered. The product is the NMP solvated crystalline form of Compound 1.

Example 4

Alternative A: Preparation of NMP Solvate by Direct Crystallization (with Anti-Solvent)

4 g of Compound 1 is dissolved in 12 g of N-methylpyrrolidone (i.e., an amount of Compound 1 sufficient to form a 25 weight percent solution of Compound 1 in N-methylpyrrolidone) at a temperature of 90° C. This solution is cooled to about 5° C. and 2 g of water is added. The resulting slurry is stirred at a temperature of about 5° C. for about three days. The slurry is then filtered to remove a solid product that is the NMP solvate.

Alternative B: Preparation of the NMP Solvate (with Antisolvent)

A 49 L reactor is charged with 1.9 kg of 5-(4-piperidyl)-4-(4-pyrimidinyl)-3-(4-chlorophenyl) pyrazole (Compound 2; prepared as set forth in Example D-1 of WO00/31063), 3.8 kg of N-methylpyrrolidinone ("NMP"), 1.85 kg of butyl glycolate, and 85.1 g of 1,8-diazabicyclo[5.4.0]undec-7-ene ("DBU"). The resulting mixture is heated to 110° C. and held for 3 hours. The mixture is cooled to 40° C. (alternatively, the mixture may be cooled to 25° C.) and anhydrous ethanol 3A (0.4×weight of Compound 2) is charged over 23 minutes. The NMP solvate crystalline form of Compound 1 is produced. The resulting slurry is held at 40° C. for over 15 minutes. The slurry is heated to reflux and held for 4 hours. The mixture is cooled to 5° C. using a 0.25° C./min cooling rate and held for about 6.5 hours. The slurry is filtered and the solids isolated are washed with methyl t-butyl ether. The solids are pulled dry for about 1.5 hours using vacuum. The crude product is the NMP solvated crystalline form of Compound 1.

Example 5

Preparation of Form I Polymorph through Intermediate Salt 5-(4-piperidyl)-4-(4-pyrimidinyl)-3-(4-chlorophenyl) pyrazole (Compound 2; prepared as set forth in Example D-1 of WO00/31063) and 2.5 molar equivalents of butyl glycolate are charged to a flask. The resulting mixture is heated to about 132° C. and maintained at that temperature for four hours to yield Compound 1. This reaction mixture comprising Compound 1 is cooled to about 0° C. 1.8 molar equivalents of sodium hydroxide (50%), methanol and butanol are added to the reaction mixture while maintaining the temperature of the reaction mixture below about 5° C. The resulting solution is stirred for about 15 minutes at a temperature of about 0° C. Hydrochloric acid (about 37%) is then added over a period of about 15 minutes. The resulting slurry is held at a temperature of about 0° C. for about three hours. The slurry is heated to about 65° C. and held at that temperature for about five hours. It is then cooled to about 0° C. over a period of about 4 hours and maintained at that temperature for about three hours. The slurry is filtered and a filtration cake is isolated. The filtration cake is washed first with methanol, then with ethyl acetate, and finally with water. The washed filtration cake is placed in a jacketed vessel, water is added to the vessel, and the resulting slurry is stirred for about 30 minutes. The slurry is filtered to remove a solid product. The product is washed first with water and then with ethyl acetate. The product is then dried in an oven at 70° C. under house vacuum to yield the Form I polymorph.

Example 6

Alternative A: Preparation of Form I Polymorph by Refluxing in NMP

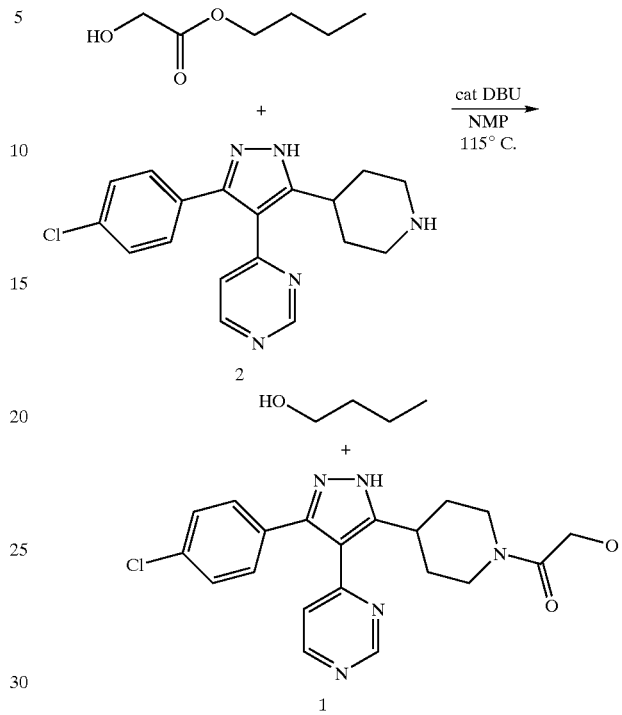

A 25 mL round bottom flask is charged with 2 g of 5-(4-piperidyl)-4-(4-pyrimidinyl)-3-(4-chlorophenyl) pyrazole (Compound 2; prepared as set forth in Example D-1 of WO00/31063), 2.5 g of N-methylpyrrolidone, 1.95 g of butyl glycolate, and 0.1 g of 1,8-diazabicyclo[5.4.0] undec-7-ene ("DBU"). The resulting mixture is heated to 115° C. and held at that temperature for 3.5 hours. The mixture is cooled down to 50° C. and 17.5 g methanol is added. The resulting slurry is held at 50° C. for 30 minutes. The slurry is then heated to 65° C. for two hours thereby converting the solids presents to the Form I polymorph. The slurry is cooled to room temperature over a period of four hours and held at that temperature over night. The slurry is then cooled to 5° C. for about six hours. The slurry is filtered and the solids isolated are washed with methanol. The solids are dried overnight at house vacuum and then placed in a vacuum oven at about 50° C. at house vacuum. The product is the Form I polymorph.

Alternative B: Preparation of Form I by refluxing in NMP and Ethanol

A 49 L reactor is charged with 1.9 kg of 5-(4-piperidyl)-4-(4-pyrimidinyl)-3-(4-chlorophenyl) pyrazole (Compound 2; prepared as set forth in Example D-1 of WO00/31063), 3.8 kg of N-methylpyrrolidinone ("NMP"), 1.85 kg of butyl glycolate, and 85.1 g of 1,8-diazabicyclo[5.4.0]undec-7-ene ("DBU"). The resulting mixture is heated to 110° C. and held for 3 hours. The mixture is cooled to 25° C. and anhydrous ethanol 3A (6.5×weight of Compound 2) is charged over 55 minutes. An NMP solvated crystalline form of Compound 1 is initially formed. The resulting slurry is held at 25° C. for over 1 hour. The slurry is heated to reflux and held for 4 hours. The NMP solvated crystalline form is substantially converted to the Form I crystalline form of Compound 1 within about 30 minutes at reflux. The mixture is cooled to 5° C. using a 0.25° C./min cooling rate and held for about 6.75 hours. The slurry is filtered and the solids isolated are washed with anhydrous ethanol 3A. The solids are pulled dry for about 1.5 hours using vacuum. The crude product is the Form I crystalline form of Compound 1.

Alternative C:

The NMP solvated crystalline form of Compound 1 prepared as set forth in the above Alternative B is isolated and charged to a 49L reactor. Anhydrous ethanol 3A (9×weight of NMP solvate placed in reactor) is added. The resulting slurry is heated to reflux and held for 4 hours. The refluxing lowers the level of NMP incorporated with the crystal. The mixture is cooled to 5° C. over 3 hours and held overnight. The slurry is filtered and the solids isolated are washed with anhydrous ethanol 3A. The solids are pulled dry using vacuum. The product is the Form I crystalline form of Compound 1.

Example 7
Preparation of Form I Polymorph by Refluxing in Xylenes

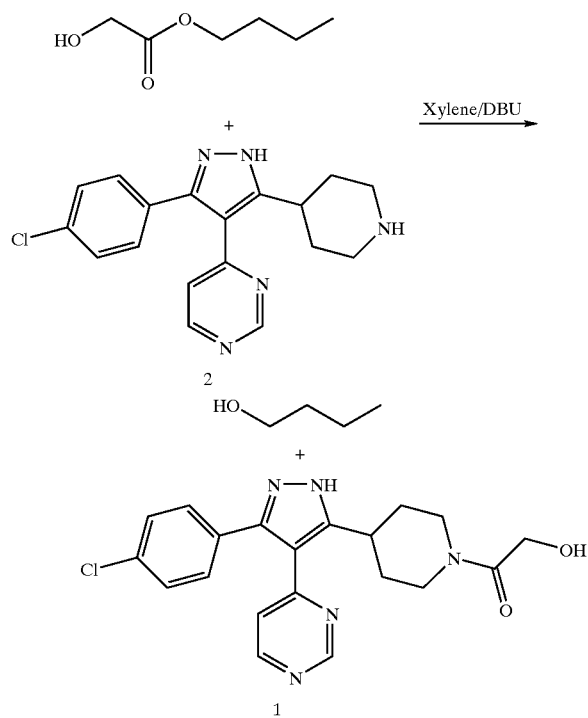

A flask is charged with 5.0 g of 5-(4-piperidyl)-4-(4-pyrimidinyl)-3-(4-chlorophenyl)pyrazole (Compound 2; prepared as set forth in Example D-1 of WO00/31063), 5.0 g of butyl glycolate (Fluka, 95%), 0.2 g of 1,8-diazabicyclo[5.4.0]undec-7-ene (Aldrich, 99%), and 15 mL of xylenes (EM, 98.5%). The resulting mixture (initial temperature of about 138° C.) is heated to reflux. After about five minutes of reflux, a yellow solution is formed. After an additional five minutes of reflux, a light yellow solid starts to precipitate from the solution. Reflux is continued and the internal temperature is slowly decreased to about 136° C. After about two hours of reflux, heating is stopped and the mixture is cooled to about 120° C. 10 mL of 1-butanol is added and the mixture is heated at reflux for five minutes (internal temperature about 122° C.). The mixture is then cooled to 25° C. A light yellow solid is filtered, washed with toluene (2×15 mL) and with hexane (40 mL) to yield a light yellow solid product that is the Form I polymorph of Compound 1.

Example 8
Alternative A: Preparation of Form I Polymorph from NMP Solvate 4 g of Compound 1 is dissolved in 12 g of N-methylpyrrolidone (i.e., an amount of Compound 1 sufficient to form a 25 weight percent solution of Compound 1 in N-methylpyrrolidone) at a temperature of 90° C. The resulting solution is cooled to about 5° C. and 2 g of water is added. 12 g of methanol is added and the solution is heated to about 64° C. The crystals that were previously present are observed to dissolve in the solution at this temperature and to recrystallize rapidly to yield the Form I polymorph.

Alternative B: Preparation of Form I from the NMP solvate 1.22 kg of the NMP solvated crystalline form of Compound 1 is added to 9.0 kg of anhydrous ethanol 3A. The resulting slurry is held for 1 hour. At the end of this period, the NMP solvated form of Compound 1 is substantially converted to the Form II crystalline form of Compound 1. The slurry is heated to reflux and held for 5 hours. The Form II crystalline form of Compound 1 is substantially converted to the Form I crystalline form of Compound 1 within about 1 hour. The mixture is cooled to 5° C. over 2.5 hours and held overnight. The slurry is filtered and the solids isolated are washed with anhydrous ethanol 3A. The solids are pulled dry using vacuum and then placed in a vacuum oven at 50° C. The product is the Form I crystalline form of Compound 1.

Alternative C: Preparation of Form I from the NMP solvate (with DBU)

4 g of the NMP solvated crystalline form of Compound 1 is added to 36 g of anhydrous ethanol 3A, premixed with 0.07 equivalents of DBU. The resulting slurry is held for 1 hour. At the end of this period, the NMP solvated crystalline form of Compound 1 is substantially converted to the Form II crystalline form of Compound 1. The slurry is heated to reflux and held for 4 hours. At the end of this period, the Form II crystalline form of Compound 1 is substantially converted to the Form I crystalline form of Compound 1. The slurry is cooled to 0° C. over 3 hours and held overnight. The slurry is filtered and the solids isolated are washed with anhydrous ethanol 3A. The solids are pulled dry using vacuum and then placed in a vacuum oven at 50° C. The product is the Form I crystalline form of Compound 1.

Example 9
Preparation of Form II Polymorph from Acetic Acid Solvate

A slurry is prepared by adding ethyl acetate to a flask containing the acetic acid solvate of Compound 1. 10 mL of ethyl acetate is added for each gram of the acetic acid solvate present. The resulting slurry is heated to about 45° C. and stirred until the acetic acid content in the solids has dropped to less than about 0.1 weight percent as determined by gas chromatography. The slurry is filtered to isolate a product that is the Form II polymorph.

Example 10
Preparation of Form II Polymorph from NMP Solvate 34.8 g of the NMP solvate of Compound 1 is slurried in 243.5 g of ethyl acetate (i.e., an amount of Compound 1 sufficient to form a 12.5 weight percent slurry of Compound 1 in N-methylpyrrolidone). The slurry is heated to about 60° C. and held at that temperature for about 6 hours. During this holding period, the viscosity of the solution typically decreases thereby indicating a change in polymorph form. The slurry is then cooled to about 20° C. over a period of about one hour. The slurry is filtered to remove a white solid product that is the Form II polymorph.

Example 11
Preparation of Form III Polymorph from Dihydrate Crystalline Form 4 g of Compound 1 is placed in a 100 ml vessel with 23 mls acetic acid. The mixture is heated to 100 deg C. and stirred for 1 hour. The mixture is then cooled to 45 deg C. and 34.5 mls of water is added in a programmed addition over 2 hrs. The mixture is then cooled to 5 deg C. and stirred over night. The resulting slurry is then filtered to yield a product that is the dihydrate crystalline form. The product is then placed in a vacuum oven at about 50 deg C., allowing the dihydrate to be converted to the Form III polymorph of Compound 1.

Example 12
Preparation of Monohydrate Crystalline Form from Form I Polymorph 4 g of the Form I polymorph of Compound 1 is dissolved in 18.4 mL of acetic acid. The mixture is heated to about 90° C. The resulting solution is cooled to about 45° C. and 27.4 mL of water is added. The solution is then cooled to about 5° C. over about six hours. Crystallization typically is seen to occur at about 28° C. The crystals are isolated by filtration to yield a solid product that is the monohydrate crystalline form of Compound 1.

Example 13
Preparation of Dihydrate Crystalline Form from Form I Polymorph 4 g of the Form I polymorph of Compound 1 is dissolved in 23 mL of acetic acid at 90° C. 34.5 mL of water is added cubically to the solution over a period of about two hours. At the end of the two-hour addition period, the solution is cooled to about 5° C. over a period of about three hours and then maintained at that temperature. Crystals typically have grown in the solution after about three hours 40 minutes at 5° C. These crystals are isolated by filtration after about five hours at 5° C. to yield a product that is the dihydrate crystalline form of Compound 1.

Example 14
Preparation of Dihydrate Crystalline Form from Form II Polymorph

The Form II polymorph of Compound 1 is added slowly to a vial containing an 80/20 tetrahydrofuran/water solution (v/v) and allowed to dissolve. The addition of the Form II polymorph to solute is stopped when excess solids become apparent. The vial is allowed to equilibrate at about 25° C. After about 5 days, the solution in the vial is filtered and a solid product is isolated that is the dihydrate crystalline form of Compound 1.

Example 15
Preparation of Crystalline Sodium Salt Form of Compound 1

The crystalline sodium salt form of Compound 1 can be prepared, for example, using sodium methoxide. In one illustrative example, a 25-mL, one-necked round-bottomed flask equipped with a tubing adapter connected to a nitrogen bubbler, and a magnetic stirring bar is charged with Compound 1 (0.4 g, 1.0 mmol) and 2 mL of methanol. Sodium methoxide is added as a 1.0 M solution in methanol (1.0 mL, 1.0 mmol). The resulting suspension is stirred overnight at room temperature, forming a suspension of a crystalline solid. The crystals are collected by filtration, washed with a few drops of methanol, and dried overnight at 40° C. under oil-pump vacuum to give 0.252 g of Compound 1 as a near-colorless crystalline solid.

The compound has the following characteristics: $^1$H NMR (DMSO-$d_6$; 400 MHz) δ: 1.6–1.9 (m, 4H), 2.7 (t, 1H), 3.0 (t, 1H), 3.3 (m, 1H), 3.7 (d, 1H), 4.1 (q, 2H), 4.4 (d, 1H), 6.9 (d, 1H), 7.3–7.4 (m, 4H), 8.3 (d, 1H), 8.9 (s, 1H). Microanalysis: Calculated for $C_{20}H_{19}ClN_5NaO_2$: C, 57.22; H, 4.56; N, 16.68. Found: C, 57.26; H, 4.75; N, 16.50.

Example 16
Preparation of an HCl salt of N-(2-hydroxyacetyl)-5-(4-piperidyl)-4-(4-pyrimidinyl)-3-(4-chlorophenyl)pyrazole.

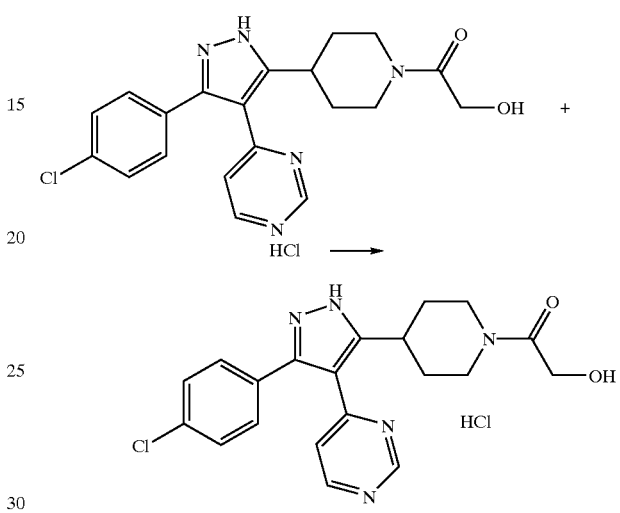

A 10-mL, one-necked, round-bottomed flask equipped with a tubing adapter connected to a nitrogen bubbler and a magnetic stirring bar was charged with N-(2-hydroxyacetyl)-5-(4-piperidyl)-4-(4-pyrimidinyl)-3-(4-chlorophenyl)pyrazole (0.398 g, 1.0 mmol) and 3.0 mL of ethanol. Hydrogen chloride was then added as a 1.0 M solution in ethanol (1.25 mL, 1.25 mmol). The resulting suspension was stirred at room temperature for 1 hour, and then heated to reflux. The hot solution was filtered to remove a small amount of insoluble material. The filtrate was then stirred at room temperature for 2 hours. The suspension that formed was then cooled in an ice-water bath and stirred for an additional 2 hours. The suspension of crystals was filtered, and the collected solid was dried for 2 hours at 40° C. under oil-pump vacuum to afford 0.381 g of the HCl salt as a yellow crystalline solid. The salt had the following characteristics: $^1$H NMR (DMSO-$d_6$; 400 MHz) δ: 1.7 (m, 2H), 1.9 (d, 2H), 2.7 (t, 1H), 3.0 (t, 1H), 3.4 (m, 1H), 3.8 (d, 1H), 4.1 (q, 2H), 4.5 (d, 1H), 7.2 (d, 1H), 7.4–7.5 (m, 4H), 8.7 (d, 1H), 9.3 (s, 1H). Microanalysis: Calculated for $(C_{20}H_{20}ClN_5O_2)\cdot HCl\cdot 0.2(EtOH)$: C, 55.24; H, 5.04; N, 15.79. Found: C, 54.97; H, 5.04; N, 15.72.

Example 17
Preparation of Crystalline Mesylate Salt Form

The crystalline mesylate (methanesulfonic acid) salt form of Compound 1 can be prepared, for example, using a solution of methanesulfonic acid in propanol. In one illustrative example, a 500-mL, three-necked round-bottomed flask equipped with a 50 mL pressure-equalizing addition funnel, a tubing adapter connected to a nitrogen bubbler and a magnetic stirring bar is charged with Compound 1 (10.3 g, 26.0 mmol) and 170 mL of 2-propanol. Methanesulfonic acid is added as a 1.0 M solution in 2-propanol (28.6 mL, 28.6 mmol) through the dropping funnel over a period of 3 minutes. The mixture is stirred at room temperature for 24 hr. A suspension of a crystalline solid is formed. The crystals are collected by filtration, washed twice with 10 mL portions of cold 2-propanol and air dried overnight to give 12.5 g of Compound 1 as a pale yellow crystalline solid.

The compound has the following characteristics: $^1$H NMR (DMSO-$d_6$; 400 MHz) δ: 1.7 (m, 2H), 1.9 (d, 2H), 2.4 (s, 3H, CH$_3$SO$_3$), 2.7 (t, 1H), 3.0 (t, 1H), 3.4 (m, 1H), 3.8 (d, 1H), 4.1 (q, 2H), 4.4 (d, 1H), 7.2 (d, 1H), 7.4–7.5 (q, 4H), 8.7 (d, 1H), 9.3 (s, 1H). Microanalysis: Calculated for (C$_{20}$H$_{20}$ClN$_5$O$_2$).1.05(CH$_4$O$_3$S).0.11(C$_3$H$_8$O): C, 50.80; H, 4.99; N, 13.87. Found: C, 50.70; H, 5.22; N, 13.85.

Example 18

Preparation of Crystalline Tosylate Salt Form

The crystalline tosylate (p-toluenesulfonic acid) salt form of Compound 1 can be prepared, for example, using a solution of p-toluenesulfonic acid in ethanol. In one illustrative example, a 50-mL Erlenmeyer flask equipped with a magnetic stirrer bar is charged with Compound 1 (1.4 g, 3.50 mmol) and 14 mL of ethanol. p-Toluenesufonic acid is added as a 1.0 M solution in ethanol (4.36 mL, 4.36 mmol) and the suspension is heated at 75° C. for about 45 minutes. The resulting clear yellow solution is then evaporated with a stream of nitrogen to a volume of 12 mL, 15 mL of acetonitrile is added, and the mixture is stirred overnight at room temperature. A suspension of crystals is formed. The crystals are collected by filtration, washed twice with 1 mL portions of acetonitrile, and dried overnight under oil-pump vacuum at 40° C. to give 1.8 g of Compound 1 as a near colorless crystalline solid.

The compound has the following characteristics: $^1$H NMR (DMSO-$d_6$; 400 MHz) δ: 1.7 (m, 2H), 1.9 (d, 2H), 2.3 (s, 3H, CH$_3$C$_6$H$_4$SO$_3$), 2.7 (t, 1H), 3.0 (t, 1H), 3.4 (m, 1H), 3.6 (d, 1H), 4.1 (q, 2H), 4.5 (d, 1H), 7.1 (d, 2H), 7.3 (d, 1H), 7.4 (m, 2H), 7.4–7.5 (m, 4H), 8.7 (d, 1H), 9.3 (s, 1H). Microanalysis: Calculated for (C$_{20}$H$_{20}$ClN$_5$O$_2$).1.0 (C$_7$H$_8$O$_3$S): C, 56.89; H, 4.95; N, 12.29. Found: C, 56.70; H, 4.90; N, 12.26.

Example 19

Preparation of N-(2-hydroxyacetyl)-5-(4-piperidyl)-4-(4-pyrimidinyl)-3-(4-chlorophenyl)pyrazole Part A. Preparation of ethyl N-(t-butoxycarbonyl) isonipecotate (3):

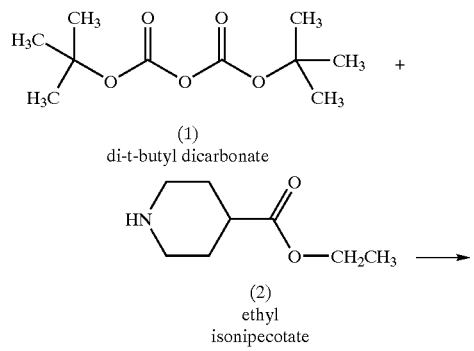

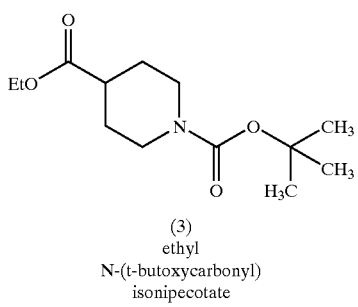

(3)
ethyl
N-(t-butoxycarbonyl)
isonipecotate

This reaction was conducted in a jacketed, 49 L reactor equipped with a retreat curve agitator, nitrogen purge system, and condenser system. The reactor was charged with di-t-butyl dicarbonate (1) in tetrahydrofuran ("THF") (75%, 4.674 Kg, 16.06 mol) and tetrahydrofuran (5.50 Kg, 76.3 moles). After cooling the mixture to 0° C, ethyl isonipecotate (2) (2.500 Kg, 15.90 mol) was charged to the reactor while maintaining the contents at a temperature of from 0 to 15° C. After all the ethyl isonipecotate was added, the contents were warmed to 25° C., and then stirred for 2 hours at that temperature. The mixture was then cooled to 0° C. The THF was then removed by vacuum distillation until the batch temperature reached 80° C. Afterward, the contents were cooled to 25° C. This yielded 3.99 Kg of product in the form of an amber oil. The concentration of the Boc-protected ethyl isonipecotate (3) was 96.3% (by weight).

TABLE 16

Reaction Summary for Part A

| materials | MW | equiv. | wt (kg) | moles | density (g/mL) | volume (L) |
|---|---|---|---|---|---|---|
| compound (1) (75%) | 218.25 | 1.01 | 4.674 | 16.06 | 0.913 | 5.12 |
| tetrahydrofuran | 72.11 | 4.8 | 5.50 | 76.3 | 0.889 | 6.19 |
| compound (2) | 157.21 | 1.00 | 2.500 | 15.90 | 1.020 | 2.45 |
| product |  |  |  |  |  |  |
| compound (3) | 257.33 | (1.00) | (4.092) | (15.90) |  |  |

The numbers in parenthesis in the above table are theoretical..

Part B. Preparation of the N-(t-butoxycarbonyl)-1-(4-piperidyl)-2-(4-pyrimidyl)-1-ethanone (5).

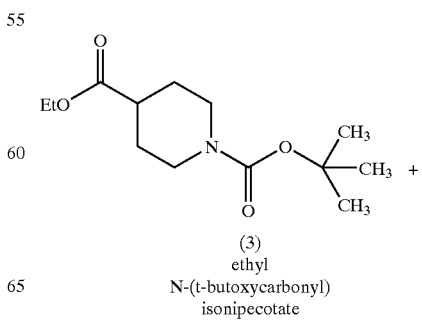

(3)
ethyl
N-(t-butoxycarbonyl)
isonipecotate

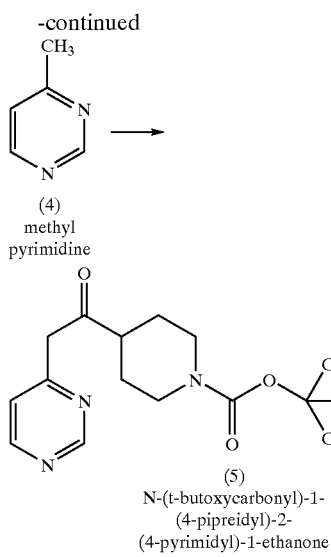

(4) methyl pyrimidine (5) N-(t-butoxycarbonyl)-1-(4-pipreidyl)-2-(4-pyrimidyl)-1-ethanone This reaction was conducted in the same jacketed, 49 L reactor equipped with retreat curve agitator, nitrogen purge system, bottom valve for removal of a lower portion of the contents, and Dean-Stark trap and condenser system. The reactor was first purged with nitrogen. Afterward, 20% potassium t-butoxide in THF (21.06 Kg, 37.54 mol) was charged to the reactor under $N_2$ using a cannula system. This solution was then cooled to 0° C., and the reactor was next charged with 4-methylpyrimidine (4) (1.53 Kg, 16.27 mol) while maintaining the temperature of the reactor contents at from 0 to 5° C. Immediately afterward, the Boc-protected ethyl isonipecotate (3) prepared as shown in Part A (3.99 Kg, 15.51 mol) was charged neat over 30 minutes while continuing to maintain the reactor contents at a temperature of from 0 to 5° C. Afterward, the reactor contents were stirred for 3 hours while being maintained at 5° C. The temperature of the reactor contents was then increased to 10° C., and then maintained at that temperature for 1 hour. Subsequently, 33% aqueous acetic acid solution (6.71 Kg, 36.88 mol) was charged to the reaction mixture while maintaining the reaction mixture at below 30° C. After stirring the resulting mixture for 30 minutes, it was allowed to stand for 30 minutes. The aqueous layer was then separated. Afterward, ammonium chloride solution (2.96 Kg, 3.87 mol) was charged to the reactor. The resulting mixture was stirred for 30 minutes. After allowing the mixture to stand for 30 minutes, the aqueous layer was separated. The THF was removed from the organic remaining layer by slowly raising the batch temperature under vacuum (200 torr) until the temperature reached 60–65° C. using a distillation apparatus. The final concentrate was in the form of an amber oil. This oil and toluene (12.22 Kg, 132.6 mol) were combined in the reactor, and the resulting mixture was stirred at room temperature for 15 minutes. Afterward, water (4.01 kg, 222.5 mol) was added to the reactor, and stirring was continued for an additional 30 minutes at room temperature. The reactor contents were allowed to stand for 60 minutes. The aqueous layer was then separated. The top layer (i.e., the organic layer) was then used as is to prepare the hydrazone in Part C.

TABLE 17

Reaction Summary for Part B

| materials | MW | equiv. | wt (kg) | moles | density (g/mL) | volume (L) |
|---|---|---|---|---|---|---|
| potassium t-butoxide in THF (20%) | 112.2 | 2.42 | 21.06 | 37.54 | 0.902 | 23.3 |
| compound (3) | 257.3 | 1.00 | 3.99 | 15.51 | 1.034 | 3.86 |
| compound (4) | 94.11 | 1.05 | 1.53 | 16.27 | 1.031 | 1.48 |
| 33% acetic acid solution | 60.05 | 2.40 | 6.71 | 36.88 | 1.049 | 6.4 |
| 7% ammonium chloride solution | 53.49 | 0.25 | 2.96 | 3.87 | | |
| toluene | 92.14 | 10.20 | 12.22 | 132.6 | 0.865 | 14.1 |
| water | 18.02 | 14.35 | 4.01 | 222.5 | 1.000 | 4.01 |

Part C. Preparation of the N-(t-butoxycarbonyl)-1-(4-piperidyl)-2-(4-pyrimidyl)-1-ethanone p-toluenesulfonyl hydrazone (7).

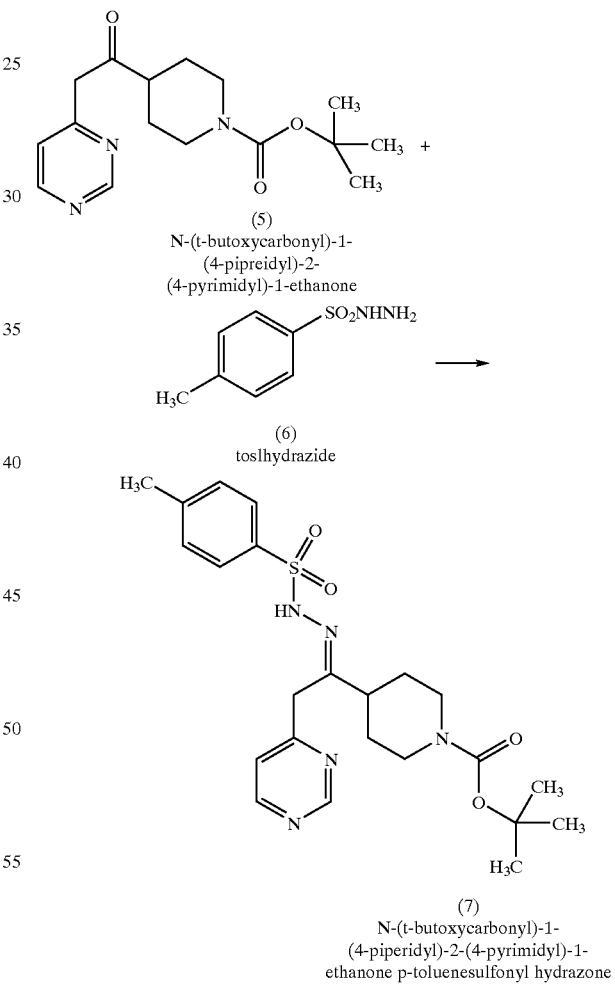

(5) N-(t-butoxycarbonyl)-1-(4-pipreidyl)-2-(4-pyrimidyl)-1-ethanone (6) toslhydrazide (7) N-(t-butoxycarbonyl)-1-(4-piperidyl)-2-(4-pyrimidyl)-1-ethanone p-toluenesulfonyl hydrazone Toluenesulfonylhydrazide (6) (2.6 Kg, 13.96 mol) was combined with the reaction mixture from Part B in the same reactor. The resulting mixture was heated to 70° C. while being stirred and maintained at this temperature for 2 hours. The reaction mixture was then refluxed at 70° C. under reduced pressure (200 torr) using the Dean-Stark moisture trap for 1 hour. Afterward, the mixture was cooled to 0° C.

over 1.5 hours, and then maintained at 0° C. for at least 12 hours. The resulting solids were collected using a filter (using a 4 micron filter cloth). The wet cake was then washed with toluene (3.79 Kg, 41.13 mol, 0 to 5° C.), followed by ethyl acetate (3.95 Kg, 44.83 mol, 0 to 5° C.). After the cake was dried on the filter for 2 hours, and then transferred to a vacuum oven at 40° C. for at least 4 hour. This yielded 5.15 Kg (70%) of a light yellow solid. The concentration of hydrazone (7) was 99.2% (by weight).

TABLE 18

Reaction Summary for Part C

|  | MW | equiv. | wt (kg) | moles | density (g/mL) | volume (L) |
|---|---|---|---|---|---|---|
| materials |  |  |  |  |  |  |
| compound (6) | 186.2 | 0.90 | 2.60 | 13.96 |  |  |
| toluene | 92.14 | 2.65 | 3.79 | 41.13 | 0.865 | 4.38 |
| ethyl acetate | 88.10 | 2.89 | 3.95 | 44.83 | 0.902 | 4.38 |
| product |  |  |  |  |  |  |
| compound (7) | 473.60 | (1.00) | (7.34) | (15.51) |  |  |

The numbers in parenthesis in the above table are theoretical.

Part D. Preparation of tert-butyl 4-{5-(4-chlorophenyl)-1-[(4-methylphenyl)sulfonyl]-4-pyrimidin-4-yl-1H-pyrazol-3-yl}piperidine-1-carboxylate (9).

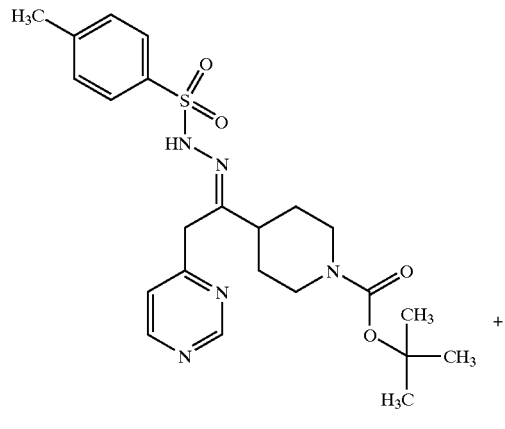

(7)
N-(t-butoxycarbonyl)-1-(4-piperidyl)-2-(4-pyrimidyl)-1-ethanone p-toluenesulfonyl hydrazone

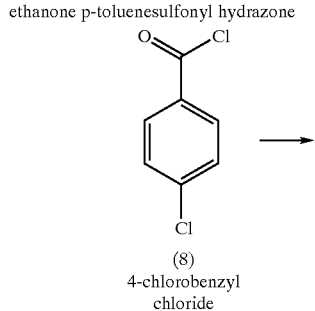

(8)
4-chlorobenzyl chloride

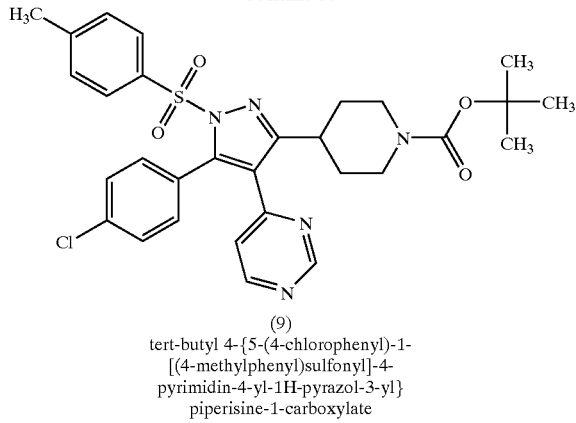

(9)
tert-butyl 4-{5-(4-chlorophenyl)-1-[(4-methylphenyl)sulfonyl]-4-pyrimidin-4-yl-1H-pyrazol-3-yl}piperisine-1-carboxylate This reaction was conducted in the same jacketed, 49 L reactor equipped with a retreat curve agitator, metering pump, nitrogen purge system, and condenser system. The reactor was first purged with nitrogen at room temperature. The clean, dry reactor was then charged with the hydrazone (7) prepared as shown in Part C (2.77 Kg, 5.85 mol), dimethylaminopyridine ("DMAP") (0.0715 Kg, 0.585 mol), tetrahydrofuran (12.47 Kg, 173.04 mol), and triethylamine (0.829 Kg, 8.19 mol). Next, 4-chlorobenzoyl chloride (8) ("CBC") (1.28 Kg, 7.31 moles) was added to the reactor over 20 minutes using a pump at such a rate as to keep the internal temperature less than 40° C. The contents turned deep yellow and formed a precipitate. After the addition of the 4-chlorobenzoyl chloride, the reaction mixture was heated to 65° C. over 30 minutes, and then maintained at that temperature for 5 hours. Subsequently, the temperature of the mixture was decreased to room temperature, and water (2.77 kg, 153.7 mol) was added. The resulting mixture was stirred for 0.5 hours. Subsequently, the organic and aqueous phases were allowed to separate, and the aqueous phase was removed from the bottom of the reactor. To the remaining organic layer was added 22% aqueous ammonium chloride solution (4.62 L). The resulting mixture was stirred for 0.5 hours. The stirring was stopped and the organic and aqueous phases were allowed to separate. The aqueous phase was removed from the bottom of the reactor. An IPA-water mixture (1:1 (vol:vol); 22.16 L) was then added to the remaining organics over 2 hours. Subsequently, the resulting mixture was stirred for 5 hours. The solids were filtered (4 micron filter cloth), washed with IPA-water (1:1 (vol:vol); 7.39 L), and dried on the filter for 2 hours. The wet cake was transferred to a vacuum oven at 80° C. (house vacuum) for 6 hours. This yielded 2.85 Kg (84.6%) of solids. The concentration of the protected pyrazole intermediate (9) was 99.0% (by weight).

TABLE 19

Reaction Summary for Part D

|  | MW | equiv. | wt (Kg) | moles | density (g/mL) | Volume (L) |
|---|---|---|---|---|---|---|
| material |  |  |  |  |  |  |
| compound (7) | 473.59 | 1.0 | 2.77 | 5.85 |  |  |
| tetrahydrofuran (THF) | 72.11 | 29.58 | 12.47 | 173.04 | 0.889 | 14.0 |
| compound (8) | 175.01 | 1.25 | 1.28 | 7.31 | 1.377 | 0.93 |
| triethylamine (TEA) | 101.19 | 1.43 | 0.829 | 8.19 | 0.726 | 1.14 |

TABLE 19-continued

Reaction Summary for Part D

|  | MW | equiv. | wt (Kg) | moles | density (g/mL) | Volume (L) |
|---|---|---|---|---|---|---|
| 4-dimethylamino pyridine (DMAP) | 122.17 | 0.102 | 0.0715 | 0.585 | | |
| water | 18 | 26.3 | 2.77 | 153.7 | 1.000 | 2.77 |
| 22% NH₄Cl | 53.49 | 3.5 | | 18.47 | | 4.62 |
| IPA-water anti-solvent | | | | | | 22.16 |
| IPA-water cake wash product | | | | | | 7.39 |
| compound (9) | 594.13 | (1.0) | (3.48) | (5.85) | | |

The numbers in parenthesis in the above table are theoretical.

Part E. Preparation of 5-(4-piperidyl)-4-(4-pyrimidinyl)-3-(4-chlorophenyl)pyrazole (10).

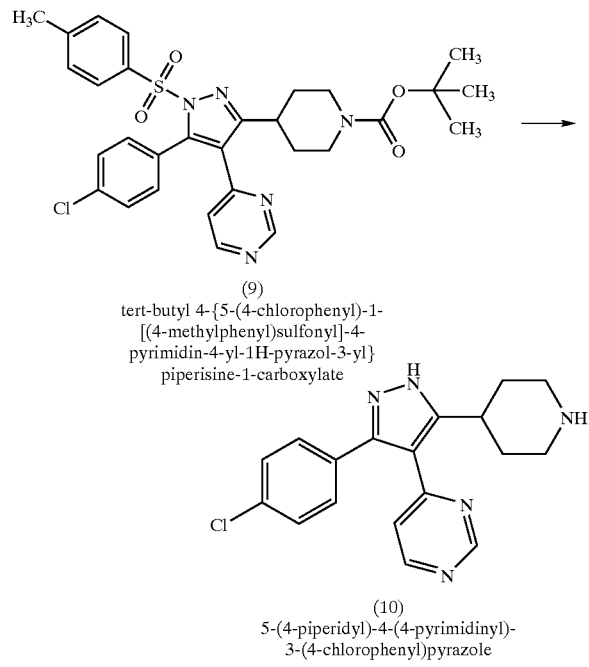

(9)
tert-butyl 4-{5-(4-chlorophenyl)-1-[(4-methylphenyl)sulfonyl]-4-pyrimidin-4-yl-1H-pyrazol-3-yl}piperisine-1-carboxylate

(10)
5-(4-piperidyl)-4-(4-pyrimidinyl)-3-(4-chlorophenyl)pyrazole

The following discussion describes two variations of this reaction:

A. First Variation

In the first variation, the above reaction was conducted in the same jacketed, 49 L reactor equipped with a retreat curve agitator, nitrogen purge, and metering pump. The reactor was charged with the protected pyrazole intermediate (9) prepared as shown in Part D (5.0 Kg, 8.42 mol) and toluene (10.0 kg, 108.5 mol). After initiating stirring, 37% HCl (6.64 Kg, 67.4 mmol) was added over 15 minutes via a pump. Immediate gas evolution and a temperature increase from 22.2° C. to 28.4° C. were observed. Two phases appeared within 10 minutes. The temperature was maintained at 20° C. for 1.0 hour. Afterward, water (20 Kg, 1110 mol) was added, and the resulting mixture was stirred for 20 minutes. The organic and aqueous phases were then separated, and the aqueous phase was introduced back into the reactor. The reactor was then additionally charged with 6 N NaOH (10.0 Kg, 60.2 mol) via a pump over 30 minutes. This increased the pH to 12, and caused a white/off-white slurry to form. The mixture was heated to 75° C. over 30 minutes, and then held at that temperature for an additional 2 hours. Subsequently, the mixture was cooled to 25° C. The solids were filtered with a 4 micron filter cloth, washed with deionized water (3×15 Kg), and air-dried for 45 minutes, i.e., until a constant weight (LOD<50%) was observed. The resulting cake was introduced into the reactor, along with acetonitrile (15 Kg). This mixture was heated to reflux, and then maintained at reflux for 1 hour. Subsequently, the mixture was cooled to 5° C., and then maintained at that temperature for 30 minutes. The solids were filtered with a 4 micron filter cloth, washed with acetonitrile (15 Kg), and dried in a vacuum oven at 85° C. for 12 hours (LOD<1%). This yielded 2.64 Kg (92%) of slightly off-white solids. The concentration of 5-(4-piperidyl)-4-(4-pyrimidinyl)-3-(4-chlorophenyl)pyrazole was greater than 97% (by weight). No single impurity was present at >1% (by weight). The residue on ignition ("ROI") was <1%, and the coulometric water determination according to the Karl Fisher method ("KF") also was <1%.

TABLE 20

Reaction Summary for Part E (First Variation)

| material | MW | equiv. vs. compound (9) | wt (Kg) | wt ratio to compound (9) | moles | density (g/mL) | volume (L) |
|---|---|---|---|---|---|---|---|
| compound (9) | 594.13 | 1.0 | 5.0 | 1 | 8.42 | — | — |
| 37% HCl | 36.46 | 8.0 | 6.64@ 37% | 1.3 | 67.4 | 1.200 | 5.53 |
| toluene | 92.14 | 12.9 | 10.0 | 2 | 108.5 | 0.865 | 11.6 |
| 6 N NaOH | 40.0 | 7.2 | 10.0 @ 6N | 2 | 60.2 | 1.22 | 8.2 |
| water addition | 18.02 | 132 | 20.0 | 4 | 1,110 | 1.000 | 20.0 |

TABLE 20-continued

Reaction Summary for Part E (First Variation)

|  | MW | equiv. vs. compound (9) | wt (Kg) | wt ratio to compound (9) | moles | density (g/mL) | volume (L) |
|---|---|---|---|---|---|---|---|
| water wash #1 | 18.02 | 99 | 15.0 | 3 | 832 | 1.000 | 15.0 |
| water wash #2 | 18.02 | 99 | 15.0 | 3 | 832 | 1.000 | 15.0 |
| water wash #3 | 18.02 | 99 | 15.0 | 3 | 832 | 1.000 | 15.0 |
| acetonitrile trituration | 41.05 | 43 | 15.0 | 3 | 365 | 0.786 | 19.0 |
| acetonitrile wash products | 41.05 | 43 | 15.0 | 3 | 365 | 0.786 | 19.0 |
| compound (10) | 339.83 | (1.0) | (2.86) |  | (8.42) |  |  |

The numbers in parenthesis in the above table are theoretical.

B. Second Variation

In the second variation, the above reaction was likewise conducted in the same jacketed, 49 L reactor equipped with a retreat curve agitator, nitrogen purge, and metering pump. The reactor was charged with the protected pyrazole intermediate (9) prepared as shown in Part D (5.0 Kg, 8.42 mol) and toluene (10.0 kg, 108.5 mol). After initiating stirring, 37% HCl (6.64 Kg, 67.4 mol) over 16 minutes. A temperature increase from 20 to 28° C. was observed during the addition. The temperature of the mixture was then increased to 70° C. over a 30 minutes period (1.5° C./minute), and held at 70° C. for 2 hours. The mixture was then cooled to 23° C. over 1 hour. After adding water (20 L), the mixture was stirred for 30 minutes. Agitation was then halted, and the phases were allowed to separate for 57 min. The bottom phase (i.e., the aqueous phase, which contained product) was removed from the reactor. After removing the top phase (i.e., the organic phase), the reactor was rinsed with toluene, followed by water, to remove residuals. The aqueous phase containing the product was then transferred back to the reactor. The reactor was then additionally charged with 6 N NaOH (10.0 kg, 54.74 mol, 6.5 equiv.) over 27 minutes. The observed final pH was 12.25. The reaction mixture was then heated to 75° C. over 30 minutes and held at that temperature for 2 hours. The slurry was then quickly cooled to 25° C. The product (in the form of solids) was collected by filtration using a pressure filter, and washed on the filter with water (2×15 L). The final pH of the rinse was 7.5. The cake was pulled dry for 60 minutes. This provided wet cake with a 19.4% LOD. The wet cake was charged back to the reactor, along with acetonitrile (15.0 kg, 19.1 L). The resulting mixture was heated to reflux (82° C.), and held at that temperature for 2 hours and 29 minutes. The slurry was then cooled to 5° C., and then held at that temperature for 30 minutes. The resulting product was filtered and then filter pulled dry until no mother languor was coming off the filter. The cake was rinsed with acetonitrile (18 L) and then pulled dry for 2 hours. The wet cake (LOD 12. 2%) was transferred to a vacuum dryer at 85° C. for 16 hours and 20 minutes (although it is believed that a time period of from 6 to 12 hours would have been sufficient). This provided 2.64 Kg at 92.2% isolated yield.

Part F. Preparation of the NMP solvate of N-(2-hydroxyacetyl)-5-(4-piperidyl)-4-(4-pyrimidinyl)-3-(4-chlorophenyl)pyrazole (12).

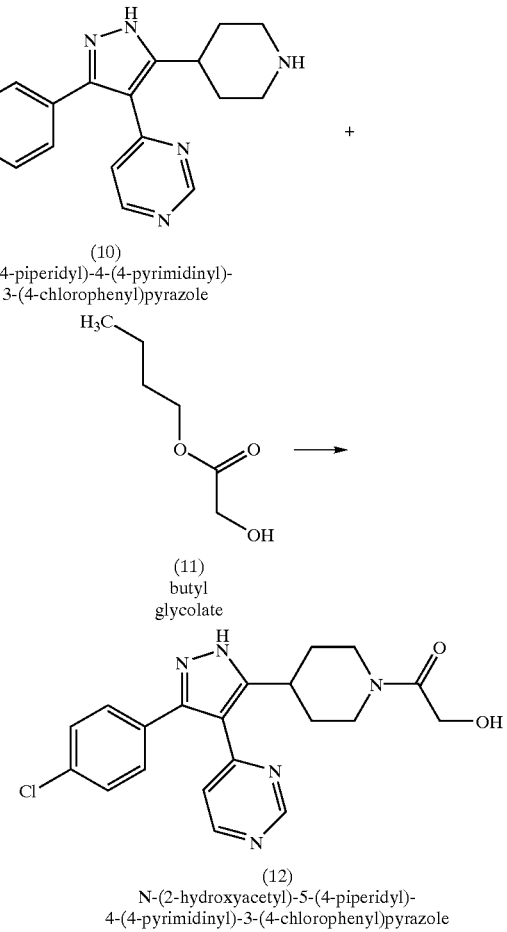

(10)
5-(4-piperidyl)-4-(4-pyrimidinyl)-
3-(4-chlorophenyl)pyrazole

(11)
butyl glycolate

(12)
N-(2-hydroxyacetyl)-5-(4-piperidyl)-
4-(4-pyrimidinyl)-3-(4-chlorophenyl)pyrazole The following discussion describes three variations of this reaction:

A. First Variation

This reaction was conducted in a jacketed, 0.1 L reactor equipped with an agitator, nitrogen purge, thermocouple, and condenser. The reactor was charged with 5-(4-piperidyl)-4-(4-pyrimidinyl)-3-(4-chlorophenyl)pyrazole

(10) prepared as shown in Part E (10 g, 0.029 mol); 1-methyl-2-pyrrolidinone (20 g, 0.20 mol); butyl glycolate (11) (9.7 g, 0.073 mol), and 1,8-diazabicyclo[5.4.0]undec-7-ene ("DBU") (0.45 g, 0.0029 mol). After stirring was initiated, the mixture was heated to about 110° C., and then maintained at that temperature for 3 hours. At that point, it was determined by HPLC that conversion from starting material to product had ceased (i.e., <3 area % starting material remained). The reactor contents were then cooled to 25° C. over 1 hour. Ethanol 3A (1.74 g, 0.038 mol) was then charged to the reactor. The resulting mixture was maintained at 25° C. for an additional hour, and then further cooled to 0° C. over 30 minutes. This temperature was maintained for an additional 2 hours. The solids were collected via filtration using a 4 micron filter cloth, washed with NMP (2×18 g), and air-dried on the filter giving rise to the NMP solvate of the desired product, which was analyzed via differential scanning calorimetry ("DSC"). The solids were introduced to the reactor along with 100 mL of ethanol. The resulting mixture was then heated to reflux, and maintain at reflux for 4 hours. Afterward, the mixture was cooled to 15° C. over 3 hours. The product was then isolated by filtration using a 4 micron filter cloth, washed (using a displacement wash) with ethanol 3A (2×33 g), and air-dried on the filter. This yielded 9.0 g of white/off-white/yellow crystals (78% yield) (HPLC weight % >98%).

TABLE 21

Reaction Summary for Part F

|  | MW | equiv. | wt. (g) | moles | density (g/mL) | volume (mL) |
|---|---|---|---|---|---|---|
| materials |  |  |  |  |  |  |
| compound (10) | 339.83 | 1.00 | 10.0 | 0.029 |  |  |
| 1-methyl-2-pyrrolidinone | 99.13 | 6.96 | 20.0 | 0.20 | 1.028 | 15.6 |
| 1,8-Diazabicyclo-(5.4.0)undec-7-ene | 152.24 | 0.10 | 0.45 | 0.0029 | 1.018 | 0.44 |
| compound (11) | 132.16 | 2.5 | 9.7 | 0.073 | 1.019 | 9.5 |
| Ethanol 3A | 46.01 | 1.31 | 1.7 | 0.038 | 0.790 | 2.2 |
| 1-methly-2-pyrrolidinone (wash) | 99.13 | 6.26 | 18.0 | 0.18 | 1.028 | 17.5 |
| 1-methly-2-pyrrolidinone (wash) | 99.13 | 6.26 | 18.0 | 0.18 | 1.028 | 17.5 |
| Ethanol 3A | 46.01 | 59.2 | 79 | 1.72 | 0.790 | 100 |
| Ethanol 3A (wash) | 46.01 | 24.7 | 33 | 0.72 | 0.790 | 26.1 |
| Ethanol 3A (wash) | 46.01 | 24.7 | 33 | 0.72 | 0.790 | 26.1 |
| product |  |  |  |  |  |  |
| compound (12) | 397.86 | (1.00) | (11.5) | (0.029) |  |  |

The numbers in parenthesis in the above table are theoretical.

B. Second Variation

In the second variation, the reaction was conducted in a jacketed, 49 L reactor equipped with a retreat curve agitator, nitrogen purge, and metering pump. This reactor was charged with 5-(4-piperidyl)-4-(4-pyrimidinyl)-3-(4-chlorophenyl)pyrazole (10) prepared as shown in Part E (1.9 Kg, 5.6 mol) and 1-Methyl-2-pyrrolidinone (3.8 Kg, 38.3 mol). After initiating agitation at 75 rpm and allowing the mixture to stir for 6 minutes, the reactor was further charged with butyl glycolate (11) (1.85 Kg, 14 mol, added via an addition funnel) and DBU (85.12 g, 0.54 mol) while continuing to stir the contents. The mixture was then heated to 110° C. over 23 minutes, and then held at that temperature for 3 hours. A sample taken 15 minutes after the 110° C. temperature had been reached indicated a 87.2% conversion of the 5-(4-piperidyl)-4-(4-pyrimidinyl)-3-(4-chlorophenyl) pyrazole (10), a sample taken 60 minutes after the 110° C. temperature had been reached indicated a 98.7% conversion of the 5-(4-piperidyl)-4-(4-pyrimidinyl)-3-(4-chlorophenyl) pyrazole (10), and a sample taken 120 minutes after the 110° C. temperature had been reached indicated a 99.7% conversion of the 5-(4-piperidyl)-4-(4-pyrimidinyl)-3-(4-chlorophenyl)pyrazole (10). After the heating, the reaction mixture was cooled to approximately 25° C. over 1 hour and 5 minutes (the final baffle temperature was 28.5° C., while the contents at the bottom were at 22.2° C.). A sample was taken, and then the reactor was charged with Ethanol 3A (12.35 Kg, 268 mol) over 55 minutes. After the ethanol was charged, a sample was taken. The mixture was then stirred for 65 minutes. A sample taken after the first 30 minutes of the stirring indicated that 2.8% of the N-(2-hydroxyacetyl)-5-(4-piperidyl)-4-(4-pyrimidinyl)-3-(4-chlorophenyl) pyrazole product (12) remained in solution, and a sample taken after 60 minutes of the stirring indicated that 3.4% of the N-(2-hydroxyacetyl)-5-(4-piperidyl)-4-(4-pyrimidinyl)-3-(4-chlorophenyl)pyrazole product (12) was in solution. The mixture was next heated to reflux over 1 hour and 2 minutes, and then maintained at reflux for 4 hours. Supernatant and solid samples were collected every 30 minutes. After the 4 hours of refluxing, the mixture was cooled to 5° C. at a rate of 0.25° C./minute, and then maintained at that temperature overnight. The resulting product was filtered, providing 17.46 Kg of filtrate. The cake was washed with ethanol 3A (2×3.14 Kg, 68.3 mol). The washed cake was then pull dried to LOD=0.67%. The amount of resulting wet cake was 2.00 Kg (89.7% non-assay adjusted molar yield). The NMP concentration in the wet cake was determined using gas chromatography ("GC") to be 518 ppm. The NMP concentration in the wet cake using the GC method with solid phase micro-extraction ("SPME") was 580 ppm.

A portion of the wet cake (1.0 Kg, 2.51 mole) was then combined with ethanol 3A (9.0 Kg, 11.38 L, 196 mol) by vacuum in the same reactor. Agitation was set to 80 RPM. The mixture was heated to reflux (i.e., 78–80° C.) over 33 minutes, and then held at reflux for 3 hours and 10 minutes. Samples were taken after the first 1 hour and 10 minutes, after the first 2 hours and 10 minutes, and at the end of the 3 hours and 10 minutes. The mixture was then cooled to 5° C. over 3 hours and 10 minutes, and held at 5° C. overnight (i.e., approximately 16 hours and 50 minutes). Samples were taken during the cool-down period. The solids were filtered using a pressure filter, and a sample was taken from the mother liquor. The amount of mother liquor collected was 8.68 Kg. The cake was washed with ethanol 3A (2×3.14 Kg (68.3 mol), samples taken after each wash). The cake was then pull dried for 1–2 hours to LOD=0.31%. This produced 0.892 Kg of wet cake (89.6% non-assay adjusted molar yield). Total impurities in the cake were determined to be 0.46% (by weight), with NMP being present at a concentration of 0.01% (by weight) and 5-(4-piperidyl)-4-(4-pyrimidinyl)-3-(4-chlorophenyl)pyrazole (10) being at a concentration of 0.01% (by weight).

C. Third Variation

In the third variation, the reaction was conducted in a jacketed, 0.1 L reactor equipped with an agitator, nitrogen purge, thermocouple, and condenser. This reactor was charged with 5-(4-piperidyl)-4-(4-pyrimidinyl)-3-(4- chlorophenyl)pyrazole (10) prepared as shown in Part E (1.9 Kg, 5.6 mol, LOC=0.40%) and 1-Methyl-2-pyrrolidinone (3.8 Kg, 38.3 mol). After initiating stirring at 75 RPM, the reactor was further charged with butyl glycolate (11) (1.85 Kg, 14 mol) via an addition funnel and DBU (85.08 g, 0.56 mol) while continuing to stir the contents. The mixture was then heated to 110° C. over 50 minutes, and then held at that temperature for 3 hours and 25 minutes. A sample taken 15 minutes after the 110° C. temperature had been reached indicated a 89.8% conversion of the 5-(4-piperidyl)-4-(4-pyrimidinyl)-3-(4-chlorophenyl)pyrazole (10), a sample taken 60 minutes after the 110° C. temperature had been reached indicated a 99.1% conversion of the 5-(4-piperidyl)-4-(4-pyrimidinyl)-3-(4-chlorophenyl)pyrazole (10), and a sample taken 180 minutes after the 110° C. temperature had been reached indicated a 99.6% conversion of the 5-(4-piperidyl)-4-(4-pyrimidinyl)-3-(4-chlorophenyl)pyrazole (10). The mixture was cooled to 40° C. over 2 hours and 20 minutes, and a sample was taken. The reactor was then charged with ethanol 3A (0.76 Kg, 16.5 mol) over 23 minutes. After the ethanol was added, a sample of the solid was taken. The mixture was heated to reflux over 1 hour and 20 minutes, and then held at reflux for 4 hours. Supernatant and solid samples were collected every 60 minutes. After the refluxing, the mixture was cooled to 5° C. at a rate of 0.25° C./min, and then held at that temperature overnight. Samples of the solid and supernatant were collected. The mixture was then filtered, producing 3.54 Kg of filtrate (a sample of the filtrate was collected). The cake was washed with methyl t-butyl ether ("MTBE", 2×3.14 Kg (35.6 mol), samples of the MTBE were collected after each wash). The washed cake was then pull dried for 1 hour and 15 minutes (LOD= 0.47%). This produced 2.56 Kg of wet cake. The non-assay adjusted yield was 92.1%. The NMP concentration in the wet cake was determined using gas chromatography to be 518 ppm. The NMP concentration in the wet cake using the GC method with SPME was 580 ppm. The wet cake was then treated using two alternative procedures:

i. First alternative Wet Cake Treatment

A portion of the wet cake prepared above (1.2 Kg, LOD–0.47%) was charged to the same reactor, along with ethanol 3A (9.0 Kg, 11.38 L) via vacuum. This produced a thick slurry. The agitator speed was set to 95 RPM. The slurry was heated to reflux (i.e., 78–80° C.) over 16 minutes, and then held at reflux for 5 hours. Samples were collected when the mixture first reached reflux, 102 minutes later, 162 minutes later, 186 minutes later, and 251 minutes later. The mixture was then cooled to 5° C. over 2 hours and 46 minutes, and then held at that temperature overnight (i.e., 11 hours and 59 minutes). The product was filtered with a pressure filter producing 8.50 Kg of mother liquor (a sample of the mother liquor was collected). The cake was washed with ethanol (2×1.60 Kg, samples taken after each wash). The cake was then pull dried for a few hours. This produced 1.07 Kg of wet cake (LOD=18.0%). After collecting a sample, the wet cake was then dried in a vacuum dryer at 50° C. over a approximately a weekend. This produced 0.894 Kg wet cake (LOD=0.51%) with a 93.0% non-assay adjusted molar yield. Total impurities in the cake were determined to be 0.45% (by weight), with NMP being present at a concentration of 0.01% (by weight) and 5-(4-piperidyl)-4-(4-pyrimidinyl)-3-(4-chlorophenyl)pyrazole (10) being at a concentration of 0.01% (by weight).

ii. Second Alternative Wet Cake Treatment

A second portion of the cake (4 g) was charged to a nitrogen-purged, 100 ml, jacketed vessel equipped with a chiller and an overhead stirrer. Ethanol 3A (34.2 g ethanol and 1.8 g methanol) and DBU (0.15 g) were pre-mixed, and then charged to the reactor while stirring the contents at 250 RPM. Stirring was continued for 1 hour at room temperature. The contents were then heated to reflux for 1 hour, and then cooled to 0° C. for 3 hours. The next day, the solids were filtered and washed with ethanol 3A. The resulting cake was pull-dried overnight with a house vacuum. The solids were then placed in a vacuum oven at approximately 50° C. for another several hours.

The examples herein can be performed by substituting the generically or specifically described reactants and/or operating conditions of this invention for those used in the preceding examples.

In view of the above, it will be seen that the several objects of the invention are achieved. As various changes could be made in the above methods, combinations and compositions of the present invention without departing from the scope of the invention, it is intended that all matter contained in the above description be interpreted as illustrative and not in a limiting sense. All documents mentioned in this application are expressly incorporated by reference as if fully set forth at length.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. Form I crystalline N-(2-hydroxyacetyl)-5-(4-piperidyl)-4-(4-pyrimidinyl)-3-(4-chlorophenyl)pyrazole having an X-ray powder diffraction pattern comprising a peak selected from the group consisting of 6.2±0.2, 12.3±0.2, 14.9±0.2, 17.1±0.2, and 19.5±0.2 degrees 2θ.

2. The crystalline N-(2-hydroxyacetyl)-5-(4-piperidyl)-4-(4-pyrimidinyl)-3-(4-chlorophenyl)pyrazole of claim 1 having a melting point in a range from about 239° C. to about 241° C.

3. The crystalline N-(2-hydroxyacetyl)-5-(4-piperidyl)-4-(4-pyrimidinyl)-3-(4-chlorophenyl)pyrazole of claim 1 having an infrared absorption band profile comprising an absorption band at about 1632 $cm^{-1}$.

4. The crystalline N-(2-hydroxyacetyl)-5-(4-piperidyl)-4-(4-pyrimidinyl)-3-(4-chlorophenyl)pyrazole of claim 1 having a melting point in a range from about 239° C. to about 241° C., an infrared absorption band profile comprising an absorption band at about 1632 $cm^{-1}$, and an X-ray powder diffraction pattern comprising a peak at 6.2±0.2 degrees 2θ.

5. The crystalline N-(2-hydroxyacetyl)-5-(4-piperidyl)-4-(4-pyrimidinyl)-3-(4-chlorophenyl)pyrazole of claim 1 having an X-ray powder diffraction pattern substantially as shown in FIG. 1.

6. Form II crystalline N-(2-hydroxyacetyl)-5-(4-piperidyl)-4-(4-pyrimidinyl)-3-(4-chlorophenyl)pyrazole having an X-ray powder diffraction pattern comprising a peak selected from the group consisting of 4.7±0.2, 9.6±0.2, 14.5±0.2, 16.2±0.2 and 20.1±0.2 degrees 2θ.

7. The crystalline N-(2-hydroxyacetyl)-5-(4-piperidyl)-4-(4-pyrimidinyl)-3-(4-chlorophenyl)pyrazole of claim 6 having a melting point in a range from about 210° C. to about 212° C.

8. The crystalline N-(2-hydroxyacetyl)-5-(4-piperidyl)-4-(4-pyrimidinyl)-3-(4-chlorophenyl)pyrazole of claim 6 having an infrared absorption band profile comprising an absorption band at about 1635 $cm^{-1}$.

9. The crystalline N-(2-hydroxyacetyl)-5-(4-piperidyl)-4-(4-pyrimidinyl)-3-(4-chlorophenyl)pyrazole of claim 6 having a melting point in a range from about 210° C. to about 212° C., an infrared absorption band profile comprising an absorption band at about 1635 cm$^{-1}$, and an X-ray powder diffraction pattern comprising a peak at 4.7±0.2 degrees 2θ.

Figure 2:
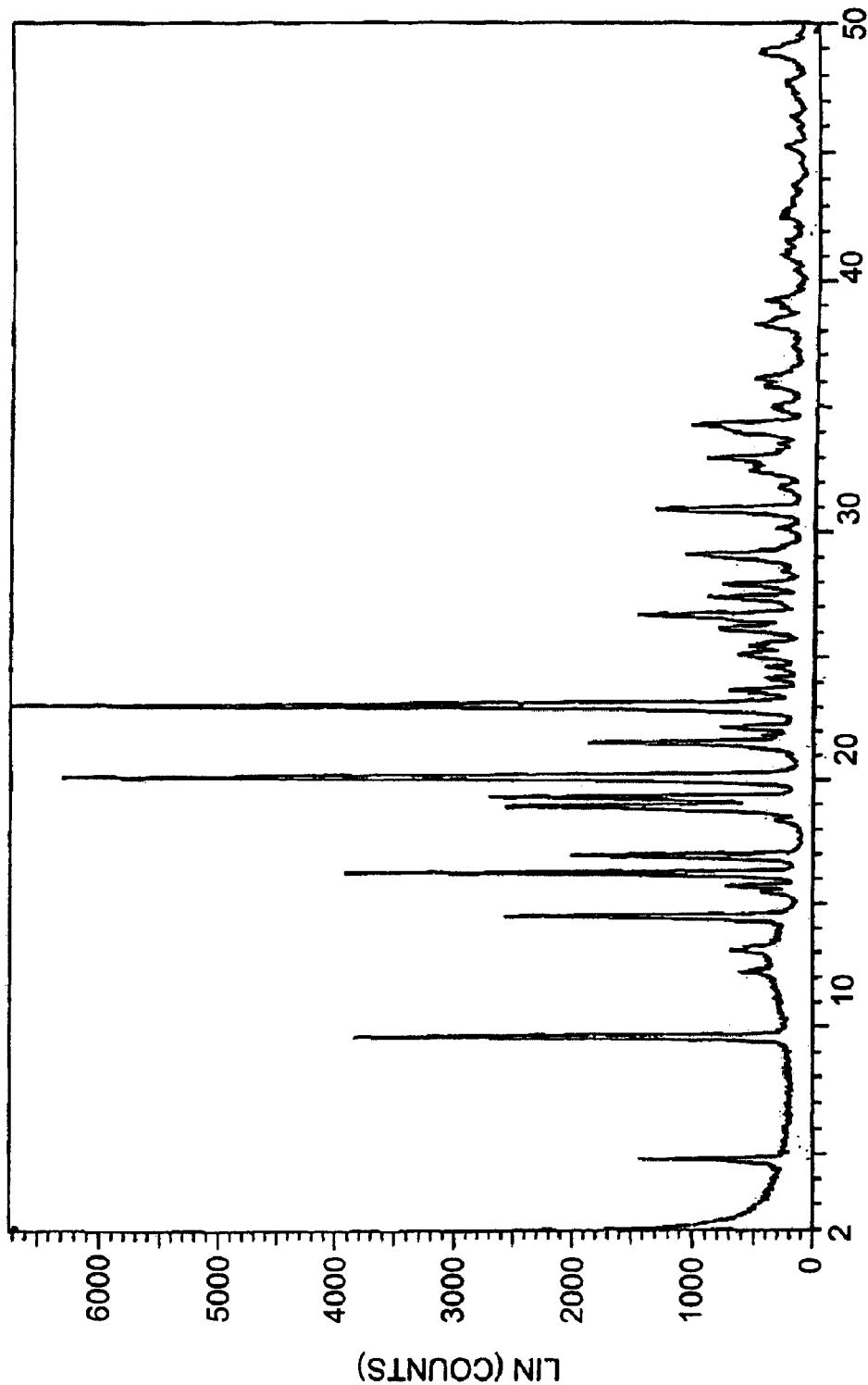
FIG. 2 shows an illustrative X-ray powder diffraction pattern for the Form II polymorph of Compound 1.

10. The crystalline N-(2-hydroxyacetyl)-5-(4-piperidyl)-4-(4-pyrimidinyl)-3-(4-chlorophenyl)pyrazole of claim 6 having an X-ray powder diffraction pattern substantially as shown in FIG. 2.

11. Form III crystalline N-(2-hydroxyacetyl)-5-(4-piperidyl)-4-(4-pyrimidinyl)-3-(4-chlorophenyl)pyrazole having an X-ray powder diffraction pattern comprising a peak selected from the group consisting of 10.5±0.2, 11.7±0.2, 12.4±0.2 and 19.1±0.2 degrees 2θ.

Figure 3:
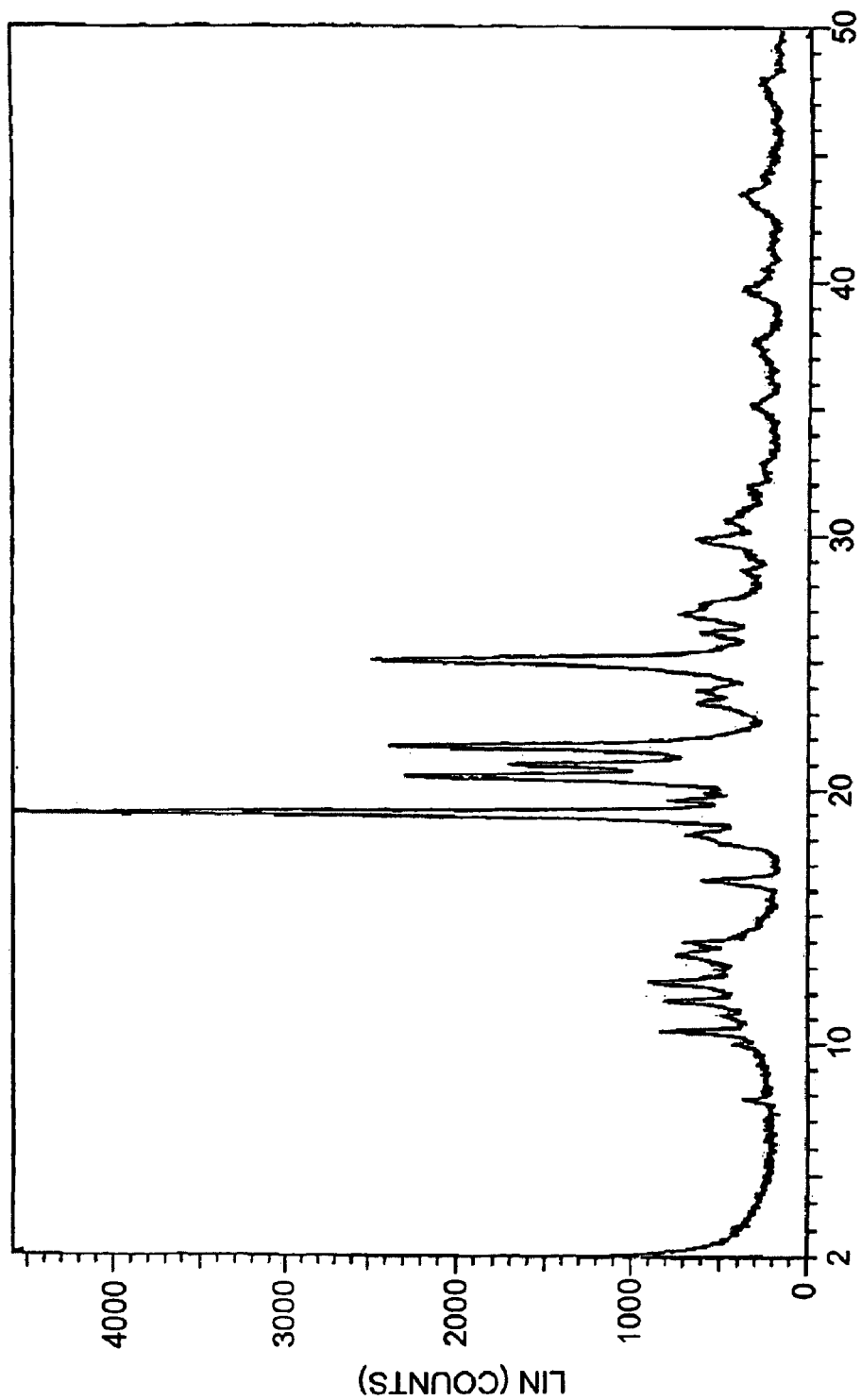
FIG. 3 shows an illustrative X-ray powder diffraction pattern for the Form III polymorph of Compound 1.
Figure 4:
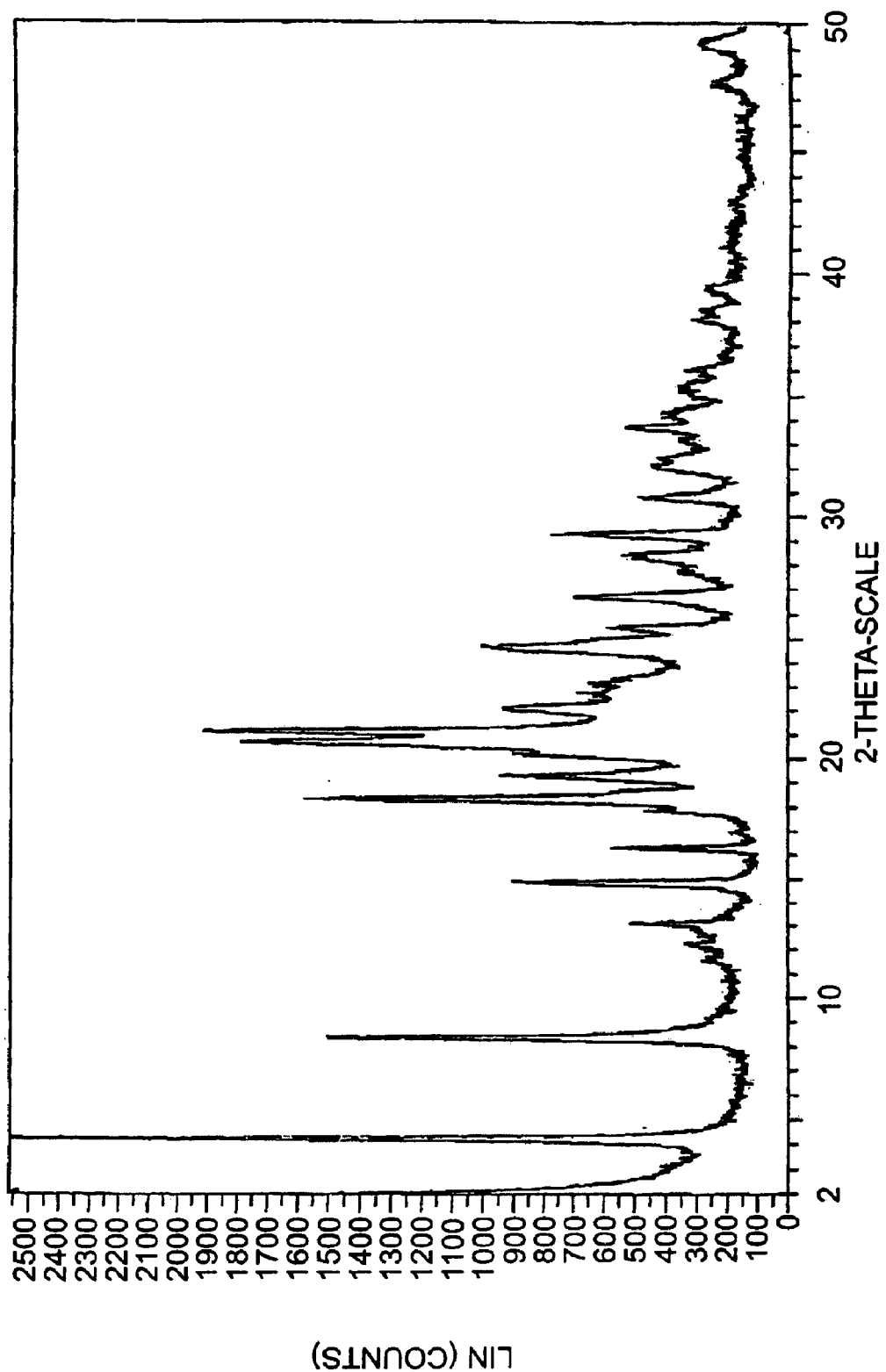
FIG. 4 shows an illustrative X-ray powder diffraction pattern for the acetic acid solvate of Compound 1.
Figure 5:
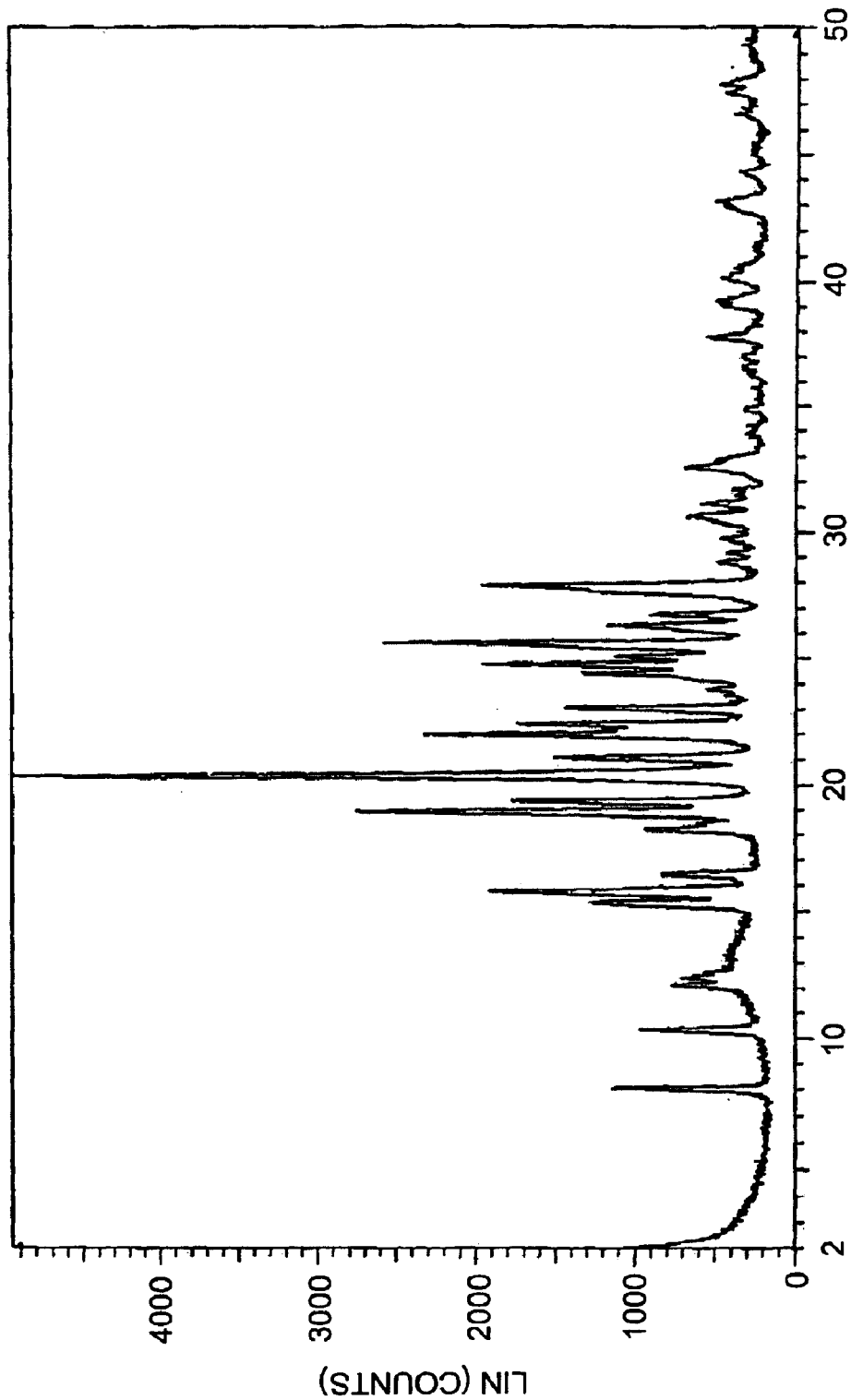
FIG. 5 shows an illustrative X-ray powder diffraction pattern for the NMP solvate of Compound 1.
Figure 6:
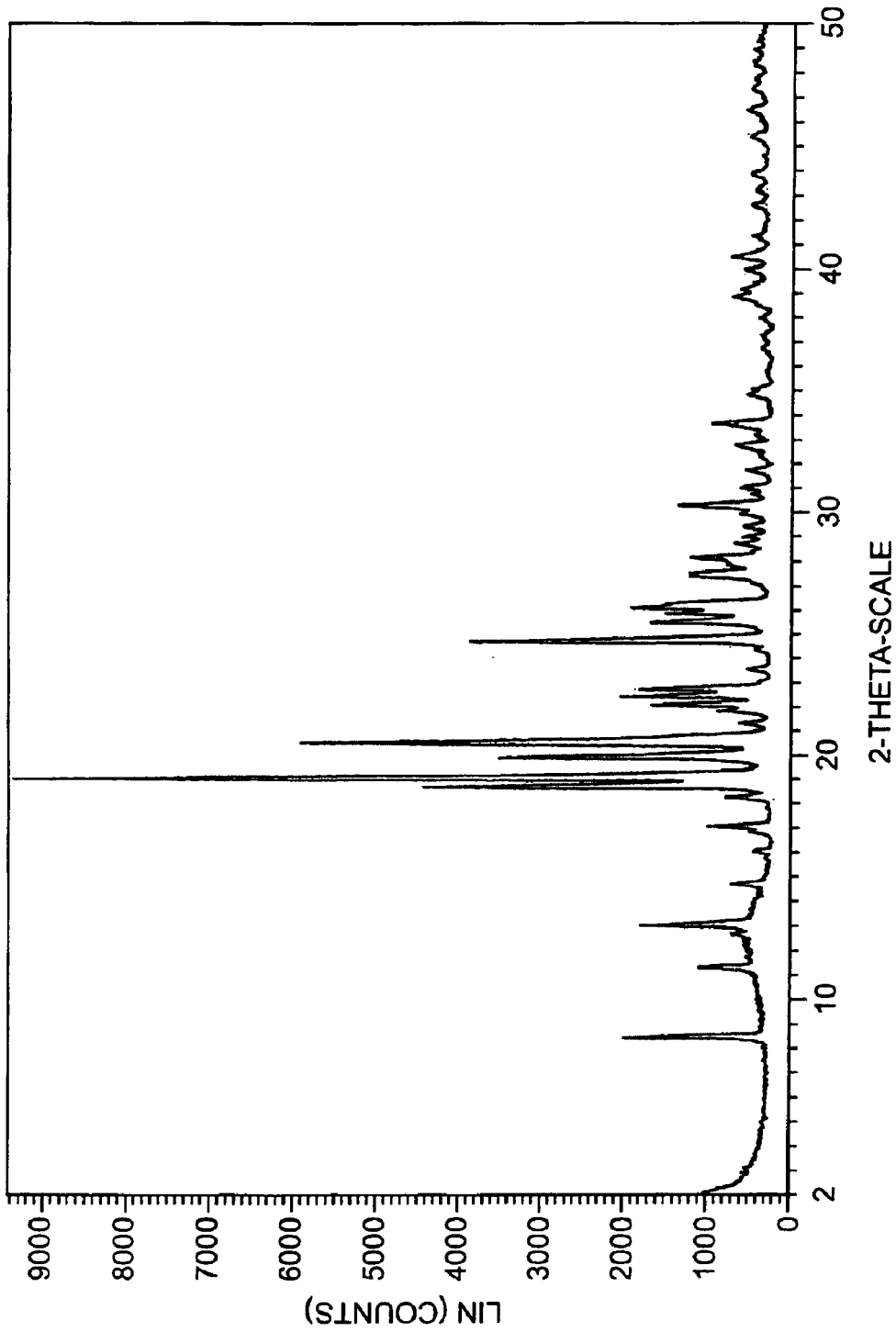
FIG. 6 shows an illustrative X-ray powder diffraction pattern for the monohydrate crystalline form of Compound 1.
Figure 7:
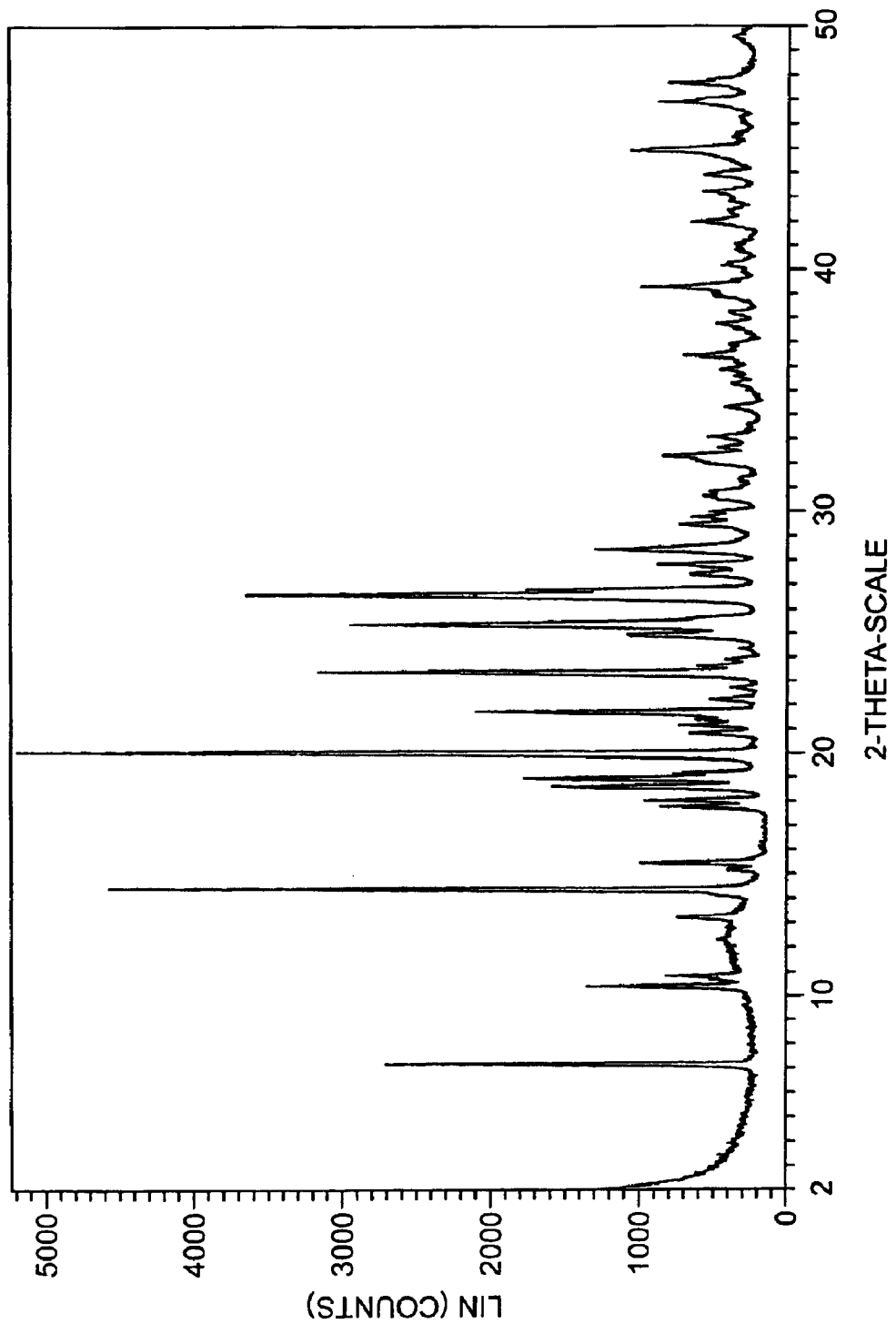
FIG. 7 shows an illustrative X-ray powder diffraction pattern for the dihydrate crystalline form of Compound 1.
Figure 8:
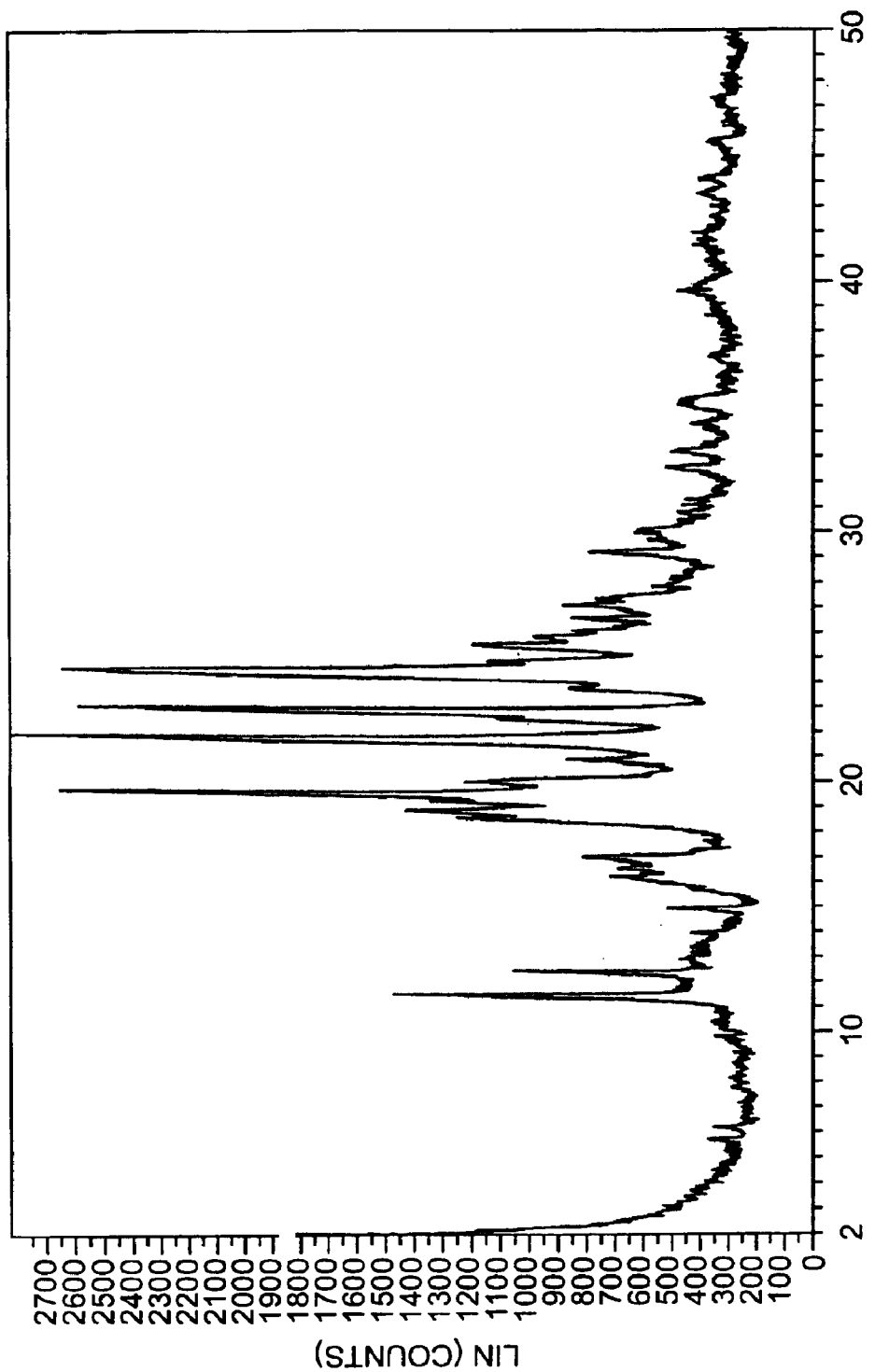
FIG. 8 shows an illustrative X-ray powder diffraction pattern for the crystalline sodium salt of Compound 1.
Figure 9:
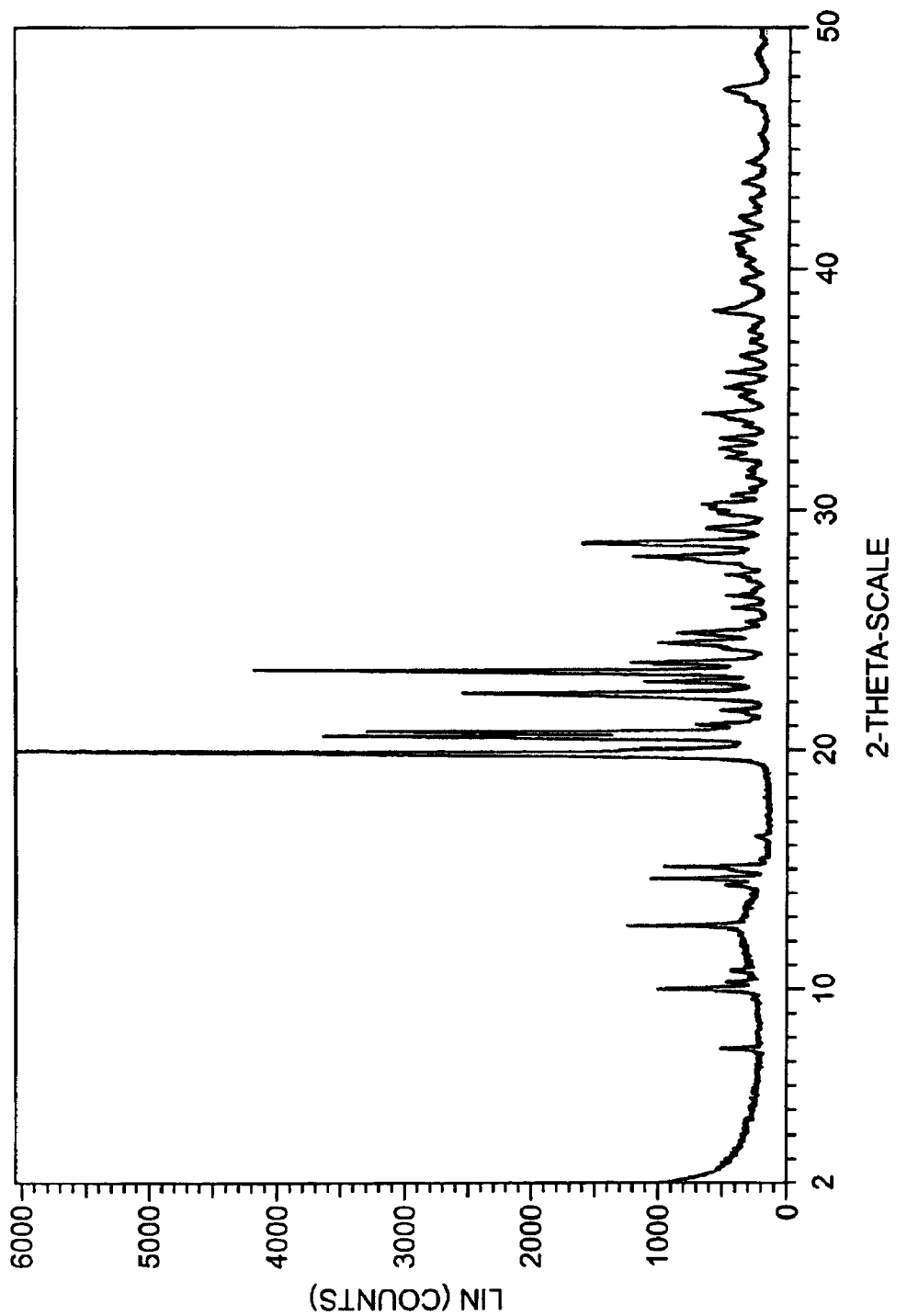
FIG. 9 shows an illustrative X-ray powder diffraction pattern for the crystalline hydrochloride salt of Compound 1.
Figure 10:
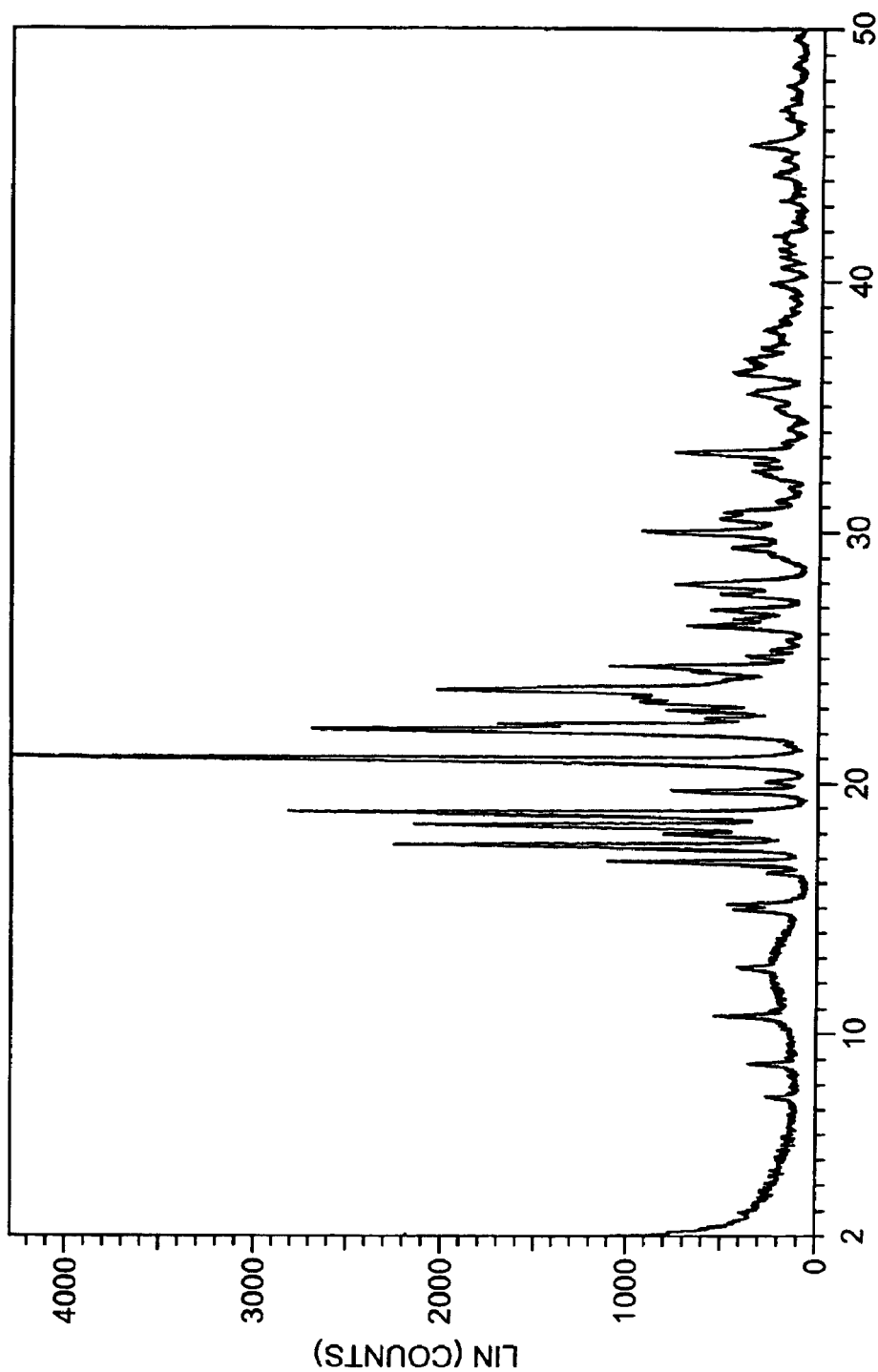
FIG. 10 shows an illustrative X-ray powder diffraction pattern for the crystalline methanesulfonic acid (mesylate) salt of Compound 1.
Figure 11:
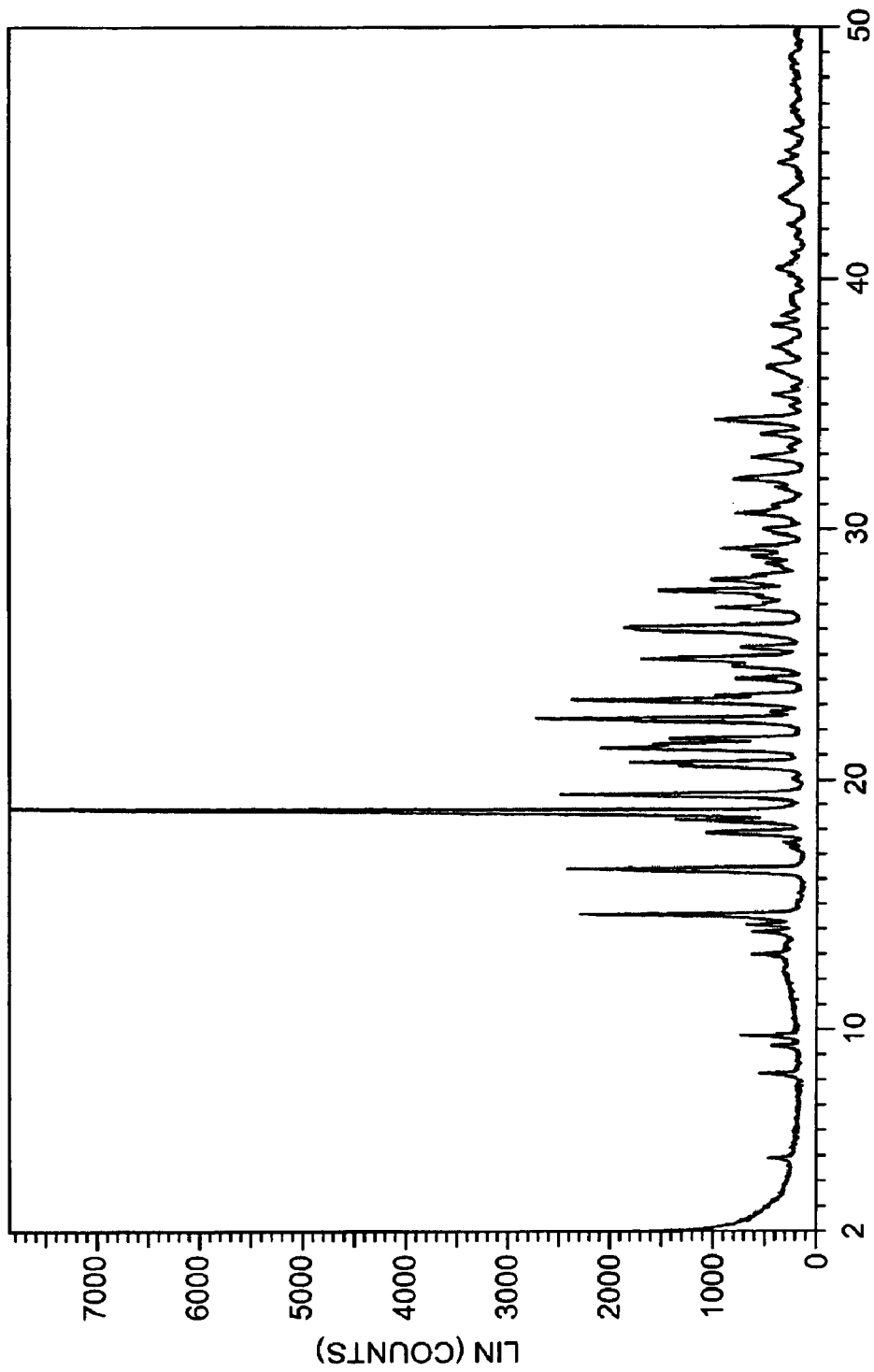
FIG. 11 shows an illustrative X-ray powder diffraction pattern for the crystalline p-toluenesulfonic acid (tosylate) salt of Compound 1.

12. The crystalline N-(2-hydroxyacetyl)-5-(4-piperidyl)-4-(4-pyrimidinyl)-3-(4-chlorophenyl)pyrazole of claim 28 having an X-ray powder diffraction pattern substantially as shown in FIG. 3.

13. A solvated crystalline form that is an N-methylpyrrolidone solvated crystalline form of N-(2-hydroxyacetyl)-5-(4-piperidyl)-4-(4-pyrimidinyl)-3-(4-chlorophenyl)pyrazole.

14. A solvated crystalline form that is an acetic acid solvated crystalline form of N-(2-hydroxyacetyl)-5-(4-piperidyl)-4-(4-pyrimidinyl)-3-(4-chlorophenyl)pyrazole.

15. A hydrated crystalline form that is a monohydrate crystalline form of N-(2-hydroxyacetyl)-5-(4-piperidyl)-4-(4-pyrimidinyl)-3-(4-chlorophenyl)pyrazole.

16. A hydrated crystalline form that is a dihydrate crystalline form of N-(2-hydroxyacetyl)-5-(4-piperidyl)-4-(4-pyrimidinyl)-3-(4-chlorophenyl)pyrazole.

17. A crystalline salt of N-(2-hydroxyacetyl)-5-(4-piperidyl)-4-(4-pyrimidinyl)-3-(4-chlorophenyl)pyrazole selected from the group consisting of:
(a) a crystalline sodium salt of N-(2-hydroxyacetyl)-5-(4-piperidyl)-4-(4-pyrimidinyl)-3-(4-chlorophenyl)pyrazole,
(b) a crystalline mesylate salt of N-(2-hydroxyacetyl)-5-(4-piperidyl)-4-(4-pyrimidinyl)-3-(4-chlorophenyl)pyrazole, and
(c) a crystalline tosylate salt of N-(2-hydroxyacetyl)-5-(4-piperidyl)-4-(4-pyrimidinyl)-3-(4-chlorophenyl)pyrazole.

18. The crystalline salt of claim 17 that is a crystalline sodium salt of N-(2-hydroxyacetyl)-5-(4-piperidyl)-4-(4-pyrimidinyl)-3-(4-chlorophenyl)pyrazole.

19. The crystalline salt of claim 17 that is a crystalline mesylate salt of N-(2-hydroxyacetyl)-5-(4-piperidyl)-4-(4-pyrimidinyl)-3-(4-chlorophenyl)pyrazole.

20. The crystalline salt of claim 17 that is a crystalline tosylate salt of N-(2-hydroxyacetyl)-5-(4-piperidyl)-4-(4-pyrimidinyl)-3-(4-chlorophenyl)pyrazole.

21. A pharmaceutical composition comprising N-(2-hydroxyacetyl)-5-(4-piperidyl)-4-(4-pyrimidinyl)-3-(4-chlorophenyl)pyrazole and one or more pharmaceutically acceptable excipients, wherein a detectable amount of the N-(2-hydroxyacetyl)-5-(4-piperidyl)-4-(4-pyrimidinyl)-3-(4-chlorophenyl)pyrazole is present as Form I crystalline N-(2-hydroxyacetyl)-5-(4-piperidyl)-4-(4-pyrimidinyl)-3-(4-chlorophenyl)pyrazole.

22. The pharmaceutical composition of claim 21 wherein at least about 50% of the N-(2-hydroxyacetyl)-5-(4-piperidyl)-4-(4-pyrimidinyl)-3-(4-chlorophenyl)pyrazole is present as Form I crystalline N-(2-hydroxyacetyl)-5-(4-piperidyl)-4-(4-pyrimidinyl)-3-(4-chlorophenyl)pyrazole.

23. The pharmaceutical composition of claim 21 wherein at least about 90% of the N-(2-hydroxyacetyl)-5-(4-piperidyl)-4-(4-pyrimidinyl)-3-(4-chlorophenyl)pyrazole is present as Form I crystalline N-(2-hydroxyacetyl)-5-(4-piperidyl)-4-(4-pyrimidinyl)-3-(4-chlorophenyl)pyrazole.

24. The pharmaceutical composition of claim 21 wherein the N-(2-hydroxyacetyl)-5-(4-piperidyl)-4-(4-pyrimidinyl)-3-(4-chlorophenyl)pyrazole present in the composition is substantially phase pure Form I crystalline N-(2-hydroxyacetyl)-5-(4-piperidyl)-4-(4-pyrimidinyl)-3-(4-chlorophenyl)pyrazole.

25. The pharmaceutical composition of claim 21 wherein the composition further comprises Form II crystalline N-(2-hydroxyacetyl)-5-(4-piperidyl)-4-(4-pyrimidinyl)-3-(4-chlorophenyl)pyrazole.

26. The pharmaceutical composition of claim 21 wherein the amount of N-(2-hydroxyacetyl)-5-(4-piperidyl)-4-(4-pyrimidinyl)-3-(4-chlorophenyl)pyrazole present in the composition is between about 0.1 mg to about 1000 mg.

27. The pharmaceutical composition of claim 21 wherein the amount of N-(2-hydroxyacetyl)-5-(4-piperidyl)-4-(4-pyrimidinyl)-3-(4-chlorophenyl)pyrazole present in the composition is between about 0.1 mg to about 100 mg.

28. A pharmaceutical composition comprising N-(2-hydroxyacetyl)-5-(4-piperidyl)-4-(4-pyrimidinyl)-3-(4-chlorophenyl)pyrazole and one or more pharmaceutically acceptable excipients, wherein a detectable amount of the N-(2-hydroxyacetyl)-5-(4-piperidyl)-4-(4-pyrimidinyl)-3-(4-chlorophenyl)pyrazole is present as Form II crystalline N-(2-hydroxyacetyl)-5-(4-piperidyl)-4-(4-pyrimidinyl)-3-(4-chlorophenyl)pyrazole.

29. The pharmaceutical composition of claim 28 wherein at least about 50% of the N-(2-hydroxyacetyl)-5-(4-piperidyl)-4-(4-pyrimidinyl)-3-(4-chlorophenyl)pyrazole is present as Form II crystalline N-(2-hydroxyacetyl)-5-(4-piperidyl)-4-(4-pyrimidinyl)-3-(4-chlorophenyl)pyrazole.

30. The pharmaceutical composition of claim 28 wherein at least about 90% of the N-(2-hydroxyacetyl)-5-(4-piperidyl)-4-(4-pyrimidinyl)-3-(4-chlorophenyl)pyrazole is present as Form II crystalline N-(2-hydroxyacetyl)-5-(4-piperidyl)-4-(4-pyrimidinyl)-3-(4-chlorophenyl)pyrazole.

31. The pharmaceutical composition of claim 28 wherein the N-(2-hydroxyacetyl)-5-(4-piperidyl)-4-(4-pyrimidinyl)-3-(4-chlorophenyl)pyrazole present in the composition is substantially phase pure Form II crystalline N-(2-hydroxyacetyl)-5-(4-piperidyl)-4-(4-pyrimidinyl)-3-(4-chlorophenyl)pyrazole.

32. The pharmaceutical composition of claim 28 wherein the amount of N-(2-hydroxyacetyl)-5-(4-piperidyl)-4-(4-pyrimidinyl)-3-(4-chlorophenyl)pyrazole present in the composition is between about 0.1 mg to about 1000 mg.

33. The pharmaceutical composition of claim 28 wherein the amount of N-(2-hydroxyacetyl)-5-(4-piperidyl)-4-(4-pyrimidinyl)-3-(4-chlorophenyl)pyrazole present in the composition is between about 0.1 mg to about 100 mg.

34. A pharmaceutical composition comprising N-(2-hydroxyacetyl)-5-(4-piperidyl)-4-(4-pyrimidinyl)-3-(4-chlorophenyl)pyrazole and one or more pharmaceutically acceptable excipients, wherein a detectable amount of the N-(2-hydroxyacetyl)-5-(4-piperidyl)-4-(4-pyrimidinyl)-3-(4-chlorophenyl)pyrazole is present as Form III crystalline N-(2-hydroxyacetyl)-5-(4-piperidyl)-4-(4-pyrimidinyl)-3-(4-chlorophenyl)pyrazole.

35. The pharmaceutical composition of claim 34 wherein the amount of N-(2-hydroxyacetyl)-5-(4-piperidyl)-4-(4-pyrimidinyl)-3-(4-chlorophenyl)pyrazole present in the composition is between about 0.1 mg to about 1000 mg.

36. The pharmaceutical composition of claim 34 wherein the amount of N-(2-hydroxyacetyl)-5-(4-piperidyl)-4-(4- pyrimidinyl)-3-(4-chlorophenyl)pyrazole present in the composition is between about 0.1 mg to about 100 mg.

37. A method of treating rheumatoid arthritis, the method comprising administering to a subject having or susceptible to such condition or disorder a therapeutically or prophylactically effective amount of the composition of claim 21.

38. A method of treating rheumatoid arthritis, the method comprising administering to a subject having or susceptible to such condition or disorder a therapeutically or prophylactically effective amount of the composition of claim 28.

39. A method of treating rheumatoid arthritis, the method comprising administering to a subject having or susceptible to such condition or disorder a therapeutically or prophylactically effective amount of the composition of claim 34.

* * * * *